(12) United States Patent
Barton

(10) Patent No.: US 10,111,934 B2
(45) Date of Patent: Oct. 30, 2018

(54) IGF-1 PROTEINS AND THERAPEUTIC USES THEREOF

(71) Applicant: THE TRUSTEES OF THE UNIVERSITY OF PENNSYLVANIA, Philadelphia, PA (US)

(72) Inventor: Elisabeth R. Barton, Philadelphia, PA (US)

(73) Assignee: THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 52 days.

(21) Appl. No.: 14/584,481

(22) Filed: Dec. 29, 2014

(65) Prior Publication Data

US 2015/0190477 A1 Jul. 9, 2015

Related U.S. Application Data

(63) Continuation of application No. PCT/US2013/050326, filed on Jul. 12, 2013.

(60) Provisional application No. 61/671,489, filed on Jul. 13, 2012, provisional application No. 61/680,424, filed on Aug. 7, 2012.

(51) Int. Cl.
*A61K 38/30* (2006.01)

(52) U.S. Cl.
CPC .................. *A61K 38/30* (2013.01)

(58) Field of Classification Search
None
See application file for complete search history.

(56) References Cited

U.S. PATENT DOCUMENTS

| | | |
|---|---|---|
| 2009/0318355 A1 | 12/2009 | Chen et al. |
| 2010/0234290 A1 | 9/2010 | Glass et al. |
| 2011/0033412 A1 | 2/2011 | Rosenthal et al. |
| 2012/0093775 A1 | 4/2012 | Alonso et al. |

OTHER PUBLICATIONS

UniProtKB-P05019 (IGF1_Human) Nov. 27, 2016 p. 1-12.*
Kristensen, C., et al, Alanine Scanning Mutagenesis of Insulin, The Journal of Biological Chemistry, vol. 272, No. 20, Issue of May 16, pp. 12978-12983, 1997.*
Duguay, SJ, Mutational Analysis of the Insulin-like Growth Factor I Prohormone Processing Site, Journal of Biological Chemistry, vol. 270, 17566-17574 (1995).*
International Search Report dated Dec. 19, 2013 in PCT/US2013/050326.
Adams et al., "Localized infusion of IGF-I results in skeletal muscle hypertrophy in rats," J Appl Physiol 84:1716-1722 (1998).
Almon, "Fiber-type discrimination in disuse and glucocorticoid-induced atrophy," Med Sci Sports Exerc 22(3):304-311 (1990).
Amthor et al., "Lack of myostatin results in excessive muscle growth but impaired force generation," Proc Natl Acad Sci USA 104(6):1835-1840 (2007).
Ates, "The IGF-I splice variant MGF increases progenitor cells in ALS, dystrophic, and normal muscle," FEBS Lett 581:2727-2732 (2007).
Bach et al., "Alternative Splicing Produces Messenger RNAs Encoding Insulin-Like Growth Factor-I Prohormones that Are Differentially Glycosylated in Vitro," Mol Endocrinol 4(6):899-904 (1990).
Baehr et al., "Muscle sparing in muscle RING finger 1 null mice: response to synthetic glucocorticoids," J Physiol 589(Pt. 19):4759-4776 (2011).
Bailyes et al., "Insulin receptor/IGF-I receptor hybrids are widely distributed in mammalian tissues: quantification of individual receptor species by selective immunoprecipitation and immunoblotting," Biochem J 327:209-15 (1997).
Barton et al, "Deletion of muscle GRP94 impairs both muscle and body growth by inhibiting local IGF production," Faseb J 26:3691-3702 (2012).
Barton et al., "Muscle-specific expression of insulin-like growth factor I counters muscle decline in mdx mice," J Cell Biol 157:137-148 (2002).
Barton et al., "The insulin-like growth factor (IGF)-I E-peptides are required for isoform-specific gene expression and muscle hypertrophy after local IGF-I production," J Appl Physiol 108:1069-76 (2010).
Barton, "The ABCs of IGF-I isoforms: impact on muscle hypertrophy and implications for repair," Appl Physiol Nutr Metab 31:791-797 (2006).
Barton, "Viral expression of insulin-like growth factor-I isoforms promotes different responses in skeletal muscle," J Appl Physiol 100:1778-1784 (2006).
Barton-Davis et al., "Viral mediated expression of insulin-like growth factor I blocks the aging-related loss of skeletal muscle function," Proc Natl Acad Sci USA 95(26):15603-15607 (1998).
Brisson et al., "Insulin-like growth factor-I E-peptide activity is dependent on the IGF-I receptor," PLoS One 7(9):e45588 (2012).
Brooks et al., "Contractile properties of skeletal muscles from young, adult and aged mice," J Physiol 404:71-82 (1988).
Coleman et al., "Myogenic Vector Expression of Insulin-like Growth Factor I Stimulates Muscle Cell Differentiation and Myofiber Hypertrophy in Transgenic Mice," J Biol Chem 270(20):12109-12116 (1995).
Conover et al., "Cultured Human Fibroblasts Secrete Insulin-Like Growth Factor IA Prohormone," J Clin Endocrinol Metab 69(1):25-30 (1989).
Conover et al., "Human hepatoma cells synthesize and secrete insulin-like growth factor Ia prohormone under growth hormone control," Regul Pept 48:1-8 (1993).
Daniell et al., "Optimization of codon composition and regulatory elements for expression of human insulin like growth factor-1 in transgenic chloroplasts and evaluation of structural identity and function," BMC biotechnology 9:33 (2009).

(Continued)

*Primary Examiner* — Thomas S Heard
(74) *Attorney, Agent, or Firm* — Baker Botts L.L.P.

(57) ABSTRACT

The present disclosure provides for techniques using pro-IGF-I for increasing IGF-I activity. Accordingly, the present disclosure provides for compositions and methods for treating or preventing a disease or disorder mediated by IGF-I. In addition, the present disclosure provides for kits for use in the treatment or prevention of a disease or disorder mediated by IGF-I.

22 Claims, 21 Drawing Sheets
Specification includes a Sequence Listing.

(56) References Cited

OTHER PUBLICATIONS

Davoodi-Semiromi et al., "Chloroplast-derived vaccine antigens confer dual immunity against cholera and malaria by oral or injectable delivery," Plant biotechnology journal 8:223-42 (2010).
De Meyts et al., "Structural Biology of Insulin and IGF 1 Receptors: Implications for Drug Design," Nat Rev Drug Discov 1:769-783 (2002).
Deconinck et al., "Utrophin-Dystrophin-Deficient Mice as a Model for Duchenne Muscular Dystrophy," Cell 90: 717-27, (1997).
Denley et al., "Structural and Functional Characteristics of the Val44Met Insulin-Like Growth Factor I Missense Mutation: Correlation with Effects on Growth and Development," Mol Endocrinol 19(3):711-721 (2005).
Duguay et al., "Processing of Wild-type and Mutant Proinsulin-like Growth Factor-IA by Subtilisin-related Proprotein Convertases," J Biol Chem 272(10):6663-6670 (1997).
Durzynska et al., "The pro-Forms of Insulin-Like Growth Factor I (IGF-1) Are Predominant in Skeletal Muscle and Alter IGF-1 Receptor Activation," Endocrinology 154(3):1215-1224 (2013).
Federici et al., "Distribution of insulin/insulin-like growth factor-I hybrid receptors in human tissues," Mol Cell Endocrinol 129:121-126 (1997).
Fernandez et al., "Muscle-specific inactivation of the IGF-I receptor induces compensatory hyperplasia in skeletal muscle," J. Clin. Invest. 109:347-355 (2002).
Fernandez et al., "Functional inactivation of the IGF-I and insulin receptors in skeletal muscle causes type 2 diabetes," Genes & Dev 15:1926-1934 (2001).
Forbes et al., "Characteristics of binding of insulin-like growth factor (IGF)-I and IGF-II analogues to the type 1 IGF receptor determined by BIAcore analysis," Eur J Biochem 269:961-968 (2002).
Goldspink, "Loss of Muscle Strength During Aging Studied at the Gene Level," Rejuvenation Res 10(3):397-405 (2007).
Gregorevic et al., "Improved Contractile Function of the mdx Dystrophic Mouse Diaphragm Muscle after Insulin-Like Growth Factor-1 Administration," Am J Pathol 161(6):2263-72 (2002).
Hede et al., "E-Peptides Control Bioavailability of IGF-1," PLoS One 7(12):e51152 (2012).
Hill et al., "Expression and splicing of the insulin-like growth factor gene in rodent muscle is associated with muscle satellite (stem) cell activation following local tissue damage," J Physiol 549(Pt 2):409-418 (2003).
Kristensen et al., "Specificity of Insulin and Insulin-like Growth Factor I Receptors Investigated using Chimeric Mini-Receptors, Role of C-Terminal of Receptor αSubunit," J Biol Chem 274:37351-6 (1999).
Kwon et al., "Oral delivery of bioencapsulated exendin-4 expressed in chloroplasts lowers blood glucose level in mice and stimulates insulin secretion in beta-TC6 cells," Plant Biotechnology Journal 11:77-86 (2013).
Kwon et al., "Oral delivery of human biopharmaceuticals, autoantigens and vaccine antigens bioencapsulated in plant cells," Advanced Drug Delivery Reviews 65(6): 782-799 (2013).
Lefaucheur et al., "Phenotype of Dystrophinopathy in Old MDX Mice," Anat Rec 242:7076 (1995).
Liu et al., "Mice Carrying Null Mutations of the Genes Encoding Insulin-like Growth Factor I (Igf-1) and Type 1 IGF receptor (Igflr)," Cell 75:59-72 (1993).
Lynch et al., "IGF-I treatment improves the functional properties of fast- and slow-twitch skeletal muscles from dystrophic mice," Neuromuscul Disord 11:260-268 (2001).
McCarty, "Self-complementary AAV vectors; advances and applications," Mol Ther 16(10):1648-1656 (2008).
Metzger et al., "Separation of fast from slow anabolism by site-specific PEGylation of insulin-like growth factor I (IGF-I)," J Biol Chem 286(22):19501-19510 (2011).
Mills, "A Synthetic Mechano Growth Factor E Peptide Enhances Myogenic Precursor Cell Transplantation Success," Am J Transplant 7:2247-2259 (2007).
Moxley et al., "Practice Parameter: Corticosteroid treatment of Duchenne dystrophy: Report of the Quality Standards Subcommittee of the American Academy of Neurology and the Practice Committee of the Child Neurology Society," Neurology 64:13-20 (2005).
Musaro et al., "Localized IGF-1 transgene expression sustains hypertrophy and regeneration in senescent skeletal muscle," Nat Genet 27:195-200 (2001).
Pastoret et al., "mdx mice show progressive weakness and muscle deterioration with age," J Neurol Sci 129:97-105 (1995).
Pfeffer et al., "The Insulin-like Growth Factor (IGF)-I E-Peptides Modulate Cell Entry of the Mature IGF-I Protein," Mol Biol Cell 20(17):3810-3817 (2009).
Philippou et al., "Characterization of a Rabbit Antihuman Mechano Growth Factor (MGF) Polyclonal Antibody against the Last 24 Amino Acids of the E Domain," In Vivo 22:27-35 (2008).
Qaisar, "Is functional hypertrophy and specific force coupled with the addition of myonuclei at the single muscle fiber level?" Faseb J 26: 1077-1085 (2012).
Reitter, "Deflazacort vs. prednisone in Duchenne muscular dystrophy: trends of an ongoing study," Brain & Dev 17 Suppl: 39-43 (1995).
Ruhlman et al., "Expression of cholera toxin B-proinsulin fusion protein in lettuce and tobacco chloroplasts—oral administration protects against development of insulitis in nonobese diabetic mice," Plant Biotechnology Journal 5:495-510 (2007).
Ruhlman et al., "The role of Heterologous Chloroplast Sequence Elements in Transgene Integration and Expression," Plant Physiology 152:2088-2104 (2010).
Sicinski et al., "The Molecular Basis of Muscular Dystrophy in the mdx Mouse: A Point Mutation," Science 244:1578-80 (1989).
Stevens-Lapsley et al., "Impact of viral-mediated IGF-I gene transfer on skeletal muscle following cast immobilization," Am J Physiol Endocrinol Metab 299: E730-E740 (2010).
Vajdos et al., "Crystal Structure of Human Insulin-like Growth Factor-1: Detergent Binding Inhibits Binding Protein Interactions," Biochemistry 40:11022-9 (2001).
Verma et al., "Oral delivery of bioencapsulated coagulation factor IX prevents inhibitor formation and fatal anaphylaxis in hemophilia B mice," PNAS 107(15):7101-7106 (2010).
Wallis, "New insulin-like growth factor (IGF)-precursor sequences from mammalian genomes: the molecular evolution of IGFs and associated peptides in primates," Growth Horm IGF Res 19:12-23 (2009).
Wilson et al., "Monoclonal antibodies to the carboxy-terminal Ea sequence of pro-insulin-like growth factor-IA (proIGF-IA) recognize proIGF-IA secreted by IM9 B-lymphocytes," Growth Horm & IGF Res 11:10-17 (2001).
Yang, "Different roles of the IGF-I EC peptide (MGF) and mature IGF-I in myoblast proliferation and differentiation," FEBS Lett 522(1-3):156-160 (2002).
Yuasa, "Subtilisin-like Proprotein Convertase PACE4 is Required for Skeletal Muscle Differentiation," J Biochem 146:407-15 (2009).

* cited by examiner

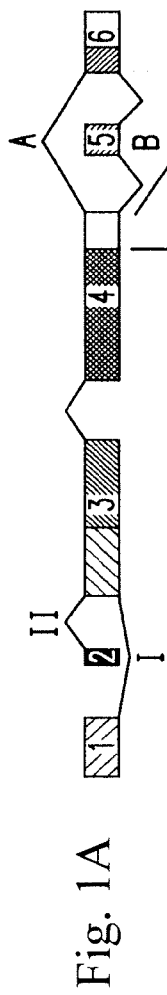
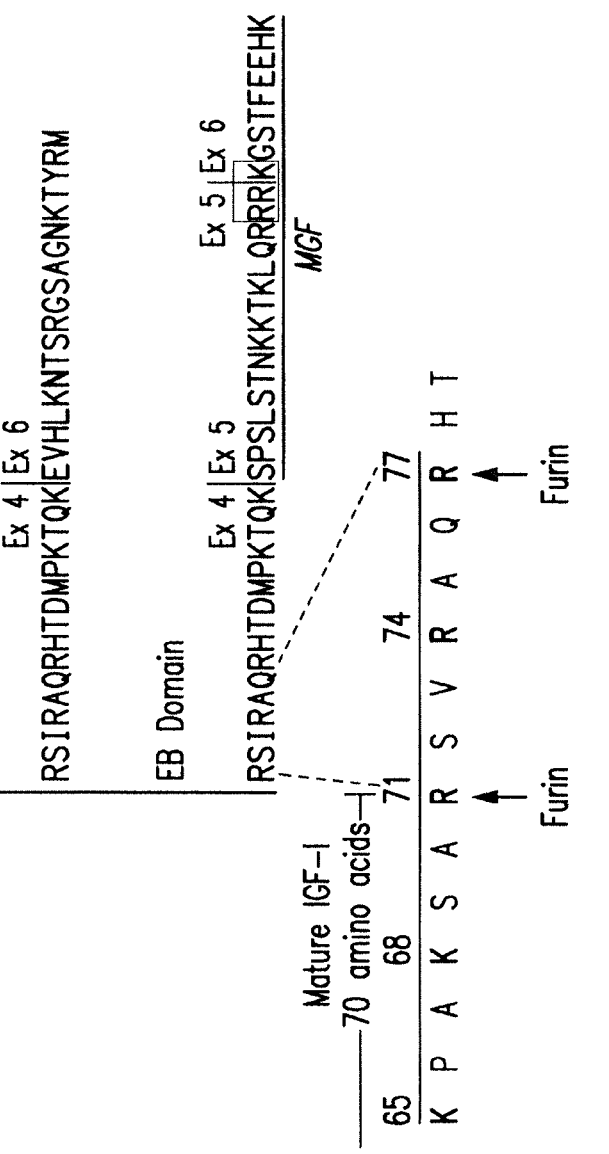
Fig. 1A
Fig. 1B
Fig. 1C

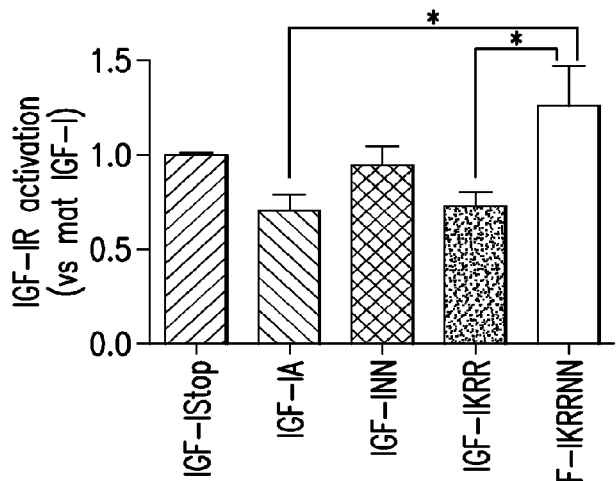
FIG. 5A
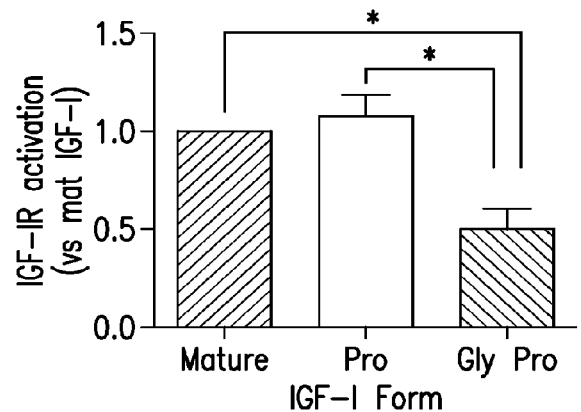
FIG. 5B
mgkisslptq lfkccfcdfl kvkmhtmsss hlfylalcll tftssatagp etlcgaelvd 61
alqfvcgdrg fyfnkptgyg sssrrapqtg ivdeccfrsc dlrrlemyca plkpaksars 121
vraqrhtdmp ktqkevhlkn asrgsagnkn yrm (SEQ ID NO: 1)
FIG. 6

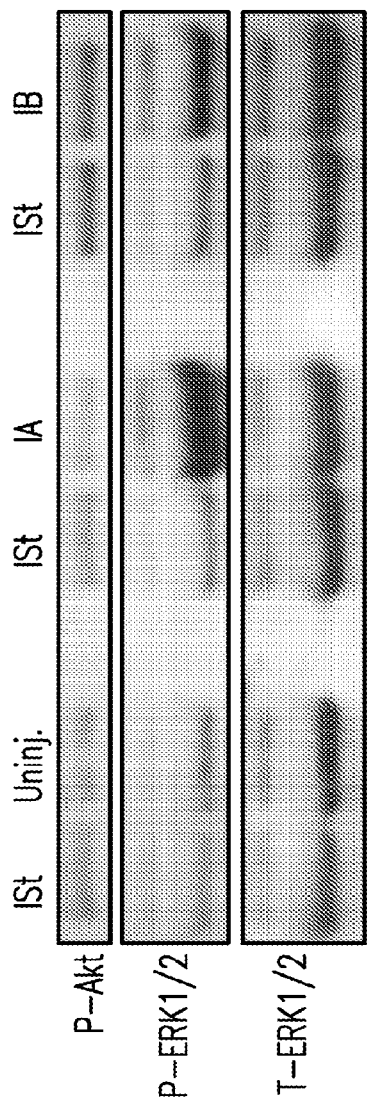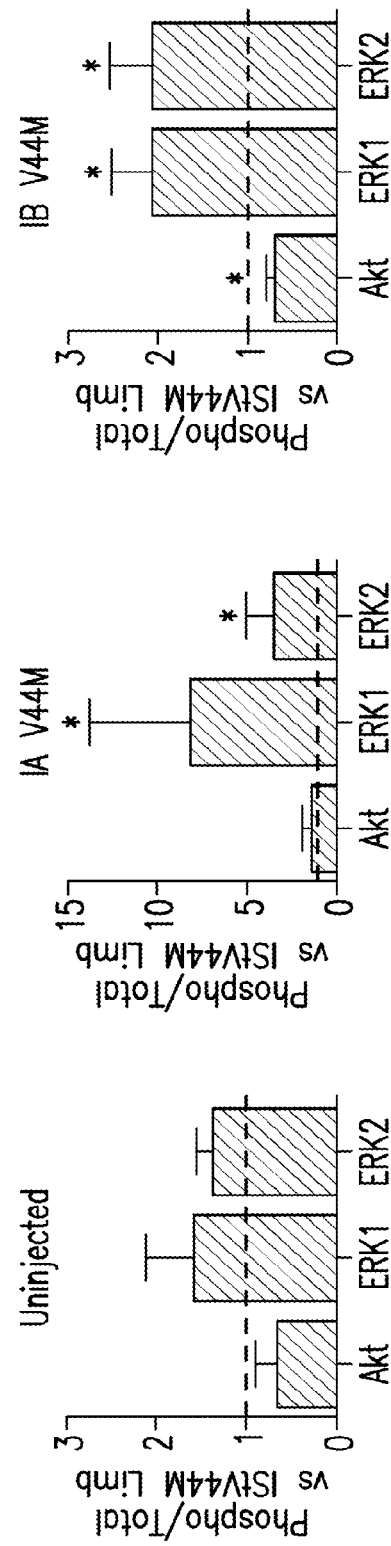

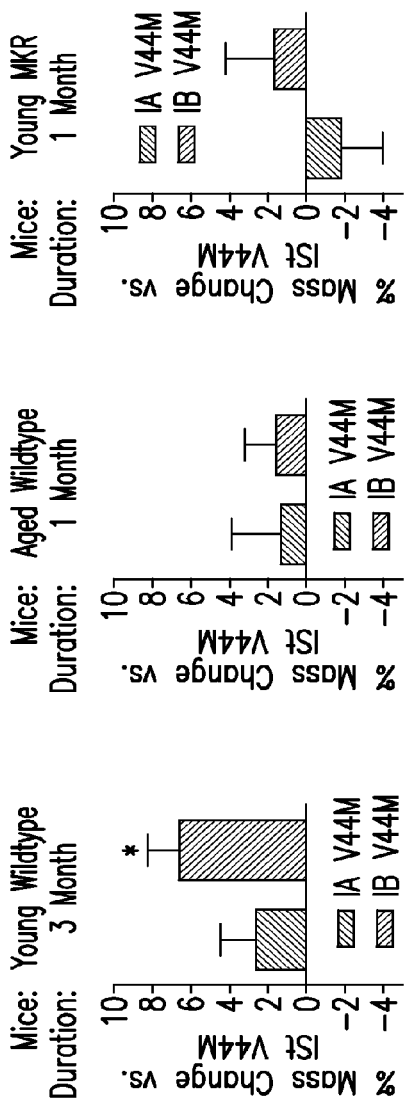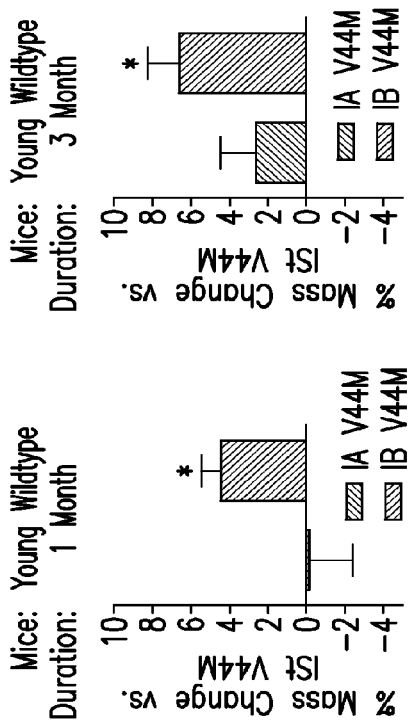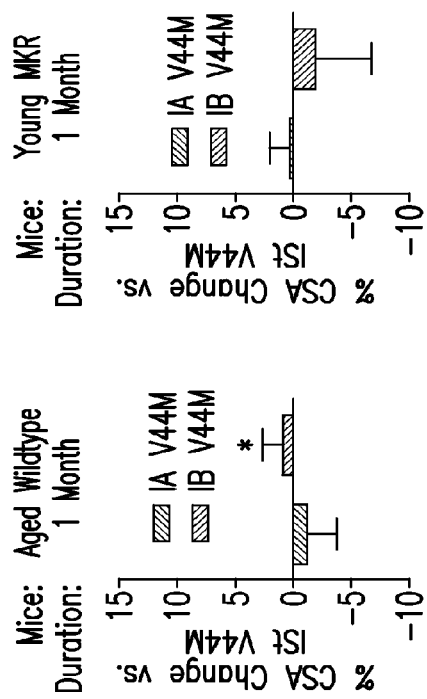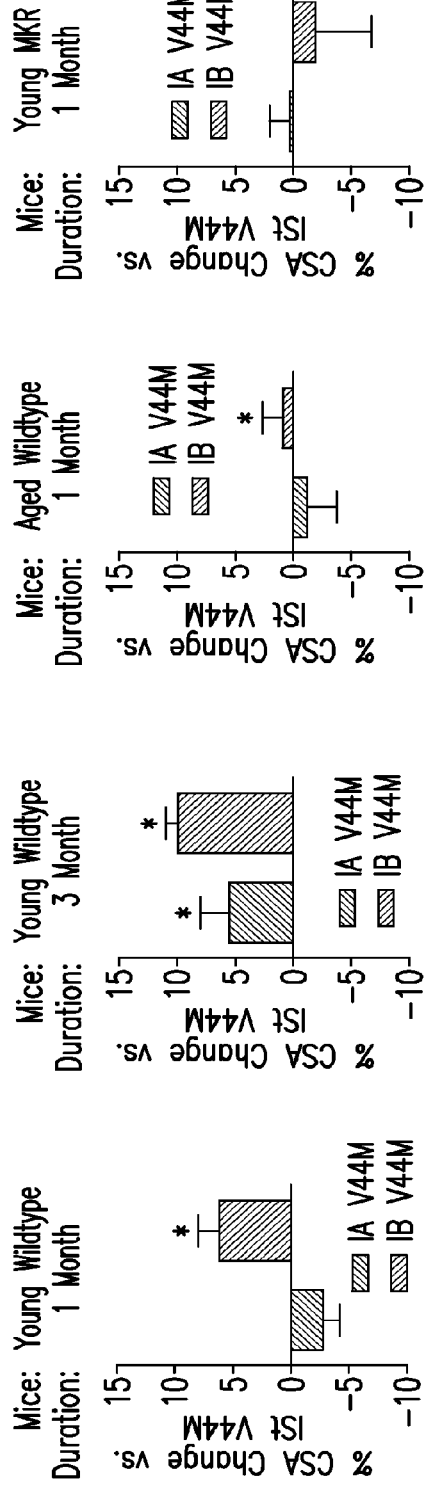
FIG. 10A  FIG. 10B  FIG. 10C  FIG. 10D
FIG. 10E  FIG. 10F  FIG. 10G  FIG. 10H

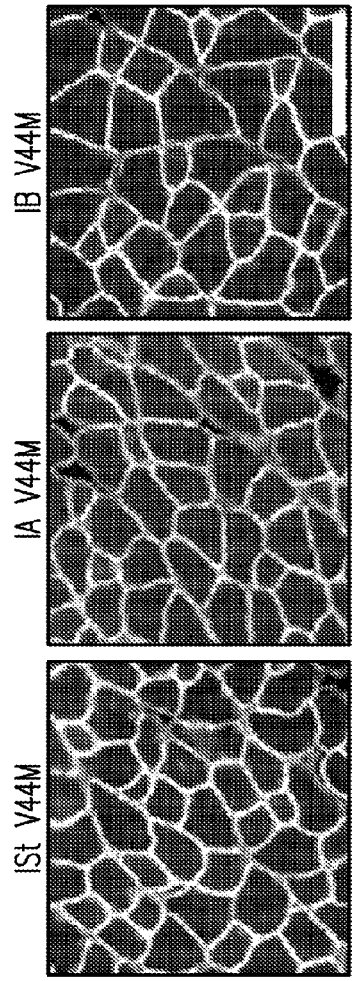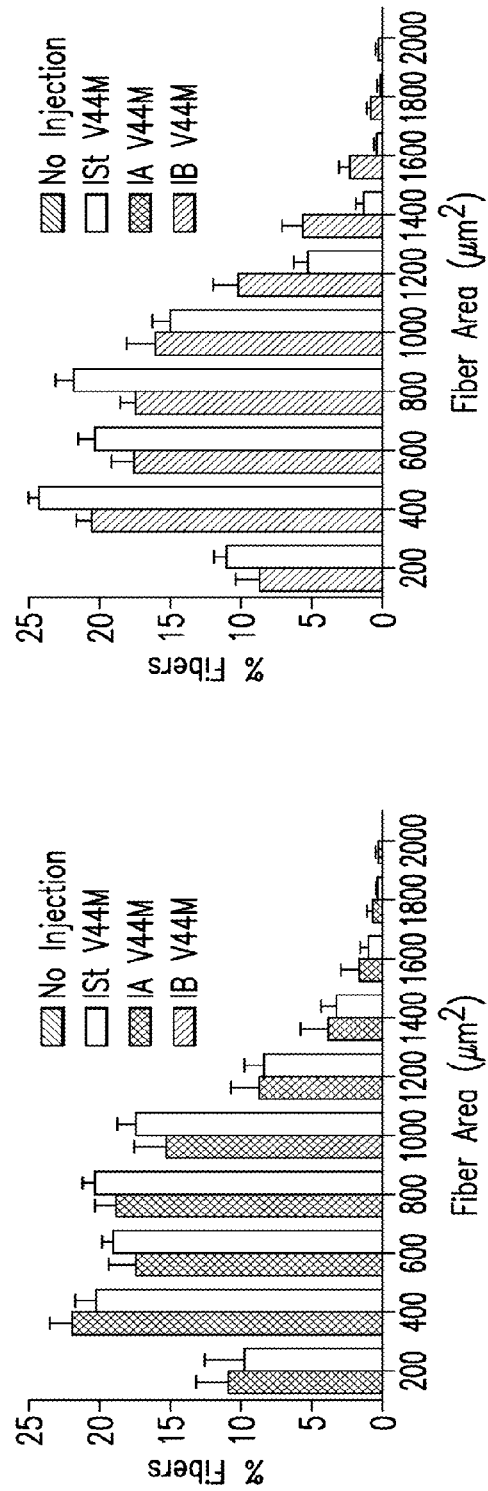
FIG. 11A
FIG. 11B
FIG. 11C

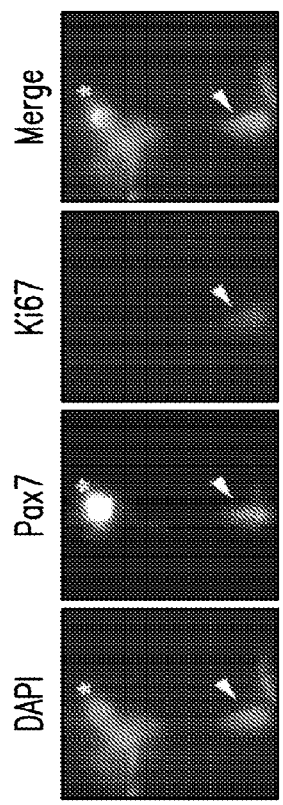
FIG. 12A
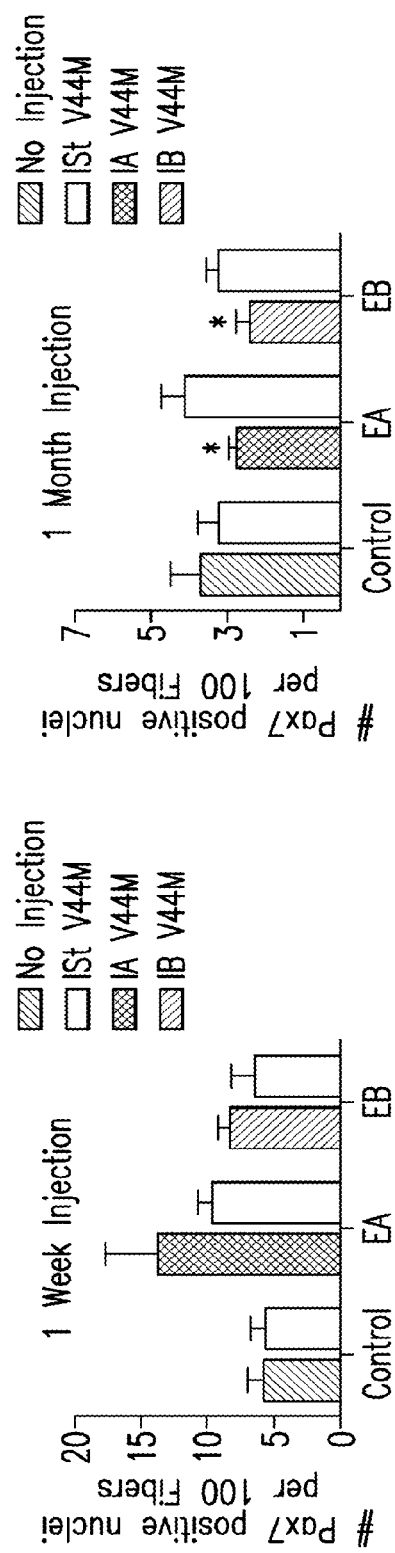
FIG. 12B
FIG. 12C

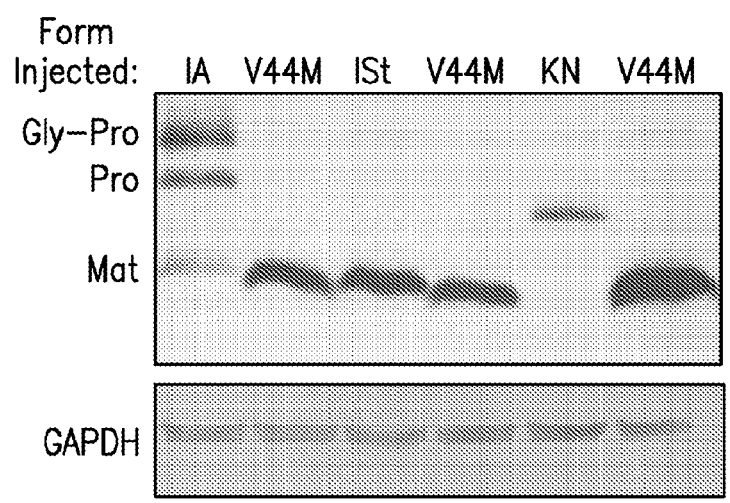
FIG. 15
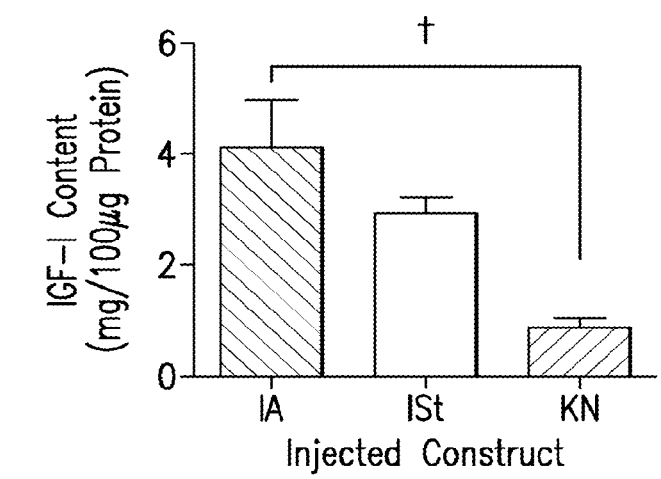
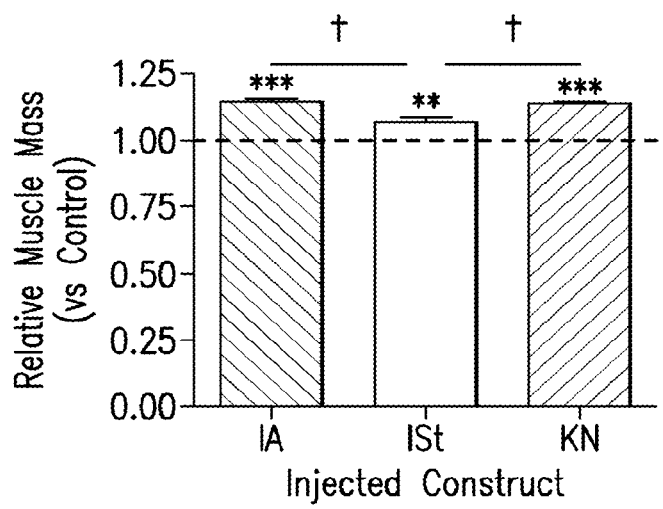
FIG. 16

SEQUENCE LISTING

```
<160> NUMBER OF SEQ ID NOS: 5

<210> SEQ ID NO 1
<211> LENGTH: 153
<212> TYPE: PRT
<213> ORGANISM: Homo sapiens

<400> SEQUENCE: 1

Met Gly Lys Ile Ser Ser Leu Pro Thr Gln Leu Phe Lys Cys Cys Phe
1               5                   10                  15

Cys Asp Phe Leu Lys Val Lys Met His Thr Met Ser Ser Ser His Leu
            20                  25                  30
```

-continued

```
Phe Tyr Leu Ala Leu Cys Leu Leu Thr Phe Thr Ser Ser Ala Thr Ala
             35                  40                  45

Gly Pro Glu Thr Leu Cys Gly Ala Glu Leu Val Asp Ala Leu Gln Phe
 50                  55                  60

Val Cys Gly Asp Arg Gly Phe Tyr Phe Asn Lys Pro Thr Gly Tyr Gly
 65                  70                  75                  80

Ser Ser Ser Arg Arg Ala Pro Gln Thr Gly Ile Val Asp Glu Cys Cys
                 85                  90                  95

Phe Arg Ser Cys Asp Leu Arg Arg Leu Glu Met Tyr Cys Ala Pro Leu
                100                 105                 110

Lys Pro Ala Lys Ser Ala Arg Ser Val Arg Ala Gln Arg His Thr Asp
            115                 120                 125

Met Pro Lys Thr Gln Lys Glu Val His Leu Lys Asn Ala Ser Arg Gly
    130                 135                 140

Ser Ala Gly Asn Lys Asn Tyr Arg Met
145                 150

<210> SEQ ID NO 2
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Any amino acid
<220> FEATURE:
<221> NAME/KEY: MOD_RES
<222> LOCATION: (5)..(6)
<223> OTHER INFORMATION: Any amino acid
<220> FEATURE:
<221> NAME/KEY: MOD_RES
<222> LOCATION: (8)..(9)
<223> OTHER INFORMATION: Any amino acid
<220> FEATURE:
<221> NAME/KEY: MOD_RES
<222> LOCATION: (11)..(12)
<223> OTHER INFORMATION: Any amino acid

<400> SEQUENCE: 2

Lys Xaa Xaa Lys Xaa Xaa Arg Xaa Xaa Arg Xaa Xaa Arg
 1               5                  10

<210> SEQ ID NO 3
<211> LENGTH: 35
<212> TYPE: PRT
<213> ORGANISM: Unknown
<220> FEATURE:
<223> OTHER INFORMATION: Description of Unknown: Rodent polypeptide

<400> SEQUENCE: 3

Arg Ser Ile Arg Ala Gln Arg His Thr Asp Met Pro Lys Thr Gln Lys
 1               5                  10                  15

Glu Val His Leu Lys Asn Thr Ser Arg Gly Ser Ala Gly Asn Lys Thr
                20                  25                  30

Tyr Arg Met
        35

<210> SEQ ID NO 4
<211> LENGTH: 41
<212> TYPE: PRT
<213> ORGANISM: Unknown
```

```
<220> FEATURE:
<223> OTHER INFORMATION: Description of Unknown: Rodent polypeptide

<400> SEQUENCE: 4

Arg Ser Ile Arg Ala Gln Arg His Thr Asp Met Pro Lys Thr Gln Lys
1               5                   10                  15

Ser Pro Ser Leu Ser Thr Asn Lys Lys Thr Lys Leu Gln Arg Arg Arg
                20                  25                  30

Lys Gly Ser Thr Phe Glu Glu His Lys
            35                  40

<210> SEQ ID NO 5
<211> LENGTH: 15
<212> TYPE: PRT
<213> ORGANISM: Homo sapiens

<400> SEQUENCE: 5

Lys Pro Ala Lys Ser Ala Arg Ser Val Arg Ala Gln Arg His Thr
1               5                   10                  15
```

IGF-1 PROTEINS AND THERAPEUTIC USES THEREOF

CROSS-REFERENCE TO RELATED APPLICATIONS

This application is a continuation of International Application No. PCT/US2013/050326, filed on Jul. 12, 2013, which claims priority to U.S. Provisional Application Ser. No. 61/671,489, filed on Jul. 13, 2012, and U.S. Provisional Application Ser. No. 61/680,424, filed on Aug. 7, 2012, each of which is incorporated herein by reference in their entireties.

STATEMENT OF GOVERNMENT INTEREST

This invention was made with government support under Grant No. AR057363 awarded by National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on May 16, 2016, is named 081406_0201_SEQLIST.txt and is 3,336 bytes in size.

BACKGROUND

The insulin-like growth factors (IGFs) constitute a family of proteins having insulin-like and growth stimulating properties. The IGFs show close structural homology with pro-insulin and elicit similar biological effects. The IGFs are circulating, mitogenic peptide hormones that have an important role in stimulating growth, differentiation, metabolism and regeneration both in vitro and in vivo.

IGF-I action can be essential for the regulation of tissue formation and remodeling, bone growth, prenatal growth, brain development, and muscle metabolism. Cellular effects of IGF-I are mediated through the IGF-I receptor, a transmembrane tyrosine kinase that phosphorylates intracellular substrates, resulting in the activation of multiple intracellular signaling cascades.

IGF-I can play a critical role in the growth and development of many tissues in the body. It is a key regulator of skeletal muscle development, and continues to enhance the ability for muscle to grow and undergo repair throughout life. In skeletal muscle, IGF-I coordinates with additional growth factors to promote myoblast proliferation, differentiation, and fiber formation during normal growth as well as during regeneration after injury. Increasing IGF-I levels can result in functional hypertrophy in young adult animals, maintenance of mass and regenerative capacity in senescent animals, and enhancement of muscle recovery to counter acute and chronic damage.

Thus, IGF-I can be a central therapeutic target for enhancing muscle function in aging and disease. Several strategies have been employed to boost IGF-I levels in muscle, including tissue-specific transgenic expression (1-3), viral-mediated gene transfer (4-8), and directed recombinant IGF-I delivery (7, 8). However, more effective techniques for increasing IGF-I levels are needed.

SUMMARY

In one aspect, the present disclosure provides methods for treating or preventing a disease or disorder mediated by IGF-I in a subject, e.g., a human subject, including administering to the subject a therapeutically effective amount of a pro-IGF-I protein, or functional portion thereof. In another aspect, the disclosure provides methods for treating or preventing a disease or disorder mediated by IGF-I in a subject or promoting muscle growth, including administering to the subject a therapeutic vector comprising a nucleic acid molecule encoding a pro-IGF-I protein or functional portion thereof. In certain embodiments, the disease or disorder mediated by IGF-I is loss of skeletal muscle function or growth. In certain embodiments, the disease or disorder mediated by IGF-I is muscle atrophy, disuse (such as in prolonged bed rest), dwarfism, Laron Syndrome, insulin-like growth factor-1 deficiency, idiopathic short stature, partial growth hormone insensitivity syndrome, Alzheimer's Disease, diabetes, renal insufficiency, amyotrophic lateral sclerosis, myocardial infarction, burn injury, muscular dystrophy, anorexia nervosa or cachexia, such as AIDS- or cancer-induced cachexia.

In certain embodiments, the pro-IGF-I protein or functional portion thereof is administered subcutaneously. In certain embodiments, the pro-IGF-I protein or functional portion thereof is administered in combination with a second therapeutic agent. In related embodiments, the therapeutic vector comprising a nucleic acid molecule encoding a pro-IGF-I protein or functional portion thereof is administered in combination with a second therapeutic agent.

Another aspect of the disclosure provides a pharmaceutical composition comprising a pro-IGF-I protein or functional portion thereof and a pharmaceutically acceptable carrier. In certain embodiments, the pharmaceutical composition comprises at least one of a pharmaceutically acceptable diluent, carrier, solubilizer, emulsifier, preservative, and adjuvant. The present disclosure also provides kits comprising a container for the pharmaceutical composition, and instructions for use.

BRIEF DESCRIPTION OF THE DRAWINGS

FIG. 1A-1C: Alternative splicing of the igf1 gene results in two isoforms in rodents that are highly conserved in humans. A. IGF-IA skips exon 5, whereas IGF-IB retains exon 5 resulting in a frame shift and a shortened sequence of exon 6. B. The C-terminal sequences (SEQ ID NOS 3-4, respectively, in order of appearance) of these isoforms bear only ~50% homology. EA domain contains putative glycosylation sites, and EB has a potential protease cleavage site. C. ProIGF-I processing sites that are cleaved by protease furin are depicted by arrows (Adapted from Barton, 2006 and Duguay et al., 1995) (SEQ ID NO: 5).

FIG. 5A-5B. A. KIRA assay IGF-IR phosphorylation levels by IGF-I in enriched media. Results are normalized to mature IGF-I activation within each KIRA experiment, where each sample was measured in triplicate. Data shown is mean±SEM for 4 experiments. B. Calculated contribution of mature IGF-I, pro-IGF-I, and gly-pro-IGF-I to IGF-I receptor activation. Pro-IGF-I displays equivalent activation of the receptor compared to mature IGF-I, whereas gly-pro-IGF-I has a significantly reduced ability to activate the IGF-I receptor. *, $P<0.05$ for comparisons between conditions.

FIG. 6. An exemplary human IGF-I protein, GenBank Accession No. GI:11024682, including the C-terminal E-peptide extension at amino acids 119-153 and the mature IGF-I protein at amino acids 49-118.

FIG. 9A-9D. E-peptides affect muscle signaling. A. Mouse hindlimbs were treated with either IA V44M or IB V44M AAV injections, or uninjected (Uninj.) in one limb, with ISt V44M injected in the contralateral limb. TA lysates were immunoblotted for phosphorylated and total ERK1/2 (P-ERK, T-ERK) and AKT (P-Akt, Total Akt not shown). B-D. The intensities of phosphorylated bands were normalized to total bands, and then compared to the ISt V44M control limb. Bars represent means±s.e.m. of N=3-4 mice per test injection. *, $p<0.05$, for comparisons to ISt V44M control limbs via paired t-tests.

FIG. 10A-10L. IA and IB V44M expression affects muscle size and strength. The AAV IA or IB V44M EDLs were compared to IS V44M control EDLs. The percent change in mass (A-D), CSA (E-H), and Specific Force (I-L) is graphed. Young (2-3 week old) wildtype C57 mice dissected 1 (A, E, I) and 3 (B, F, J) months after injection; Aged (1 year old) wildtype mice dissected 1 month after injection (C, G, K); MKR mice which do not express functional IGF-I in skeletal muscle, dissected 1 month after injection (D, H, L). Bars represent means±s.e.m. of N=4-8 EDL muscle pairs per injection. *, p<0.05, for comparisons to ISt V44M contralateral control EDLs via paired t-tests.

FIG. 11A-11F. Fiber area increased after AAV D3 V44M injection. A. Sections of AAV V44M injected EDLs were stained for dystrophin to outline muscle fibers. Scale bar=65 µm. B-C. The areas of all the fibers in the EDLs (~1000 fibers on average per EDL) were measured and histograms were generated representing the proportion of fibers at a certain size. D. The percent change in average fiber area compared to ISt V44M control limbs. Bars represent means±s.e.m. of N=5 EDL muscle pairs per vector. *, p<0.05, for comparisons to ISt V44M contralateral control EDLs via paired t-tests. E. MHC-specific antibodies were used to label I/β, 2A, and 2B fibers in D3 V44M injected and contralateral ISt V44M injected control EDLs. The average fiber area of total fibers, and of each fiber-type are graphed. Bars represent means±s.e.m. of N=5 EDL muscle pairs. *, p<0.05, for comparisons to ISt V44M contralateral control EDLs via paired t-tests. F. Mice injected with AAV IB and ISt V44M for 1 month were treated with Dexamethasone (DEX) or not treated (NoTx) for 2 weeks before dissection to cause atrophy. Bars represent means±s.e.m. of N=5-6 EDL muscle pairs. †, p<0.05 or ns, not significant, for comparisons to ISt V44M contralateral control EDLs via paired t-tests. *, p<0.05, for comparisons to NoTx via unpaired t-test.

FIG. 12A-12G. E-peptides affect satellite cell number and proliferation. A. Nuclei (DAPI, blue), satellite cell nuclei (Pax7, green), and proliferating nuclei (Ki67, red) were labeled in AAV IA, IB, and ISt V44M injected EDL muscle sections.*, non-proliferating and ▶, proliferating satellite cell nuclei. B-G. The number of Pax7 positive nuclei (B-D) and both Pax7 and Ki67 positive nuclei (e-g) were counted per 100 fibers in mice injected with AAV V44M for 1 week (B and E), 1 month (C and F), and 3 months (D and G). Bars represent means±s.e.m. of N=4-6 EDL muscle pairs per vector tested. *, p<0.05, for comparisons to ISt V44M contralateral control EDLs via paired t-tests.

FIG. 15. Immunoblot of IGF-I produced by AAV injection. IA, IGF-IA; ISt, mature IGF-I; KN, pro-IGF-I; V44M, IGF-I with a V44M mutation. Blot with GAPDH serves as loading control.

FIG. 16. Upper panel, IGF-I content quantified from immunoblots (N=3 per condition). Lower panel, change in muscle mass after AAV injections. †, significant difference between conditions; *, significant difference vs. control limb; by 1-way ANOVA followed by Tukey post hoc comparison.

DETAILED DESCRIPTION

Figure 2A:
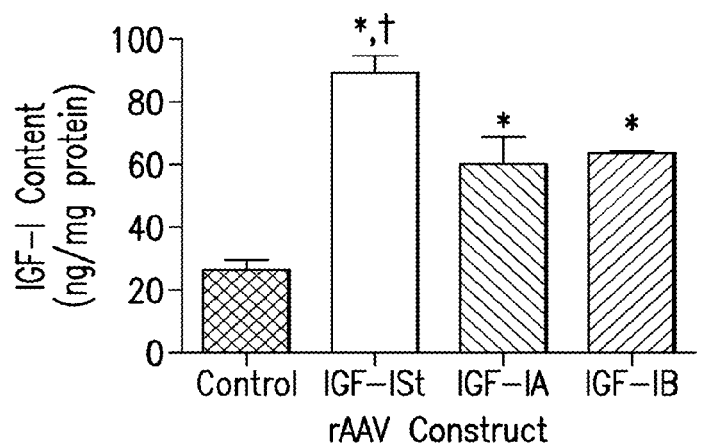
FIG. 2A-2F. Viral delivery of IGF-I isoforms increases IGF-I content in muscle and produces multiple forms of IGF-I protein. A. ELISA measurements demonstrate a 3-4 fold increase in IGF-I content following viral delivery to murine skeletal muscle. Comparison of IGF-I production shows that IGF-ISt has the highest apparent IGF-I levels in lysates from injected muscles. Results are shown as mean±SEM for N=4 muscles per condition. *, P<0.05 injected vs. control samples, †, P<0.05, comparisons of injected samples. Immunoblotting for mature IGF-I (panel B), EA peptide (panel C), and EB peptide (panel D), show that IGF-IA production results in 2 pro-IGF-I forms, with little detectable mature IGF-I. Similarly, IGF-IB production results in predominantly pro-IGF-I. Only mature IGF-I is produced after viral delivery of IGF-ISt, and IGF-I levels are below the level of detection in control uninjected muscle lysates. Total protein was 80 µg for panels B-D. E. Schematic of alternative splicing of the Igf1 gene and the forms of IGF-I produced by the viral constructs, with the recognition sites for all antibodies indicated. F. Immunoblotting shows the endogenous IGF-I forms in muscle (Mus). IGF-I forms are evident only upon long exposure for anti-IGF-I, and reveal a mature IGF-I band at ~8 kD, as well as multiple bands between 14 and 28 kD. Compared to the IGF-I standard, the levels of IGF-I found in muscle are in the picogram range. Additional blotting with anti-EA show that 2 bands (17 and 25 kD) are detectable with antibodies for EA and IGF-I. A total of 100 µg muscle protein was utilized for immunoblots. 0.5 ng recombinant murine IGF-I (rIGF-I), and 20 ng recombinant EA peptide were used as positive controls. Lefthand lane (Coom) shows coomassie stained lane of gel containing muscle lysate.

IGF-I is produced from the Igf1 gene, which is >90% conserved across species, and can undergo alternative splicing at both the 5' and 3' ends to generate multiple isoforms (FIG. 2E) (reviewed in (9)). Regardless of the isoform transcribed, a pre-pro-peptide is translated, which consists of a signal peptide directing secretion, the mature IGF-I peptide, and a C-terminal extension, called the E-peptide. Following cleavage of the signal peptide, the pro-IGF-I (mature IGF-I plus an E-peptide) can be subjected to additional processing prior to secretion. This includes cleavage of the E-peptide by intracellular proteases to release mature IGF-I for secretion (10), maintenance of pro-IGF-I to be secreted without cleavage (11-13), or N-glycosylation in the E-peptide of the predominant IGF-I isoform (IGF-IA) (14), and secretion (termed Gly-Pro-IGF-I). Hence, three forms of IGF-I protein exist in the extracellular milieu: mature IGF-I, pro-IGF-I, and Gly-Pro-IGF-I.

IGF-I acts predominantly via the IGF-I receptor (IGF-IR) as well as the hybrid receptors formed by insulin and IGF-I receptor heterodimers (15, 16). It also activates the insulin receptor to a lesser extent with approximately 10 fold lower affinity than insulin (17). Through the inherent tyrosine kinase activity of these receptors, ligand binding mediates the signaling pathways necessary for cell survival and growth. It has been generally believed that the mature IGF-I is the obligate ligand for these receptors, and that the pro IGF forms are precursors that must have the C-terminus removed before efficient receptor binding can occur. The residues that are important for receptor binding are distributed throughout the mature molecule (18, 19) and none have previously been identified in the E peptide C-terminal extension, supporting that it is dispensable for receptor binding. However, PEGylated mature IGF-I protein (20) demonstrate that high molecular weight modifications at Lysine 68 near to the C-terminus of mature IGF-I do not inhibit IGF-I receptor activation, and also increase the half-life of the growth factor.

The disclosed subject matter establishes that much of the IGF-I in muscle is pro-IGF-I, which retains an E-peptide. For IGF-IA, the major isoform of IGF-I, the E peptide can be glycosylated, leading to two longer IGF-I forms, non-glycosylated pro-IGF-I, which has a non-glycosylated E-peptide, and glycosylated pro-IGF-I, which has a glycosylated E-peptide. The disclosed subject matter establishes that skeletal muscles have roughly equivalent levels of glycosylated and non-glycosylated pro-IGF-I. Further, non-glycosylated pro-IGF-I is more efficient at IGF-IR activation than mature IGF-I form. Thus, as described herein, the non-glycosylated E-peptide found in pro-IGF-I does not inhibit ligand-receptor interactions. In addition, the glycosylated E-peptide found on glycosylated pro-IGF-I may serve a role similar the PEG group of PEGylated mature IGF-I, in improving stability of the growth factor.

Accordingly, the disclosed subject matter provides techniques using pro-IGF-I which includes an E-peptide, for increasing IGF-I activity in vivo (IGF-I activity includes, e.g., activating the IGF-I receptor (IGF-IR)). Therefore, by administering pro-IGF-I to a subject in need thereof, IGF-I activity is improved. In certain embodiments, the disclosed subject matter provides techniques using the E-peptide, or functional portions thereof, for increasing IGF-I activity in vivo.

In one aspect, the present disclosure relates to treatment of a subject in vivo using a pro-IGF-I protein such that an IGF-I mediated disease or disorder is treated or prevented. In certain embodiments, a pro-IGF-I protein of the disclosure can be used alone to inhibit or to treat IGF-I mediated diseases or disorders. In certain embodiments, a pro-IGF-I protein of the disclosure can be used in conjunction with other therapeutic agents, such as growth hormones (e.g., rhGH), for the treatment or prevention of IGF-I mediated diseases or disorders.

Accordingly, in certain embodiments, the disclosure provides a method of treating or preventing an IGF-I mediated disease or disorder in a subject, including administering to the subject a therapeutically effective amount of a pro-IGF-I protein of the disclosure. In certain embodiments, the administration of a pro-IGF-I protein can be beneficial in improving muscle mass, strength, and repair.

An IGF-I mediated disease or disorder can refer to any disease or disorder that is caused by or related to a deficiency in activity or level of IGF-I, including loss of skeletal muscle function or growth, diseases or disorders which would benefit from increased IGF-I levels or activity, or diseases or disorders characterized by dysregulation of the GH/IGF axis. Such disorders are characterized by defects in growth, physiology, and/or glycemic control. In certain embodiments, an IGF-I mediated disease or disorder can refer to any disease or disorder whose symptoms would benefit from increased IGF-I levels or activity. IGF-I mediated diseases or disorders include, but are not limited to, muscle atrophy, disuse (such as in prolonged bed rest), dwarfism, Laron Syndrome, insulin-like growth factor-1 deficiency, idiopathic short stature, partial growth hormone insensitivity syndrome, Alzheimer's Disease, diabetes, renal insufficiency, amyotrophic lateral sclerosis, myocardial infarction, burn injury, muscular dystrophy, anorexia nervosa or cachexia, such as AIDS- or cancer-induced cachexia.

"Insulin-like Growth Factor-I" or "IGF-I" is also referred to as somatomedin-C. The mature human IGF-I peptide is a single chain 70 amino acid protein. The human protein has a 195 amino acid precursor, which includes the E-peptide (see, for example, GenBank Accession Nos. GI:11024682 or GI:156229709; FIG. 6). In the human protein represented by GI:11024682 or GI:156229709, amino acids 49-118 are the mature IGF-I protein, and amino acids 119-153 include the E-peptide.

In certain embodiments, a pro-IGF-I protein or peptide can include an IGF-I protein that contains an E-peptide, or a functional portion thereof. A pro-IGF-I protein or peptide can include a peptide that is substantially similar to a naturally occurring pro-IGF-I protein or peptide, or an analogue, variant, derivative or mimetic of a naturally occurring pro-IGF-I protein or peptide, which is capable of activating IGF-IR in vivo, resulting in improved IGF-I level or activity. The "E-peptide" portion of the pro-IGF-I protein can be an E-peptide that is substantially similar to a naturally occurring E-peptide, a variant, analogue, derivative or mimetic thereof. The pro-IGF-I protein or peptide can also contain a different C-terminal peptide or another C-terminal modification in addition to or in place of a naturally occurring E-peptide, which results in an IGF-I protein that is capable of activating IGF-IR in vivo, resulting in improved or an increase in IGF-I level or activity.

In certain embodiments, if referring to exogenous administration, the pro-IGF-I protein or peptide can be from any source, whether natural, synthetic, or recombinant. In certain embodiments, the pro-IGF-I protein or peptide or the pro-IGF-I nucleic acid can be from any species, including bovine, ovine, porcine, equine, avian, and human. For example, the pro-IGF-I protein or peptide can be generated by recombinant nucleic acid technology in bacteria. In certain embodiments, the pro-IGF-I protein or peptide can be generated by recombinant nucleic acid technology in chloroplasts (see, e.g., U.S. Patent Application No. 2007/0124838). In certain embodiments, the pro-IGF-I protein or peptide can be generated by viral-mediated gene transduction.

As used herein, "treatment" or "treating" refers to inhibiting the progression of a disease or disorder, or delaying the onset of a disease or disorder, whether physically, e.g., stabilization of a discernible symptom, physiologically, e.g., stabilization of a physical parameter, or both. As used herein, the terms "treatment," "treating," and the like, refer to obtaining a desired pharmacologic and/or physiologic effect. The effect may be prophylactic in terms of completely or partially preventing a disease or condition, or a symptom thereof and/or may be therapeutic in terms of a partial or complete cure for a disease or disorder and/or adverse affect attributable to the disease or disorder. "Treatment," as used herein, covers any treatment of a disease or disorder in an animal or mammal, such as a human, and includes: decreasing the risk of death due to the disease; preventing the disease of disorder from occurring in a subject which may be predisposed to the disease but has not yet been diagnosed as having it; inhibiting the disease or disorder, i.e., arresting its development (e.g., reducing the rate of disease progression); and relieving the disease, i.e., causing regression of the disease.

As used herein, the term "subject" includes any human or nonhuman animal. The term "nonhuman animal" includes, but is not limited to, all vertebrates, e.g., mammals and non-mammals, such as nonhuman primates, sheep, dogs, cats, horses, cows, chickens, amphibians, reptiles, etc. In certain embodiments, the subject is a pediatric patient. In certain embodiments, the subject is an adult patient.

Various aspects of this disclosure are described in further detail in the following subsections.

Proteins of this Disclosure

In addition to proteins that include an amino acid sequence that is identical to the human pro-IGF-I proteins described herein, this disclosure also encompasses pro-IGF-I proteins that are "substantially similar" thereto, including pro-IGF-I proteins which include an E-peptide that is substantially similar to the endogenous human E-peptide. Proteins described herein as being "substantially similar" to a reference protein, such as the native human pro-IGF-I protein, include proteins that retain certain structural and functional features of the native proteins yet differ from the native amino acid sequence at one or more amino acid positions (i.e., by amino acid substitutions). In certain embodiments, this disclosure encompasses E-peptide proteins or peptides that are "substantially similar" thereto, including an E-peptide that is substantially similar to the endogenous human E-peptide.

In certain embodiments, proteins altered from the native sequence can be prepared by substituting amino acid residues within a native protein and selecting proteins with the desired activity. For example, amino acid residues of a pro-IGF-I protein (including the E-peptide portion thereof), can be systematically substituted with other residues and the substituted proteins can then be tested in standard assays for evaluating the effects of such substitutions on the ability of the protein to increase levels or activity of IGF-I and/or treat or prevent IGF-I mediated diseases or disorders.

In certain embodiments, to retain functional activity, conservative amino acid substitutions can be made. As used herein, the term a "conservative amino acid substitution" can include a substitution in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), β-branched side chains (e.g., threonine, valine, isoleucine) and aromatic side chains (e.g., tyrosine, phenylalanine, tryptophan, histidine). In certain embodiments, amino acid substitutions can include replacement of an amino acid residue with another residue having a small side chain, such as alanine or glycine. Amino acid substituted peptides can be prepared by standard techniques, such as automated chemical synthesis, as described further below.

In certain embodiments, a pro-IGF-I protein of the present disclosure is at least about 70%, 71%, 72%, 73%, 74%, 75%, 76%, 77%, 78%, 79%, 80%, 81%, 82%, 83%, 84%, 85%, 86%, 87%, 88%, 89% 90%, 91%, 92%, 93%, 94%, 95%, 96%, 97%, 98%, or 99%, homologous to the amino acid sequence of a pro-IGF-I protein described herein or known in the art.

As used herein, the percent homology between two amino acid sequences is equivalent to the percent identity between the two sequences. The percent identity between the two sequences is a function of the number of identical positions shared by the sequences (i.e., % homology=# of identical positions/total # of positions×100), taking into account the number of gaps, and the length of each gap, which should be introduced for improved alignment of the two sequences. The comparison of sequences and determination of percent identity between two sequences can be accomplished using a mathematical algorithm, as described in the non-limiting examples below.

In certain embodiments, the percent identity between two amino acid sequences can be determined using the algorithm of E. Meyers and W. Miller (*Comput. Appl. Biosci.*, 4:11-17 (1988)) which has been incorporated into the ALIGN program (version 2.0), using a PAM120 weight residue table, a gap length penalty of 12 and a gap penalty of 4. In certain embodiments, the percent identity between two amino acid sequences can be determined using the Needleman and Wunsch (*J. Mol. Biol.* 48:444-453 (1970)) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6.

In certain embodiments, the protein sequences of the present disclosure can further be used as a "query sequence" to perform a search against public databases, for example, to identify related sequences. Such searches can be performed using the XBLAST program (version 2.0) of Altschul, et al. (1990) *J. Mol. Biol.* 215:403-10. BLAST protein searches can be performed with the XBLAST program, score=50, wordlength=3 to obtain amino acid sequences homologous to the antibody molecules of this disclosure. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., XBLAST and NBLAST) are useful. See the National Center for Biotechnology Information (NCBI) website.

In certain embodiments, the pro-IGF-I proteins of the disclosure can be prepared by any suitable method for protein synthesis, including chemical synthesis and recombinant DNA technology. Methods for chemically synthesizing peptides are well known in the art (see e.g., Bodansky, M. Principles of Peptide Synthesis, Springer Verlag, Berlin (1993) and Grant, G. A (ed.). Synthetic Peptides: A User's Guide, W. H. Freeman and Company, New York (1992). Automated peptide synthesizers are commercially available (e.g., Advanced ChemTech Model 396; Milligen/Biosearch 9600). Methods for preparing proteins by recombinant expression in a host cell of DNA encoding the peptide are also well known in the art (see e.g., Sambrook et al. (1989) Molecular Cloning: A Laboratory Manual, 2nd Edition, Cold Spring Harbor Laboratory Press).

In addition to amino acid-substituted proteins, the disclosure also encompasses pro-IGF-I proteins having other modifications. In certain embodiments, the amino-terminus or carboxy-terminus of the protein can be modified, including the E-peptide. In certain embodiments, the pro-IGF-I protein or peptide of the present disclosure can have an amino-derivative group. An amino-derivative group can include amino-terminal modifications of the peptide compounds of this disclosure. In certain embodiments, N-terminal modifications can include alkyl, cycloalkyl, aryl, arylalkyl, and acyl groups. In certain embodiments, the N-terminal modification is acetylation.

In certain embodiments, the pro-IGF-I protein or peptide of the present disclosure can have a carboxy-derivative group. A carboxy-derivative group can include carboxy-terminal modifications of the peptide compounds of the disclosure. Examples of modifications of the C-terminus include modification of the carbonyl carbon of the C-terminal residue to form a carboxyterminal amide or alcohol (i.e., as reduced form). In general, the amide nitrogen, covalently bound to the carbonyl carbon on the C-terminal residue, will have two substitution groups, each of which can be hydrogen, alkyl or an alkylaryl group (substituted or unsubstituted). In certain embodiments, the C-terminal can be an amido group, such as $-CONH_2$, $-CONHCH_3$, $-CONHCH_2C_6H_5$ or $-CON(CH_3)_2$. In certain embodiments, the C-terminal can be 2-, 3-, or 4-pyridylmethyl, 2-, 3-, or 4-pyridylethyl, carboxylic acid, ethers, carbonyl esters, alkyl, arylalkyl, aryl, cyclohexylamide, piperidineamide and other mono or disubstituted amides. Other moieties that can be linked to the C-terminal residue include piperidine-4-carboxylic acid or amide and cis- or trans-4-amino-cyclohexa-necarboxylic acid or amide.

In certain embodiments, the modification of one or more side chains of non-critical amino acid residues (e.g., "neutral" residues) can be tolerated without altering the function of the protein. A covalent modification of an amino acid side chain or terminal residue can be introduced into the peptide by reacting targeted amino acid residues of the peptide with an organic derivative agent that is capable of reacting with selected side chains or terminal residues. Non-limiting examples of side chain modifications are described further below.

Cysteinyl residues can be reacted with α-haloacetates (and corresponding amines), such as chloroacetic acid or chloroacetamide, to give carboxymethyl or carboxyamidomethyl derivatives. Cysteinyl residues can be derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloro-mercuribenzoate, 2-chloromercuri-4-nitrophenol, or chloro-7-nitrobenzo-2-oxa-1,3-diazole. Cysteinyl residues can also react with nitric oxide generating three potential derivatives, sulphenic (SOH), sulphinic ($SO_2^-$) and sulphonic ($SO_3^-$), with progressively increasing chemical stability, the last one representing an irreversible change. Such derivatives can occur in vivo and can also be synthesized in vitro (Hess et al., (2005) *Nat Rev Mol Cell Biol.* 6:150-66).

Histidyl residues can be derivatized by reaction with diethylpyrocarbonate at pH 5.5-7.0 because this agent is relatively specific for the histidyl side chain. Parabromophenacyl bromide can be used; the reaction can be performed in 0.1 M sodium cacodylate at pH 6.0.

Lysinyl and amino terminal residues can be reacted with succinic or other carboxylic acid anhydrides. Derivatization with these agents has the effect of reversing the charge of the lysinyl residues. Other suitable reagents for derivatizing α-amino-containing residues include, but are not limited to, imodoesters such as methyl picolinimidate; pyridoxal phosphate; pyridoxal; chloroborohydride; trinitobenzenesulfonic acid; O-methylisourea; 2,4-pentanedione; and transaminase-catalyzed reaction with glyoxylate.

Arginyl residues can be modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents can react with the groups of lysine as well as the arginine epsilon-amino groups.

The specific modification of tyrosyl residues per se has been studied extensively, with particular interest in introducing spectral labels into tyrosyl residues by reaction with aromatic diazonium compounds or tetranitromethane. N-acetylimidizol and tetranitromethane can be used to form O-acetyl tyrosyl species and 3-nitro derivatives, respectively. Tyrosyl residues can be iodinated using $^{125}I$ or $^{131}I$ to prepare labeled proteins for use in radioimmunoassay, the chloramine T method described above being suitable.

Carboxyl side groups (aspartyl or glutamyl) can be selectively modified by reaction with carbodiimides (R'—N═C═N—R') such as 1-cyclohexyl-3-(2-morpholinyl-(4-ethyl) carbodiimide or 1-ethyl-3-(4-azonia-4,4-demethylpentyl) carbodiimide. Furthermore, aspartyl and glutamyl residues can be converted to asparaginyl and glutaminyl residues by reaction with ammonium ions.

Glutaminyl and asparaginyl residues can be deamidated to the corresponding glutamyl and aspartyl residues. Alternatively, these residues can be deamidated under mildly acidic conditions. Either form of these residues falls within the scope of this disclosure.

Other modifications encompassed by the present disclosure, include, but are not limited to, hydroxylation of proline and lysine, phosphorylation of hydroxyl groups of seryl or threonyl residues, methylation of the a-amino groups of lysine, arginine, and histidine side chains (T. E. Creighton (1983) Proteins: Structure and Molecular Properties, W. H. Freeman & Co., San Francisco, pp. 79-86).

The activity of covalently modified proteins (e.g., end-terminal or side chain modified peptides) can be evaluated by known methods.

As used herein, the terms "pro-IGF-I peptide," "pro-IGF-I protein," and "pro-IGF-I protein compound" are intended to include proteins comprised of naturally-occurring amino acids, as well as peptide derivatives, peptide analogues and peptide mimetics of the naturally-occurring amino acid structures (including the E-peptide). The terms "peptide analogue", "peptide derivative" and "peptidomimetic" as used herein are intended to include molecules which mimic the chemical structure of a peptide and retain the functional properties of the peptide. Approaches to designing peptide analogues, derivatives and mimetics are known in the art. For example, see Farmer, P. S., in Drug Design (E. J. Ariens, ed.) Academic Press, New York, 1980, vol. 10, pp. 119-143; Ball, J. B., and Alewood, P. F., (1990) *J. Mol. Recognition.* 3:55; Morgan, B. A., and Gainor, J. A., (1989) *Ann. Rep. Med. Chem.* 24:243; and Freidinger, R. M. (1989) *Trends Pharmacol. Sci.* 10:270.

In certain embodiments, the present disclosure encompasses derivative of a pro-IGF-I protein, peptide or a functional portion thereof. As used herein, a "derivative" of a compound (e.g., a peptide or amino acid) refers to a form of the compound in which one or more reactive groups on the compound have been derivatized with a modifying (derivative) group. Examples of peptide derivatives include peptides in which an amino acid side chain, the peptide backbone, or the amino- or carboxy-terminus has been derivatized (e.g., peptidic compounds with methylated amide linkages In certain embodiments, the present disclosure encompasses analogues and/or homologues of a pro-IGF-I protein, peptide or a functional portion thereof. An "analogue" of a reference amino acid, as the term is used herein, is an α- or β-amino acid having a side chain which is (a) the same as the side chain of the reference amino acid (when the analogue is a (3-amino acid residue, a peptide, or the D-amino acid enantiomer of the reference acid); (b) is an isomer of the side chain of the reference amino acid; (c) is a homologue of the side chain of the reference amino acid; (d) results from replacement of a methylene group in the side chain of the reference amino acid with a heteroatom or group selected from NH, O and S; (e) results from a simple substitution on the side chain of the reference amino acid or any of the preceding (a) to (c); and/or (f) results from a conservative substitution (discussed infra). Analogues of a reference amino acid can further include the reference amino acid or any of (a)-(e) above in which the α-nitrogen atom is substituted by a lower alkyl group, preferably a methyl group. A "homologue" of the given amino acid is an α- or β-amino acid having a side chain which differs from the side chain of the given amino acid by the addition or deletion of from 1 to 4 methylene groups. A "simple substitution" of an amino acid side chain results from the substitution of a hydrogen atom in the side chain of the given amino acid with a small substituent, such as a lower alkyl group, preferably a methyl group; a halogen atom, preferably a fluorine, chlorine, bromine or iodine atom; or hydroxy.

In certain embodiments, the present disclosure encompasses peptide mimetic forms of a pro-IGF-I protein, peptide or a functional portion thereof. "Peptide mimetics" that are structurally similar to therapeutically useful peptides can be used to produce an equivalent therapeutic or prophylactic effect. The term mimetic, and in particular, peptidomimetic, is intended to include isosteres. The term "isostere" as used herein is intended to include a chemical structure that can be substituted for a second chemical structure because the steric conformation of the first structure fits a binding site specific for the second structure. The term can include peptide back-bone modifications (i.e., amide bond mimetics) well known to those skilled in the art. Generally, peptidomimetics are structurally similar to a paradigm peptide (i.e., a peptide that has a biological or pharmacological activity, such as pro-IGF-I), but have one or more peptide linkages optionally replaced by a linkage such as: —CH$_2$NH—, —CH$_2$S—, —CH$_2$—CH$_2$—, —CH=CH— (cis and trans), —COCH$_2$—, —CH(OH)CH$_2$—, and —CH$_2$SO—, by methods known in the art and further described in the following references: Spatola, A. F. in "Chemistry and Biochemistry of Amino Acids, Peptides, and Proteins," B. Weinstein, eds., Marcel Dekker, New York, p. 267 (1983); Spatola, A. F., Vega Data (March 1983), Vol. 1, Issue 3, "Peptide Backbone Modifications" (general review); Morley, J. S. (1980) *Trends Pharm. Sci.* pp. 463-468 (general review); Hudson, D. et al., (1979) *Int. J. Pept. Prot. Res.* 14:177-185 (—CH2NH—, CH2CH2-); Spatola, A. F. et al., (1986) *Life Sci.* 38:1243-1249 (—CH2-S); Hann, M. M., (1982) *J. Chem. Soc. Perkin Trans.* 1307-314 (—CH—CH—, cis and trans); Almquist, R. G. et al. (1980) *J. Med. Chem.* 23:1392-1398 (—COCH2-); Jennings-White, C. et al., (1982) *Tetrahedron Lett.* 23:2533 (—COCH2-); Szelke, M. et al., *European Appln.* EP 45665 (1982) CA: 97:39405 (1982)(—CH(OH)CH2-); Holladay, M. W. et al., (1983) *Tetrahedron Lett.* 24:4401-4404 (—C(OH)CH2-); and Hruby, V. J., (1982) *Life Sci.* 31:189-199 (—CH$_2$—S—); each of which is incorporated herein by reference. In certain embodiments, a non-peptide linkage is —CH$_2$NH—.

Other examples of isosteres include peptides substituted with one or more benzodiazepine molecules (see, e.g., James, G. L. et al. (1993) *Science* 260:1937-1942). Other possible modifications include, without limitation, an N-alkyl (or aryl) substitution, backbone crosslinking to construct lactams and other cyclic structures, substitution of all D-amino acids for all L-amino acids within the compound ("inverso" compounds) or retro-inverso amino acid incorporation. By "inverso" is meant replacing L-amino acids of a sequence with D-amino acids, and by "retro-inverso" or "enantio-retro" is meant reversing the sequence of the amino acids ("retro") and replacing the L-amino acids with D-amino acids. For example, if the parent peptide is Thr-Ala-Tyr, the retro modified form is Tyr-Ala-Thr, the inverso form is thr-ala-tyr, and the retro-inverso form is tyr-ala-thr (lower case letters refer to D-amino acids). Compared to the parent peptide, a retro-inverso peptide has a reversed backbone while retaining substantially the original spatial conformation of the side chains, resulting in a retro-inverso isomer with a topology that closely resembles the parent peptide. See Goodman et al., (1981) *Perspectives in Peptide Chemistry* pp. 283-294. See also U.S. Pat. No. 4,522,752 by Sisto for further description of "retro-inverso" peptides. Other derivatives include C-terminal hydroxymethyl derivatives, 0-modified derivatives (e.g., C-terminal hydroxymethyl benzyl ether) and N-terminally modified derivatives including substituted amides such as alkylamides and hydrazides.

In certain embodiments, such peptide mimetics can have significant advantages over peptide embodiments, including, for example: more economical production, greater chemical stability, enhanced pharmacological properties (e.g., half-life, absorption, potency, efficacy, and the like), altered specificity (e.g., a broad-spectrum of biological activities), reduced antigenicity, and others. Labeling of peptidomimetics usually involves covalent attachment of one or more labels, directly or through a spacer (e.g., an amide group), to non-interfering position(s) on the peptidomimetic that are predicted by quantitative structure-activity data and/or molecular modeling. Such non-interfering positions generally are positions that do not form direct contacts with the macromolecules(s) to which the peptidomimetic binds to produce the therapeutic effect. Derivitization (e.g., labeling) of peptidomimetics should not substantially interfere with the desired biological or pharmacological activity of the peptidomimetic.

Systematic substitution of one or more amino acids of an amino acid sequence with a D-amino acid of the same type (e.g., D-lysine in place of L-lysine) can be used to generate more stable peptides. In addition, constrained peptides may be generated by methods known in the art (Rizo and Gierasch (1992) Annu. Rev. Biochem. 61:387, incorporated herein by reference); for example, by adding internal cysteine residues capable of forming intramolecular disulfide bridges which cyclize the peptide.

Nucleic Acid Molecules Encoding Proteins of the Disclosure

Another aspect of this disclosure pertains to isolated, non-naturally occurring, nucleic acid molecules that encode the pro-IGF-I proteins of this disclosure, and portions thereof, as well as complements of such nucleic acid molecules.

In certain embodiments, the non-naturally-occurring nucleic acid molecules of the disclosure are sufficiently complementary to a nucleotide sequence encoding a pro-IGF-I protein of this disclosure such that they can hybridize to a nucleotide sequence encoding a peptide of this disclosure, thereby forming a stable duplex. In certain embodiments, an isolated non-naturally-occurring nucleic acid molecule of the present disclosure includes a nucleotide sequence which is at least about: 70%, 71%, 72%, 73%, 74%, 75%, 76%, 77%, 78%, 79%, 80%, 81%, 82%, 83%, 84%, 85%, 86%, 87%, 88%, 89% 90%, 91%, 92%, 93%, 94%, 95%, 96%, 97%, 98%, or 99%, or more homologous to a nucleotide sequence encoding a pro-IGF-I proteins of this disclosure, or a portion of any of these nucleotide sequences. In certain embodiments, such non-naturally-occurring nucleic acids can be used as primer and/or probe sequences and will include lengths homologous to a sequence encoding a pro-IGF-I protein ranging from 5-100, 10-75, 10-50, 10-40, 10-30, or 10-20 nucleotides. In certain embodiments, for example with respect to certain types of probe sequences, the length homologous to a sequence encoding a pro-IGF-I protein will be longer, up to and including the full length of the pro-IGF-I coding sequence.

In certain embodiments, the nucleic acids can be present in whole cells, in a cell lysate, or in a partially purified or substantially pure form. A non-naturally occurring nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. F. Ausubel, et al., ed. (1987) Current Protocols in Molecular Biology, Greene Publishing and Wiley Interscience, New York. In certain embodiments, a non-naturally-occurring nucleic acid of the present disclosure can be, for example, DNA or RNA and may or may not contain intronic sequences. In certain embodiments, the non-naturally-occurring nucleic acid of the present disclosure is a cDNA molecule.

Recombinant expression vectors which include the non-naturally-occurring nucleic acids of the disclosure, and host cells transfected with such vectors, are also provided.

As used herein, the term "vector" refers to a nucleic acid molecule capable of transporting another nucleic acid to which it has been linked. In certain embodiments, the vector can include a plasmid, cosmid or viral vector. In certain embodiments, the vector can be capable of autonomous replication or it can integrate into a host DNA. Viral vectors include, e.g., replication defective retroviruses, adenoviruses and adeno-associated viruses. In certain embodiments, the expression vector can be a yeast expression vector, a vector for expression in insect cells, e.g., a baculovirus expression vector, or a vector suitable for expression in mammalian cells.

In certain embodiments, the recombinant expression vectors of the disclosure can be designed for expression of the peptides of the disclosure in prokaryotic or eukaryotic cells. For example, peptides of the disclosure can be expressed in E. coli, insect cells (e.g., using baculovirus expression vectors), yeast cells or mammalian cells. Suitable host cells are discussed further in Goeddel, (1990) Gene Expression Technology: Methods in Enzymology 185, Academic Press, San Diego, Calif. Alternatively, the recombinant expression vector can be transcribed and translated in vitro, for example using T7 promoter regulatory sequences and T7 polymerase.

The term "host cell" and "recombinant host cell" are used interchangeably herein. Such terms refer not only to the particular subject cell but to the progeny or potential progeny of such a cell. Because certain modifications can occur in succeeding generations due to either mutation or environmental influences, such progeny may not, in fact, be identical to the parent cell, but are still included within the scope of the term as used herein. A host cell can be any prokaryotic or eukaryotic cell. In certain embodiments, the host cell is a plant cell.

In certain embodiments, vector DNA, which include the nucleic acids of the disclosure, can be introduced into host cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation.

A host cell of the disclosure can be used to produce (i.e., express) a peptide of the disclosure. Accordingly, the disclosure further provides methods for producing a peptide of the disclosure using the host cells of the disclosure. In certain embodiments, the method includes culturing the host cell of the disclosure (into which a recombinant expression vector encoding a peptide of the disclosure has been introduced) in a suitable medium such that a peptide of the disclosure is produced. In certain embodiments, the method further includes isolating a peptide of the disclosure from the medium or the host cell.

Vectors

Vectors of the present disclosure include plasmids, phages, viruses, etc.; and are discussed in greater detail below. In certain embodiments, a therapeutic vector containing the nucleic acid sequence of the present disclosure can be used. A "therapeutic vector" as used herein refers to a vector which is acceptable for administration to an animal, such as a human. In certain embodiments, therapeutic vectors encoding the pro-IGF-I proteins of the present disclosure can be used in the methods of the disclosure for the treatment of IGF-I mediated diseases or disorders.

Vectors can contain the DNA of a transmissible agent, into which foreign DNA is inserted. A common way to insert one segment of DNA into another segment of DNA involves the use of enzymes called restriction enzymes that cleave DNA at specific sites (specific groups of nucleotides) called restriction sites. Generally, foreign DNA is inserted at one or more restriction sites of the vector DNA, and then is carried by the vector into a host cell along with the transmissible vector DNA. A segment or sequence of DNA having inserted or added DNA, such as an expression vector, can also be called a "DNA construct." A common type of vector is a "plasmid", which generally is a self-contained molecule of double-stranded DNA, usually of bacterial origin, that can readily accept additional (foreign) DNA and which can readily introduced into a suitable host cell. A plasmid vector often contains coding DNA and promoter DNA and has one or more restriction sites suitable for inserting foreign DNA. Coding DNA is a DNA sequence that encodes a particular amino acid sequence for a particular protein or enzyme. Promoter DNA is a DNA sequence which initiates, regulates, or otherwise mediates or controls the expression of the coding DNA. Promoter DNA and coding DNA may be from the same gene or from different genes, and may be from the same or different organisms. A large number of vectors, including plasmid and fungal vectors, have been described for replication and/or expression in a variety of eukaryotic and prokaryotic hosts. Non-limiting examples include pKK plasmids (Clonetech), pUC plasmids, pET plasmids (Novagen, Inc., Madison, Wis.), pRSET plasmids (Invitrogen, San Diego, Calif.), pCDNA3 plasmids (Invitrogen), pREP plasmids (Invitrogen), or pMAL plasmids (New England Biolabs, Beverly, Mass.), and many appropriate host cells, using methods disclosed or cited herein or otherwise known to those skilled in the relevant art. Recombinant cloning vectors will often include one or more replication systems for cloning or expression, one or more markers for selection in the host, e.g., antibiotic resistance, and one or more expression cassettes.

Suitable vectors of the present disclosure include, but are not limited to, viruses, such as adenoviruses, adeno-associated virus (AAV), vaccinia, herpesviruses, baculoviruses and retroviruses, parvovirus, lentivirus, bacteriophages, cosmids, plasmids, fungal vectors, naked DNA, DNA lipid complexes, and other recombination vehicles typically used in the art which have been described for expression in a variety of eukaryotic and prokaryotic hosts, and may be used for gene therapy as well as for simple protein expression.

In certain embodiments, viral vectors, such as adenoviral vectors, can be complexed with a cationic amphiphile, such as a cationic lipid, polyL-lysine (PLL), and diethylaminoethyldextran (DELAE-dextran), which can provide increased efficiency of viral infection of target cells (See, e.g., PCT/US97/21496 filed Nov. 20, 1997, incorporated herein by reference). AAV vectors, such as those disclosed in U.S. Pat. Nos. 5,139,941, 5,252,479 and 5,753,500 and PCT publication WO 97/09441, the disclosures of which are incorporated herein, are also useful since these vectors integrate into host chromosomes, with a minimal need for repeat administration of vector. For a review of viral vectors in gene therapy, see McConnell et al., 2004, Hum Gene Ther. 15(11):1022-33; Mccarty et al., 2004, Annu Rev Genet. 38:819-45; Mah et al., 2002, Clin. Pharmacokinet. 41(12): 901-11; Scott et al., 2002, Neuromuscul. Disord. 12(Suppl 1):523-9. In addition, see U.S. Pat. No. 5,670,488. Beck et al., 2004, Curr Gene Ther. 4(4): 457-67, specifically describe gene therapy in cardiovascular cells.

Pharmaceutical Compositions

The pro-IGF-I proteins of the disclosure can be formulated into compositions suitable for pharmaceutical administration. In certain embodiments, the pharmaceutical composition can include a pro-IGF-I protein (or modified form or fragment thereof as described above) and a pharmaceutically acceptable carrier. In certain embodiments, the pharmaceutical composition can include a nucleic acid encoding a pro-IGF-I protein or function portion thereof and a pharmaceutically acceptable carrier.

Pharmaceutical compositions of this disclosure also can be administered in combination therapy, i.e., combined with other agents. In certain embodiments, the combination therapy can include a pro-IGF-I protein of the present disclosure combined with at least one additional agent.

As used herein the term "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. In certain embodiments, supplementary active compounds can also be incorporated into the compositions.

A pharmaceutical composition of the disclosure is formulated to be compatible with its intended route of administration. For example, solutions or suspensions used for parenteral, intradermal, or subcutaneous application can include one or more of the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use can include sterile aqueous solutions (such as water) or dispersions and sterile powders for the extemporaneous preparation of sterile injectable solutions or dispersion. For intravenous administration, suitable carriers can include physiological saline, bacteriostatic water, Cremophor EL. (BASF, Parsippany, N.J.) or phosphate buffered saline (PBS). In certain embodiments, the composition must be sterile and can be fluid to the extent that easy syringability exists. In certain embodiments, the composition must be stable under the conditions of manufacture and storage and must be preserved against the contaminating action of microorganisms such as bacteria and fungi. In certain embodiments, the carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In certain embodiments, isotonic agents, for example, sugars, polyalcohols such as manitol, sorbitol, sodium chloride can be included in the composition. Prolonged absorption of the injectable compositions can be brought about by including in the composition an agent which delays absorption, for example, aluminum monostearate and gelatin.

In certain embodiments, sterile injectable solutions can be prepared by incorporating the active compound (i.e., the pro-IGF-I peptide or functional derivative thereof) in the required amount in an appropriate solvent with one or a combination of ingredients enumerated above, as required, followed by filtered sterilization. Dispersions can be prepared by incorporating the active compound into a sterile vehicle which contains a basic dispersion medium and the required other ingredients from those enumerated above. In the case of sterile powders for the preparation of sterile injectable solutions, methods of preparation can include vacuum drying and freeze-drying which yields a powder of the active ingredient plus any additional desired ingredient from a previously sterile-filtered solution thereof. In certain embodiments, a sterile injectable composition can include a therapeutic vector containing a nucleic acid encoding a pro-IGF-I protein or function portion thereof.

In certain embodiments, oral compositions can include an inert diluent or an edible carrier. They can be enclosed in gelatin capsules or compressed into tablets. For the purpose of oral therapeutic administration, the active compound can be incorporated with excipients and used in the form of tablets, troches, or capsules. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

In certain embodiments, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc.

In certain embodiments, liposomal suspensions (including liposomes targeted to tumor cells with monoclonal antibodies to tumor antigens) can also be used as pharmaceutically acceptable carriers. These can be prepared according to methods known to those skilled in the art, for example, as described in U.S. Pat. No. 4,522,811, and International Patent Application Serial PCT/US94/07327. For example, liposome formulations can be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of invariant chain protein or peptide is then introduced into the container. The container is then swirled by hand to free lipid material from the sides of the container and to disperse lipid aggregates, thereby forming the liposomal suspension.

Pharmaceutical compositions, including, but not limited to, such liposomal suspensions and other microencapsulated compositions, can be combined with targeting agents to allow for tissue or tumor specific delivery of the pro-IGF-I proteins of the disclosure. In certain embodiments, such targeting can be achieved, without limitation, through the use of tissue and/or tumor specific antibodies and antibody mimetics. Non-limiting examples of antibody mimetics include, but are not limited to, molecules such as Affibodies, DARPins, Anticalins, Avimers, and Versabodies, all of which employ binding structures that, while they mimic traditional antibody binding and therefore can be used to target peptides to tissues specifically expressing the antigen recognized by the mimetic, are generated from and function via distinct mechanisms.

Pharmaceutical compositions may also be prepared wherein the pro-IGF-I proteins of the disclosure is covalently or non-covalently attached to a nanoparticle. By way of example, but not limitation, a nanoparticle can be a dendrimer, such as the polyamidoamine employed in Kukowska-Latallo et al., (2005) Cancer Res., vol. 65, pp. 5317-24, which is incorporated herein by reference in its entirety. Other dendrimers that can be used in conjunction with the pro-IGF-I proteins of the instant disclosure include, but are not limited to, Polypropylenimine dendrimers as described in U.S. Pat. No. 7,078,461, which is hereby incorporated by reference in its entirety.

In certain embodiments, the oral or parenteral compositions can be formulated in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on (a) the unique characteristics of the active compound and the particular therapeutic effect to be achieved, and (b) the limitations inherent in the art of compounding such an active compound for the treatment of individuals.

Actual dosage levels of the active ingredients in the pharmaceutical compositions of the present disclosure can be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present disclosure employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

As used herein, a "therapeutically effective amount" refers to that amount of the compound sufficient to treat, prevent, or manage an IGF-I mediated disease or disorder. A therapeutically effective amount can refer to the amount of a compound that provides a therapeutic benefit in the treatment or management of an IGF-I mediated disease or disorder. Further, a therapeutically effective amount with respect to a pro-IGF-I protein of the disclosure can mean the amount of protein alone, or in combination with other therapies, that provides a therapeutic benefit in the treatment or management of an IGF-I mediated disease or disorder, which can include a decrease in severity of disease symptoms, an increase in frequency and duration of disease symptom-free periods, or a prevention of impairment or disability due to the disease affliction. The term can encompass an amount that improves overall therapy, reduces or avoids unwanted effects, or enhances the therapeutic efficacy of or synergies with another therapeutic agent.

Animal models accepted in the art as models of IGF-I diseases or disorders can be used to test particular peptide compounds, routes of administration etc., to determine appropriate amounts of the peptide compounds of the disclosure.

The ability of a compound to inhibit IGF-I diseases or disorders can be evaluated in an animal model system predictive of efficacy in human IGF-I diseases or disorders. Alternatively, this property of a composition can be evaluated by examining the ability of the compound to increase IGF-I level or activity in cells, such increase in level or activity can be measured in vitro by assays known to the skilled practitioner and described herein.

In certain embodiments, a composition of the present disclosure can be administered via one or more routes of administration using one or more of a variety of methods known in the art. As will be appreciated by the skilled artisan, the route and/or mode of administration will vary depending upon the desired results. Routes of administration for pro-IGF-I proteins of this disclosure include, but are not limited to, intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

In certain embodiments, a pro-IGF-I protein of this disclosure can be administered via a non-parenteral route, such as a topical, epidermal or mucosal route of administration, for example, intranasally, orally, vaginally, rectally, sublingually or topically.

In certain embodiments, therapeutic compositions can be administered with medical devices known in the art. For example, in certain embodiments, a therapeutic composition of this disclosure can be administered with a needleless hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules useful in the present disclosure include: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art.

Kits are also contemplated for the disclosed subject matter. In certain embodiments, a kit can include a container, such as a vial, for the pro-IGF-I protein formulation including a pro-IGF-I protein in a pharmaceutically acceptable buffer and instructions, such as a product insert or label, directing the user to utilize the pharmaceutical formulation for treating a disease or disorder mediated by IGF-I in a subject. The kit optionally includes a container, preferably a vial, for a combination molecule. In certain embodiments, a kit can include a container, such as a vial, for the pro-IGF-I nuclei acid formulation including a vector containing a pro-IGF-I nucleic acid sequence in a pharmaceutically acceptable buffer and instructions, such as a product insert or label, directing the user to utilize the pharmaceutical formulation for treating a disease or disorder mediated by IGF-I in a subject.

The present disclosure is further illustrated by the following Examples which should not be construed as further limiting.

EXAMPLES

Example 1: Functional Activity of IGF-I Variants

Materials and Methods
Viral and Plasmid Constructs.

Recombinant adeno-associated virus serotype 2/8 (AAV2/8) produced at the University of Pennsylvania Vector Core and harboring the igf1 cDNAs of murine class I IGF-IA, IGF IB and mature IGF-I sequences was used to express these IGF-I forms in skeletal muscle, as described previously (21). Briefly, IGF-IA and IGF-IB included the sequence to encode the class I signal peptide, IGF-I, and the EA- and EB-peptide, respectively. IGF-IS lacked E-peptide sequence, and a stop codon was inserted at the end of the mature IGF-I (A70X). Plasmid DNA constructs containing the same igf1 cDNAs used for the viral constructs were also utilized for transfections of 3T3 cells, in order to overexpress IGF-I. Additional mutants were generated by site-directed mutagenesis (QuikChange II; Stratagene, La Jolla, Calif., USA) to inhibit cleavage between mature IGF-I and the E peptide and/or N-glycosylation of the EA peptide. Only the predominant isoform of IGF-I (IGF-IA) was mutagenized, since it represents ~90% of the IGF-I produced by the muscle and liver, and harbors potential N-glycosylation sites (9). IGF-IA Cleavage inhibition required mutagenesis of 3 sites: K68G, R71A, R77A (IGF-IKRR). Prevention of N-glycosylation in the EA peptide was achieved through the site-directed mutagenesis of N92D (IGF-IN1), N100D (IGF-IN2), or both residues (IGF INN). Finally mutant constructs blocking both cleavage and N-glycosylation sites were generated to produce only pro-IGF-I (IGF-IKRRNN). All cDNA constructs were inserted into the NheI and XhoI restriction sites of pCMV.IRES.eGFP vector (Clontech, Mountain View, Calif., USA) for transient transfection as previously described (Pfeffer et al, 2009).

Muscle AAV Injections.

Viral injections of $1\times10^{11}$ particles diluted in 75-100 µl of phosphate-buffered saline (PBS) were performed into the anterior compartment of one lower hindlimb of anesthetized C57Bl/6 mice targeting the tibialis anterior (TA) muscle. The contralateral limb received an equal volume of PBS in the same manner as a control for the injection procedure. After injection, mice were housed in the animal facility until time of analysis. Mice (n=4 for each construct) were 2-3 wk of age at the time of injection. They were killed 4 weeks after injection and exsanguinated, and the tibialis anterior muscle and other tissues were dissected and rapidly frozen in liquid nitrogen for biochemical analysis. Serum was separated from whole blood by centrifugation and stored at −80° C. for subsequent analysis.

Cell Culture-Transfection.

$1.2\times10^6$ 3T3 cells were grown on 6-well plates (Falcon, BD Bioscienses, Sparks, Md., USA) in DMEM media containing 10% Fetal Bovine Serum and supplemented with 100 U/mL ampicillin and 100 U/mL streptomycin. Transient transfection was performed using Lipofectamine 2000 (Invitrogen, Carlsbad, Calif., USA). For each transfection, cells were mixed with 0.5 mL of Opti-MEM (Invitrogen) containing 6 µg of plasmid DNA plus 8 µl of Lipofectamine, and then 1.5 mL DMEM plus 10% FBS was added, and the cells were incubated for a total of 4 h. Cells were switched into minimal media (DMEM medium supplemented with 100 U/mL ampicillin and 100 U/mL streptomycin) for 24 h after transfection. Controls included transfection of empty vector (green fluorescent protein, GFP) and no transfection (control). The next day, media from transfected 3T3 cells was utilized for ELISA and immunoblotting measurements of IGF-I, and for KIRA assays (described below). 3T3 cells pellets were also retained for determining transfection efficiency.

Immunoblotting Analysis.

Tissues were removed from liquid nitrogen storage and homogenized in 10 volumes/muscle wet weight of modified RIPA lysis buffer (50 mM Tris.HCl pH 7.4, 1% w/v Triton X-100, 0.25% sodium deoxycholate, 150 mM NaCl, 1 mM PMSF, 1 µg/ml aprotinin, 1 µg/ml leupeptin, 1 µg/ml pepstatin, 1 mM NaVO4, 1 mM NaF, 1 mM EGTA). Extracts from transfected cells were obtained by cell lysis in the same RIPA buffer. Tissue homogenates and cell lysates were centrifuged to pellet debris, and the total protein was measured in the supernatant using the Bradford procedure (Bio-Rad protein assay, Hercules, Calif., USA). Media from transfected cells were concentrated 10-15 fold using microcentrifugal filters (Microcon, Millipore, Billerica, Mass.) and with the addition of protease inhibitors (P8340, Sigma), and then subjected to immunoblotting. Equal amounts of protein from tissue and cell lysate, or equal volumes of media were subjected to SDS-PAGE using 16.5% Tris/Tricine or 12.5% Tris/Glycine gels and transferred to polyvinylidene fluoride membranes (Immobilon-P, Millipore, Bedford, Mass., USA).

The following primary antibodies were used for the immunodetection of the IGF-1 isoforms and the processing products derived from each isoform: a rabbit polyclonal anti-IGF-IEb antibody (1:20,000 dilution) (22), a mouse polyclonal anti-IGF-1Ea (1:250 dilution) (13), and a goat polyclonal anti-mature IGF-I antibody (1:500 dilution) (AF791; R&D Systems, Minneapolis, Minn., USA). Concentrated media was also probed for IGFBP-3 (R&D systems, MAB775), to determine if the transfected constructs modulated the level of this protein. Immunoblotting of cell pellets for transfection efficiency utilized antibodies for GFP (#2955, Cell Signaling, Beverly, Mass.), and tubulin (T5168, Sigma). Following washes and exposure to secondary antibodies, specific bands were visualized by x-ray film and by Image Quant LAS 4000 (GE), after incubation with an enhanced chemiluminescent (ECL) substrate (Western lightning-ECL, PerkinElmer, Waltham, Mass., USA). Analysis of band intensity was performed by use of the associated Image Quant software. Membranes were stained with Coomassie brilliant blue R-250 after immunoblotting to confirm equal protein loading.

ELISA Assays.

Total IGF-1 content in muscle protein extracts and in conditioned media was determined by a standard sandwich ELISA protocol using commercially available kit (MG100, R&D Systems) according to manufacturer's recommendations and as previously described (4, 23). This kit detects total rodent IGF-I and can also detect endogenous IGF-I production by C2C12 cells, while there is no cross reactivity or interference with IGF-II or IGF binding proteins. The assay can detect IGF-I at 30-2000 pg/ml, with an intra-assay precision of 4.3% and an inter-assay precision of 5.9%. Data were acquired in duplicate using a SpectraMax M5 plate reader (Molecular Devices, Sunnyvale, Calif.) at 450 nm and the results were averaged.

Furin Cleavage.

To identify the potential processing products of each IGF-I isoform, total protein lysates from AAV injected TA muscles from C57BL/6 mice were incubated with recombinant protease furin (Recombinant Human Furin, 1503-SE-010, R&D Systems) according to manufacturer's recommendations. Furin processes proproteins by cleaving at specific motifs (i.e., K-X-X-K-X-X-R-X-X-R-X-X-R (SEQ ID NO: 2)) usually residing at the end of their pro regions. Equal amounts (30 μg) of total protein from each AAV-injected IGF-IA, IGF-IB and IGF-IS muscle lysate were incubated with furin (20 U of furin per 30 μg of each muscle lysate) overnight at 37° C. The corresponding volume of furin assay buffer [25 mM Tris, 1 mM CaCl2, 0.5% (w/v) Brij-35, pH: 9.0] for each muscle lysate was used as control. After overnight incubation with furin or furin assay buffer, muscle total protein extracts were subjected to immunoblotting and to ELISA for IGF-I detection.

Deglycosylation.

To identify the putative glycosylated (and non-glycosylated) forms of IGF-I, total protein isolated from AAVIA-injected TA muscles was incubated with N-Glycosidase F, which cleaves between the innermost GlcNAc and asparagine residues of high mannose and complex oligosaccharides from N-linked glycoproteins. 80 μg of AAV IGF-IA muscle protein extract were incubated with 2,500 U of PNGase F (PNGase F, no. P0705S; New England Biolabs, Hitchin, UK) for 3 hours at 37° C., according to manufacturer's recommendations. The corresponding volume of N-Glycosidase assay reaction buffer [G7 reaction buffer (10×), glycoprotein denaturing buffer (10×), NP-40 (10%)] without containing the enzyme PNGase F was used as control. After 3-hour incubation with PNGase F or reaction buffer, muscle protein extracts were subjected to immunoblotting for IGF-I detection. Alternatively, the samples were purified using Microcon centrifugal filters (Millipore, Billerica, Mass., USA), and then incubated with furin, or furin assay buffer (control) overnight at 37° C. as described in the previous section. The final reactions were then subjected to immunoblotting for IGF-I detection. The deglycosylation buffer conditions were not compatible with ELISA measurements, and so they were not pursued.

IGF-IR Activation Assay.

To compare the potency of IGF-IR activation by the IGF-I forms secreted from 3T3 cells following transfection, a KIRA assay was performed as previously described (24) with some alterations. Briefly, $2.5 \times 10^4$ P6 cells, which overexpress IGF-IR were seeded into 96-well plates. They were maintained in growth media supplemented with 200 μg/ml G418. The cells were serum-starved for 6 hours, and then treated for 15 minutes with fresh media harvested from the transfected 3T3 cells. Controls included P6 cells treated with media alone, or with recombinant IGF-I (1-100 nM). For each of 4 KIRA experiment replicates, one well of 3T3 cells was transfected with a single IGF-I construct, giving rise to conditioned media containing the IGF-I form produced by the construct. Each media sample was tested in triplicate on P6 cells. The P6 cells were lysed and IGF-IR was captured onto an ELISA plate coated with an antibody to IGF-IR (MAB1120, Millipore, Billerica, Mass.). An HRP-conjugated antibody to phosphorylated tyrosines (16-454, Millipore) and TMB substrate (N301, Thermo Scientific, Rockfort, Ill.) were used for colorimetric quantification. Absorbance was read at 450 nm via the SpectraMax M5 plate reader (Molecular Devices, Sunnyvale, Calif.). The triplicate samples were average for each construct within each replicate. Calculation of relative activity for each replicate was performed as described below.

First, the KIRA assay provided the level of receptor activation caused by any given sample. This was performed with equal volumes of conditioned media before knowing the quantity of IGF-I to avoid freeze thaw cycles. Second, the level of IGF-I production in any given transfection was calculated by Western blotting through comparisons to recombinant IGF-I. This controlled for the efficiency of the transfection and production of each construct. Last, the proportion of each form produced by any given transfected construct was also determined by densitometry of the immunoblots. This controlled for the differential post-translational processing of the IGF-I constructs by the cells.

Data from one replicate is used as an example for calculating the activity of any given IGF-I form. Table 1 includes the data generated from the KIRA assay and the subsequent immunoblotting for total IGF-I. KIRA values were divided by total IGF to calculate the activation for each transfection. In each replicate, these values were normalized by IGF Stop result to use in the final calculation. Table 2 shows the proportion of each form produced by each transfection (densitometry calculations). Note that IStop can only produce mature IGF-I, and in this case KRRNN produced only pro-IGF-I.

TABLE 1

| | KIRA Assay and Blotting | | | |
|---|---|---|---|---|
| Transfected Construct | KIRA Raw | Total IGF-I (Blot) | KIRA/Total IGF | KIRA (rel to IStop) |
| IA | 45.83 | 1.6.27 | 28.17 | 0.59 |
| Istop | 38.98 | 0.8.14 | 47.89 | 1.00 |
| NN | 65.8 | 1.5.53 | 42.38 | 0.88 |
| KRR | 23.56 | 0.8.04 | 29.31 | 0.61 |
| KRRNN | 42.65 | 0.9.61 | 44.39 | 0.93 |
| Vector | 3.62 | 0 | ND | 0 |
| Mock | −0.5 | 0 | ND | 0 |

TABLE 2

| Transfected | Proportion of IGF-I Form | | |
|---|---|---|---|
| Construct | Gly Pro (GP) | Pro (P) | Mature (M) |
| IA | 0.532 | 0.243 | 0.233 |
| iStop | 0 | 0 | 1 |
| NN | 0 | 0.769 | 0.231 |
| KRR | 0.649 | 0.351 | 0 |
| KRRNN | 0 | 1 | 1 |
| Vector | ND | ND | ND |
| Mock | ND | ND | ND |

Next, a series of equations were generated for the transfections following the form:

$$\% \ GP + \% \ P + \% \ M = Rel \ KIRA$$

where % were the proportions of any given form, GP, P, and M (Table 2), and Rel KIRA was KIRA normalized to IStop. In this example, $0.53GP + 0.24P + 0.22M = 0.59$     IA:

$0GP + 0P + 1.0M = 1.00$     IStop:

$0GP + 0.77P + 0.23M = 0.88$     NN:

$0.65GP + 0.35P + 0M = 0.61$     KRR:

$0GP + 1.0P + 0M = 0.93$     KRRNN:

Because the activation by mature IGF-I (M) was set to 1.0, the equations can be reduced by substituting 1 for M:

$0.53GP + 0.24P + 0.22 = 0.59$     IA:

$0GP + 0P + 1.0 = 1.00$     IStop:

$0GP + 0.77P + 0.23 = 0.88$     NN:

$0.65GP + 0.35P + 0 = 0.61$     KRR:

$0GP + 1.0P + 0 = 0.93$     KRRNN:

Leaving the following, $0.53GP + 0.24P = 0.37$     IA:

$M = 1.00$     IStop:

$0GP + 0.77P = 0.65$     NN:

$0.65GP + 0.35P = 0.61$     KRR:

$0GP + 1.0P = 0.93$     KRRNN:

Solution for P is achieved by NN and KRRNN equations:

$0.77P = 0.65$ $P = 0.84$     NN:

$1.0P = 0.93$ $P = 0.93$     KRRNN:

$P = 0.89$     Mean:

Substitution of P in the remaining equations:

$0.53GP + 0.24(0.89) = 0.37$ $0.53GP + 0.21 = 0.37$ $0.532GP = 0.16$ $GP = 0.30$     IA:

$0.65GP + 0.35(0.89) = 0.61$ $0.65GP + 0.31 = 0.61$ $0.65GP = 0.30$ $GP = 0.47$     KRR:

$GP = 0.38$     Mean:

IGF-IR activity can also be determined by any method known in the art. For example, Immunoprecipitation of the IGF-IR protein after activation can isolate these receptors. Subsequently, immunoblotting is performed with antibodies directed to IGF-IR and to phospho-tyrosines, which are the activated sites upon ligand binding. This method will provide the relative phosphorylation of the IGF-IR caused by IGF-I binding. An alternative method is to immunoblot for signaling pathways downstream of the IGF-IR (e.g., P-ERK1/2 and P-Akt).

Statistical Analysis.

One-way analysis of variance (ANOVA) was employed to evaluate changes in IGF-I content in both muscle lysates and cell conditioned media in all viral infection and transfection conditions, as well as the KIRA assays. Where significant F ratios were found for main effects ($P<0.05$), the means were compared using Tukey's post-hoc tests. Unpaired t-tests were used for comparisons of results from furin experiments. All data are presented as mean±standard error of the mean (SEM). The level of statistical significance was set at $P<0.05$.

Results

Figure 2B:
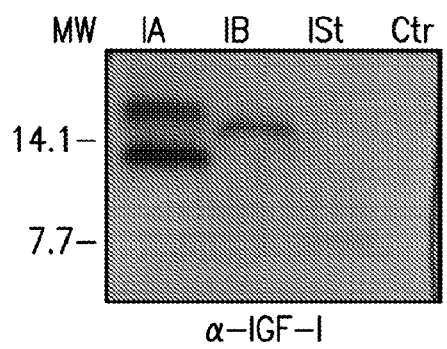
Figure 2C:
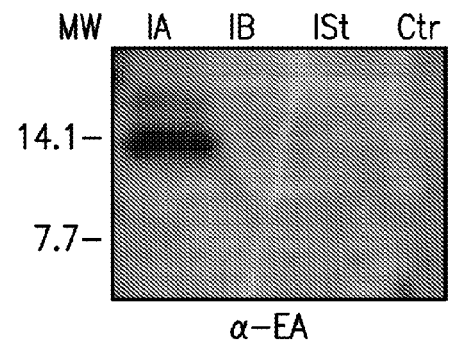
Figure 2D:
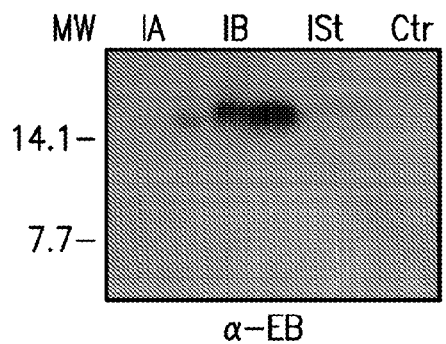
Figure 2E:
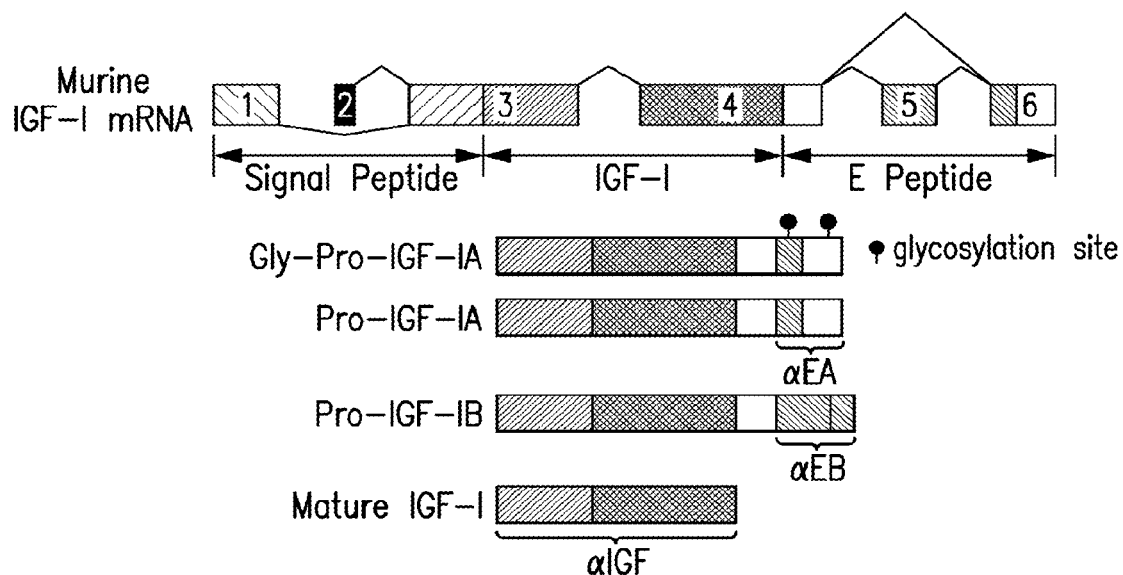

A goal of the disclosed subject matter was to examine the forms of IGF-I in muscle. To improve the ability to detect IGF-I, muscle samples subjected to viral mediated delivery of IGF-IA, IGF-IB, and mature IGF-I (IGF-ISt) were utilized. The levels of IGF-I in the AAV-injected and control muscles were quantified by ELISA. While all injections resulted in significantly higher IGF-I content than in uninjected controls, the production following viral delivery of IGF-ISt exceeded the levels produced by either IGF-IA or IGF-IB by more than 40% (FIG. 2A). To determine the forms of IGF-I produced after viral delivery to murine skeletal muscle, immunoblotting of muscle lysates was performed with antibodies specific to IGF-I as well as to the EA and EB peptides (FIG. 2E). In contrast to the ELISA measurements, the bands detected after AAV injection of IGF-IA or IGF-IB constructs were of much higher intensity than the bands found in samples injected by AAV-IGF-ISt, where there was little detectable mature IGF-I (FIG. 2). Further, the predominant bands from IGF-IA or IGF-IB samples migrated at a higher molecular weight (FIG. 2B). IGF-ISt produced one band ~8 kD in size, which was the predicted size for mature IGF-I, yet IGF-IA expression generated 13 and 17 kD bands, and IGF-IB expression produced a single 14 kD band. To clarify what species of IGF-I were produced, additional E-peptide specific antibodies were used (13, 22). IGF-IA expression produced two major bands, presumably pro-IGF-IA and gly-pro-IGF IA, for they were detected by antibodies recognizing the EA-peptide (FIG. 2C). The intensities of these bands were equivalent when using the mature IGF-I antibody, but the predicted glycosylation found in the higher molecular weight band decreased affinity for the EA antibody. IGF-IB expression produced one 14 kD band, which was presumed to be pro-IGF-IB, for it was recognized by antibodies for EB and for mature IGF-I (FIG. 2D).

Figure 2F:
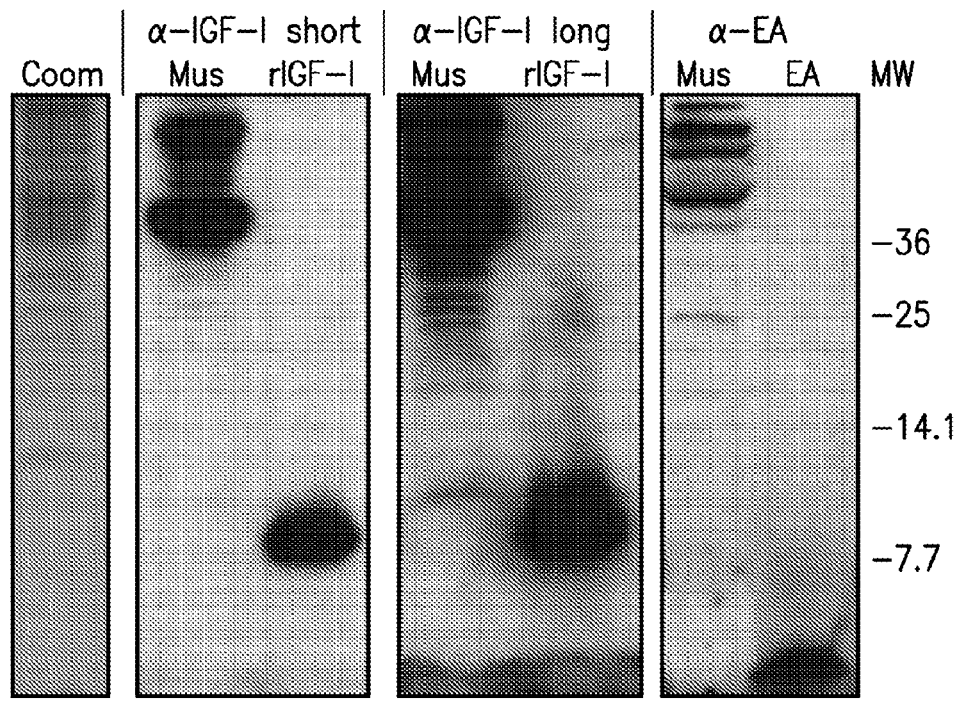

Thus, the majority of IGF-I species retained in muscle following viral delivery of the full-length Igf1 open reading frames are pro-IGF-I forms, not mature. The immunoblotting detection method was extended to measure endogenous forms of IGF-I in muscle, by increasing the protein loading on the gel, and increasing exposure duration of the blot. Muscle had high molecular weight bands in addition to mature IGF-I (FIG. 2F). Two bands of ~17 and 25 kD were also detected by the antibody for EA, supporting that these bands were pro-IGF-I, and most likely glycosylated based on their size. Therefore, a significant proportion of IGF-I found in naïve muscle or after viral delivery is not mature IGF-I, but the pro-IGF-I forms.

Figure 3A:
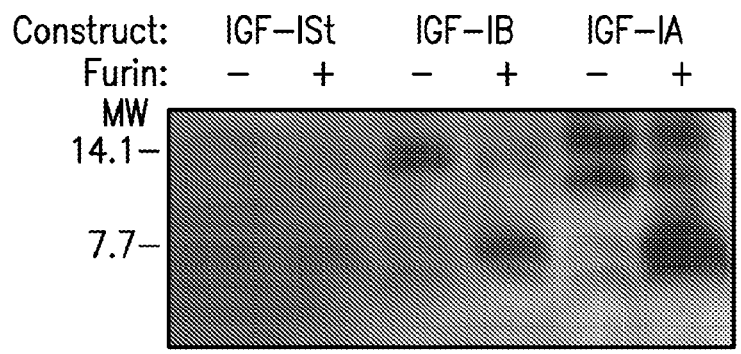
FIG. 3A-3C. Identification of the multiple forms produced by viral delivery of the IGF-I isoforms. A. Furin digest confirms that the higher molecular weight forms produced by IGF-IA and IGF-IB can be cleaved to produce mature IGF-I, which is the only form produced by IGF-ISt. Blot shows the same muscle lysates with and without furin digest. B. De-glycosylation of IGF-IA confirms that the highest molecular weight bands produced by this isoform are glycosylated, and removal of the side-chains collapse the gly-pro-IGF-I bands to pro-IGF-I. Combined PNGase and furin digest results in increased mature IGF-I. Blot shows the same muscle lysate sample split into 4 equivalent aliquots. C. ELISA quantification before and after furin digestion shows the cleavage of the C-terminal extension increases the detectable pool of IGF-I after viral delivery of IGF-IA and IGF-IB, but does not change the observed IGF-I in control muscle (no viral delivery) nor following delivery of AAV-IGF-ISt. *, $P<0.05$ for comparisons between apparent IGF I levels before and after furin digest.
Figure 3B:
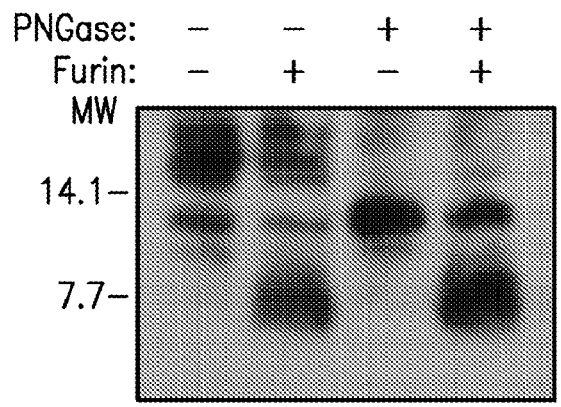
Figure 3C:
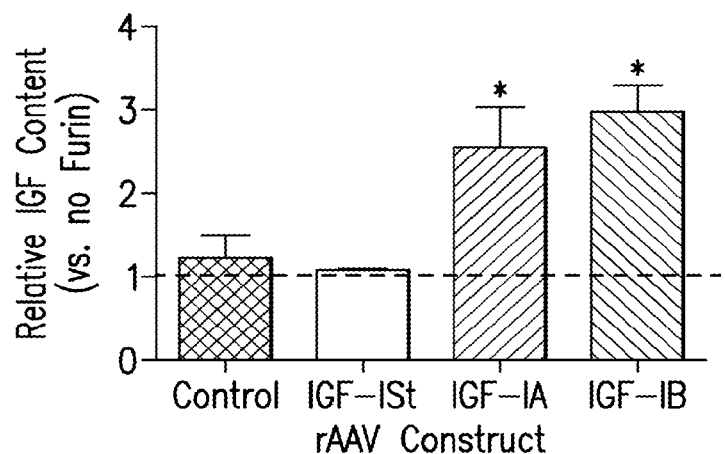

To clarify the identity of IGF-I forms produced by IGF-IA and IGF-IB, muscle lysates were incubated with furin and/or glycosidase to cleave mature IGF-I from the E-peptide, and to separate the glycosylated side chains from asparagine residues, respectively. This experiment required the levels of IGF-I produced by AAV, because the endogenous IGF-I was too low for immunoblot detection following enzyme digestion. As shown in FIG. 3A, furin treatment produced mature IGF-I in both IGF-IA and IGF-IB muscle lysates. In addition, glycosidase collapsed the gly-pro-IGF-IA forms to a single pro-IGF-I band (FIG. 3B), and subsequent furin cleavage efficiency was not affected by glycosylation. IGF-IB was not evaluated by glycosidase because it does not contain putative N-glycosylation sites. Importantly, it appeared that ELISA measurements were most sensitive to mature IGF-I, not the pro-forms (FIG. 2), suggesting that the presence of either E-peptide impaired the ability for the IGF-I antibody in the ELISA to recognize the protein. To determine if the pro-IGF-I forms impaired ELISA detection, muscle lysates were incubated with furin, and then subjected to IGF-I quantification by ELISA. Comparison of ELISA measurements of the same sample before and after furin treatment showed that apparent IGF-I levels increased following furin treatment in IGF-IA or IGF-IB muscles, but did not change in IGF-ISt (FIG. 3C). Control muscles showed some elevation of IGF following furin digestion, but this change was not significant. Thus, it appeared that the release of the E-peptide afforded better IGF-I detection under native conditions, and that the E-peptide impaired the ability to accurately measure IGF-I levels with this method.

Figure 4A:
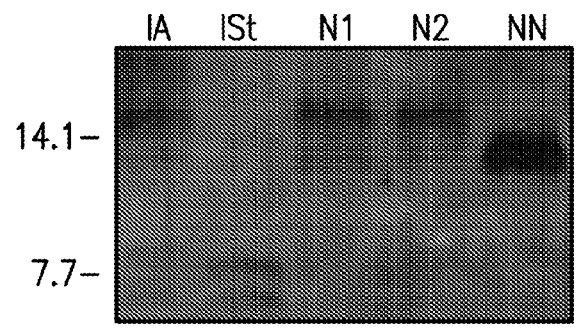
FIG. 4A-4F. Secretion of IGF-I forms following transient transfection of IGF-IA constructs. A. Determination of N-glycosylation sites in IGF-IA by immunoblot. IGF-IA transfection produces a cluster of bands from 17-20 kD, which are presumably glycosylated. Mutation of either N92 or N100 results in secretion of a single gly-pro-IGF-I band. Only when both sites are mutated do all gly-pro-IGF-I bands disappear. IA, transfection of wild-type IGF-IA; N1, transfection of IGF-IA with N92A mutation; N2, transfection of IGF-IA with N100A mutation; NN, transfection of IGF-IA with N92A/N100A mutation. B. Immunoblot detection of the IGF-I forms secreted. Ist, IGF-ISt transfection; IA, transfection of wild type IGF-IA; KR, blockade of cleavage site between mature IGF-I and the E-peptide; NN, blockade of potential glycosylation sites; KN, blockade of both cleavage and glycosylation; V, vector only; M, mock transfection. C. The proportion of IGF-I forms secreted following transient transfection. IGF-IA transfection produces predominantly gly-pro-IGF-I, which is prevented when glycosylation is blocked by site-directed mutagenesis of asparagines in the E-peptide (IGF-INN, IGF-KRRNN). Mature IGF-I secretion is inhibited by cleavage blockade (IGF-IKRR, IGF-IKRRNN). D. ELISA measurements of IGF I secreted following transient transfection. Data is presented as IGF-I levels normalized to that in media from mature IGF-I transfections for 4 experiments that include all constructs. E. Quantification of total IGF-I secreted following transient transfection based on immunoblot. *, $P<0.05$ significantly different compared to mature IGF-I. F. Ratio of ELISA and immunoblot quantification shows that presence of glycosylation causes an underestimation of IGF-I by ELISA. Data is presented as the sum of all IGF-I bands produced by each construct normalized to bands from transfection of mature IGF-I in 4 experiments. *, $P<0.05$ significantly different compared to mature IGF-I.

The multiple species of IGF-I produced in muscle raised the question of which form(s) can activate the IGF-I receptor. A cell-based system was then used in order to control both the form produced and to enable quantification of receptor activation. Initially, it was determined which asparagine residue was utilized for glycosylation. Immunoblotting of media from 3T3 cells transfected with IGF-IA revealed a cluster of glycosylated bands (FIG. 4A). Transfection of IGF-IN1 or IGF-IN2 resulted in a single 17 kD band, whereas transfection of IGF-INN, harboring a double mutation of N92 and N100, 257 resulted in a kD band lacking any glycosylation. Thus, both asparagine residues can be utilized for glycosylation.

Figure 4B:
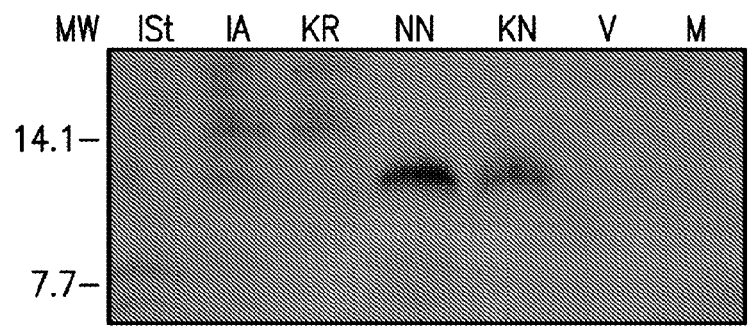
Figure 4C:
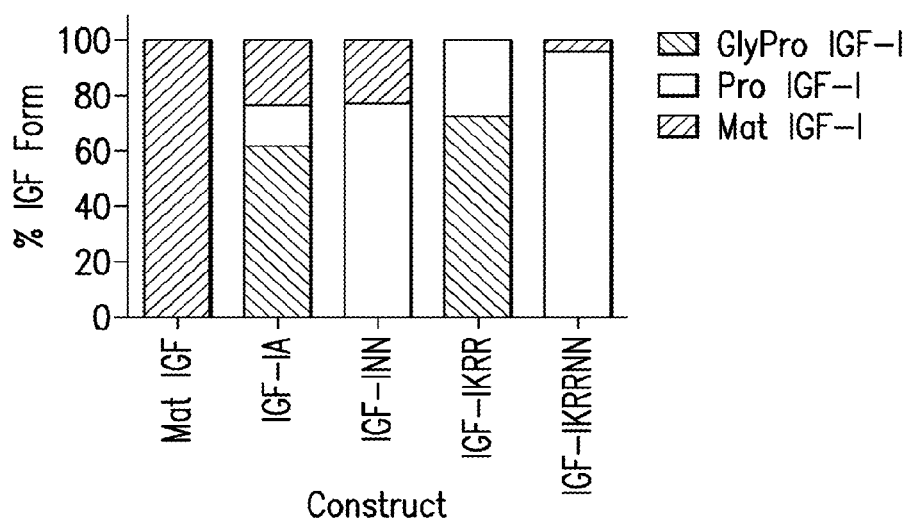

The sets of constructs were expanded to include those with blockade of cleavage (IGF-IKRR) as well as blockade of cleavage and glycosylation (IGF-IKRRNN). As shown in FIG. 4B, IGF-Ist transfected cells secreted only mature IGF-I. Cells transfected with IGF-IA secreted mature, pro- and gly pro-forms, and the presence of gly-pro-IGF was eliminated by transfection of IGF-INN. Likewise, the mutation of the cleavage sites between mature IGF-I and the E-peptides by IGF-IKRR transfection blocked secretion of mature IGF-I. Finally mutation of both cleavage and glycosylation significantly reduced secretion of mature IGF-I, and completely prevented secretion of gly-pro-IGF-I. These band patterns were consistent for N=4 separate series of transfections. The mean proportions of each IGF-I form with respect to the specific construct are displayed in FIG. 4C. Immunoblotting of cell lysates for GFP confirmed that the variability in IGF-I secretion was not due to the transfection efficiency.

Figure 4D:
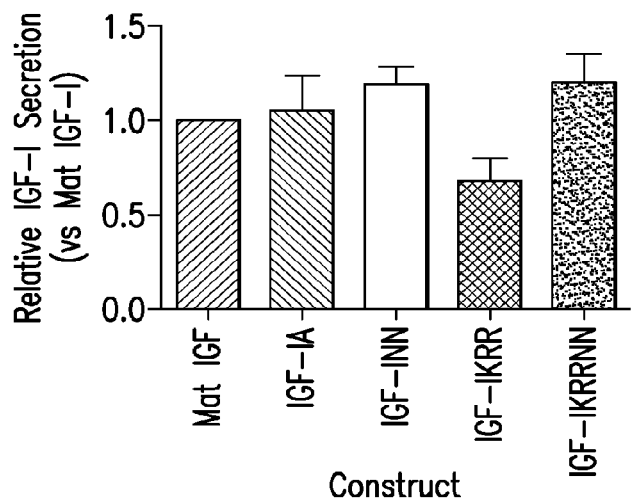
Figure 4E:
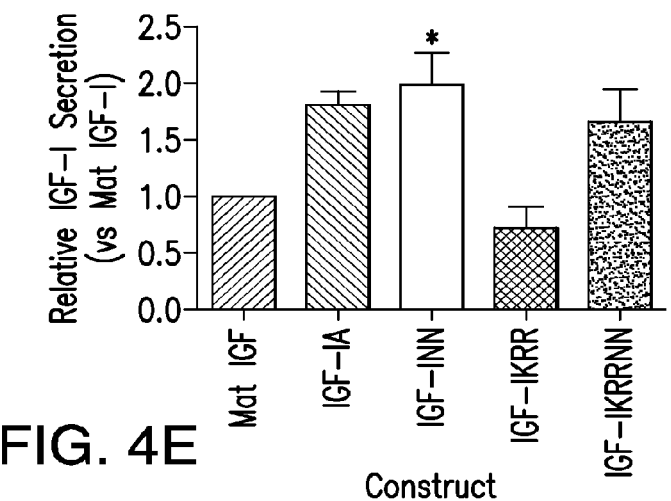
Figure 4F:
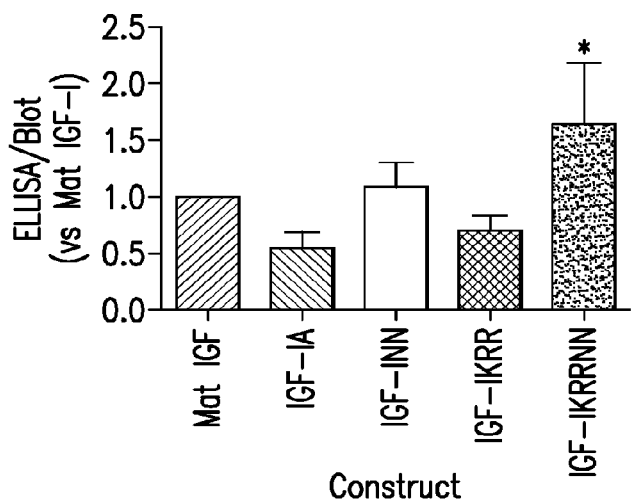

Comparison of ELISA and immunoblotting quantification of the enriched media reflected the observations made in vivo. Specifically, ELISA measurements (FIG. 4D) underestimated the amount of IGF-I produced by constructs when there was gly-pro-IGF-I present, compared to quantification by immunoblotting (FIG. 4E, F). Therefore, while ELISA is a robust measurement for mature IGF-I, the presence of additional forms of IGF-I impairs the accurate quantification of the total IGF-I pool. Further, the denatured conditions used in immunoblotting provided a more accurate measurement for all IGF-I forms produced.

To determine the potency for IGF-IR activation by each IGF-I form, media from the transfected 3T3 cells were utilized for KIRA assays (FIG. 5A). Compared to mature IGF-I, it was found that media containing gly-pro-IGF-I had lower apparent IGF-IR activation. Specifically, IGF-IA and IGF-IKRR samples caused 30% less IGF-IR phosphorylation per IGF molecule than mature IGF-I. In contrast, media containing predominantly pro-IGF-I following IGF-INN and IGF IKRRNN transfections had equivalent IGF-IR phosphorylation to mature IGF-I. To determine if the difference in IGF-IR phosphorylation was affected by a change in binding proteins, media content of IGFBP3 was evaluated by immunoblotting. However, there was no detectable IGFBP3 in the concentrated media. Thus, it appeared that gly-pro IGF-I was less able to activate the IGF-IR independent of changes in binding protein levels. Because many of the enriched media samples contained multiple forms of IGF-I, we took advantage of knowing the proportion of each species (FIG. 4B) and the apparent receptor activation to calculate the contribution of each IGF-I form to the final IGF-IR response by setting up a series of simultaneous equations, and solving for apparent activity of mature, pro-, and gly-pro-IGF-I in each replicate (see above series of equations). As shown in FIG. 5B, it was found that pro-IGF-I can activate the IGF-IR as well as mature IGF-I, yet gly-pro-IGF-I was 2-fold less potent than mature IGF-I. Therefore, both mature and pro-IGF-I are ligands for the IGF-IR, whereas gly-pro-IGF-I may serve as a reservoir for IGF-I that can be stored in the ECM until needed, when the glycosylated C-terminus is removed to release mature IGF-I.

DISCUSSION

Other goals of the disclosed subject matter were to identify the species of IGF-I produced in muscle, and to clarify which of these species were able to activate the IGF-IR. It was found that much of the IGF-I retained in muscle was pro-IGF-I, and when glycosylation was possible as in IGF-IA, gly-pro IGF-I and pro-IGF-I were present at similar levels. Cell-based assays for IGF-IR activation demonstrated that pro-IGF-I was just as efficient at receptor activation as mature IGF-I, yet gly-pro-IGF-I was significantly less effective per molecule to activate the receptor. The disclosed subject matter is the first to distinguish the potency of the different species of IGF-I produced, and establishes new ways to improve IGF-I activity.

Previous in vivo studies found that there was differential ability for the IGF-I isoforms to mediate muscle hypertrophy. Specifically, muscle specific viral expression of mature IGF-I did not promote increased muscle mass in contrast to IGF-IA or IGF-IB, even though there was more IGF-I produced by the AAVIGF-ISt (21). These comparisons were based on ELISA measurements of IGF-I, and so in retrospect, the amount of IGF-I produced by IGF-ISt was much lower than that produced by the IGF-IA or IGF-IB viral constructs. Further, since it has been found that pro-IGF-I and mature IGF-I are both strong ligands for the receptor, it is likely that both pro- and mature IGF-I contributed to the enhanced hypertrophic response in muscle overexpressing IGF-IA or IGF-IB.

The additional production of gly-pro-IGF-I by IGF-IA expression may act as a ligand reservoir; because it is less efficient at activating the IGF-IR, the glycosylation of the E-peptide may inhibit receptor binding. Although the crystal structure of mature IGF-I, as well as mutational analysis of the protein, clearly delineate the surface in mature IGF-I that is important for ligand binding (24, 25), the structure of the E-peptide extension has not been resolved. The KIRA measurements described herein indicate that the EA—peptide glycosylation covers the ligand binding site in the native state. However, while the non-glycosylated E-peptide in the pro-IGF-I species may also have a similar conformation, it does not appear to impede receptor phosphorylation. The recent development of PEGylated IGF-I also supports that a C-terminal extension does not necessarily block ligand binding, which is consistent with our prior observations (20). However, the affinity of the PEG-IGF-I was less than that of mature IGF-I, indicating that it may be more similar to gly-pro-IGF-I.

Although the in vivo measurements show stable accumulation of the pro- and gly-pro-IGF forms in the muscle lysates, it cannot be definitively stated that the entire IGF-I pool is in the extracellular matrix. Classically, IGF-I post-translational processing includes intracellular cleavage of the mature IGF-I from the E-peptide, leading to secretion of the mature peptide, and an unknown destination for the E-peptide (10). However, the highly orchestrated process of glycosylation poses another order of complexity onto IGF-I processing. The forms we have observed do not appear to be misfolded proteins destined for degradation, but instead appear to be stable intermediates or final products of post-translational processing, given that the furin and glycosidase digests confirm the identity of each band. Further, cell-based measurements described herein clearly show that all IGF-I species can be secreted, and substantiate the observations of pro-IGF-I in cell media previously reported (10, 12, 13, 23). In fact, most of the IGF-I is pro-IGF-I or gly-pro-IGF-I in the media from IGF-IA transfected cells, suggesting that only a small portion of IGF-I cleavage occurs intracellularly, or that cleavage occurs outside of the cell. In addition, comparison of the media from IGF-IA and IGF-INN transfections show that blockade of glycosylation did not affect the final amount of mature IGF-I secreted. This indicates that the cell may reserve ~25% of the nascent IGF-I pro-peptides for intracellular cleavage, and the rest is directed for glycosylation and/or secretion. The fate of the remaining IGF-I pool also appears to be tightly regulated. Of the total pro-IGF-I+gly pro-IGF-I pool produced by IGF-IA, ~75% is glycosylated, which is similar to the glycosylated proportion of IGF-I secreted following IGF-IKRR transfection. If this regulated processing is also true for muscle, then the predominant species of IGF-I would be glycosylated, and potentially stored in the ECM for subsequent activity by cleavage. In fact, the detectable endogenous IGF-I forms in muscle are also likely to be glycosylated, based on their molecular weight, which is consistent with this model.

The murine IGF-IA has two potential N-glycosylation sites, N92 and N100, both of which follow the consensus sequence NXS/T, where X can be any residue except proline. In humans and non-human primates, only the sequence surrounding N 92 is conserved (26), suggesting that if the same glycosylation patterns occurred in all species, N100 may not be utilized. Therefore, it was anticipated that mutation of N92 would block glycosylation, whereas mutation of N100 would not. However, site-directed mutagenesis of either asparagine only removed the presence of the faint bands above 17 kD, and instead the migration patterns of N92A and M100A mutants were indistinguishable. Only when both sites were mutated did all gly-pro-IGF-I bands disappear. Based on these results, it appeared that both residues can be glycosylated in mouse 3T3 cells, and so in order to generate pro-IGF-I for the KIRA assay, the double mutant was used. Differential glycosylation of IGF-I may occur in different tissue types, and provide another point for regulating stability and/or local retention of the growth factor.

The KIRA assays described herein compared all of the potential IGF-I forms produced by IGF-IA, because ~90% of all Igf1 transcripts are produced from this splice form. However, because IGF D3 lacks glycosylation, and muscle also produces predominantly pro-IGF-I following viral delivery of IGF-IB, this suggests that pro-IGF-IB may have similar receptor binding activity to pro-IGF-IA. Thus, the premise that IGF-IB is more "potent" than IGF-IA in terms of its actions may simply be due to the production of pro-IGF-I instead of gly-pro-IGF-I. This is similar to our results obtained from transfection of IGF-INN and IGF IKRRNN, which had better activation of the IGF-IR than IGF-IKRR or IGF-IA.

How the pro- and gly-pro-IGF forms reside in the muscle matrix is to be determined. Without wishing to be bound by any particular theory, like the receptor binding assays, these forms may be able to associate with IGF binding proteins, which are known stabilizers of IGF-I. Although there was no apparent change in the level of IGFBP3 in conditioned media, this does not address differential binding affinity of the various forms of IGF-I. The glycosylated residues may also associate directly with the ECM, serving as an alternate additional reservoir of this growth factor. Cleavage of the entire E-peptide by extracellular proteases can then release active mature IGF-I for receptor binding when needed. Alternatively, the glycosylation can be clipped from the core protein, releasing pro-IGF-I for receptor activation. There is evidence for candidate furin like proteases residing in the ECM that can cleave mature IGF-I from the E-peptide. PACE4, a member of the subtilisin-like proprotein convertases, is a likely candidate to cleave pro-IGF-I, given the importance of PACE4 for skeletal muscle differentiation (27), and the fact that this class of protease can perform the same reaction intracellularly (10). However, there is little evidence for extracellular glycosidases that can achieve the alternative path of regulation, and remove glycosylation from the IGF-I C-terminus.

In summary, multiple species of IGF-I have been identified that are produced by muscle both endogenously and following viral expression of IGF-IA and IGF-IB. The major forms that accumulate in the tissue are not mature IGF-I, but instead pro-IGF-I and gly-pro-IGF-I. In addition, it has been shown that the species of IGF-I produced by the Igf1a isoform have differential ability to activate the IGF-I receptor, where pro-IGF-I and mature IGF-I are more efficient at receptor activation than glycosylated pro-IGF-I.

Example 2: Viral Expression of Igf-I E-Peptides Increases Skeletal Muscle Mass

Figures 8A, 8B:
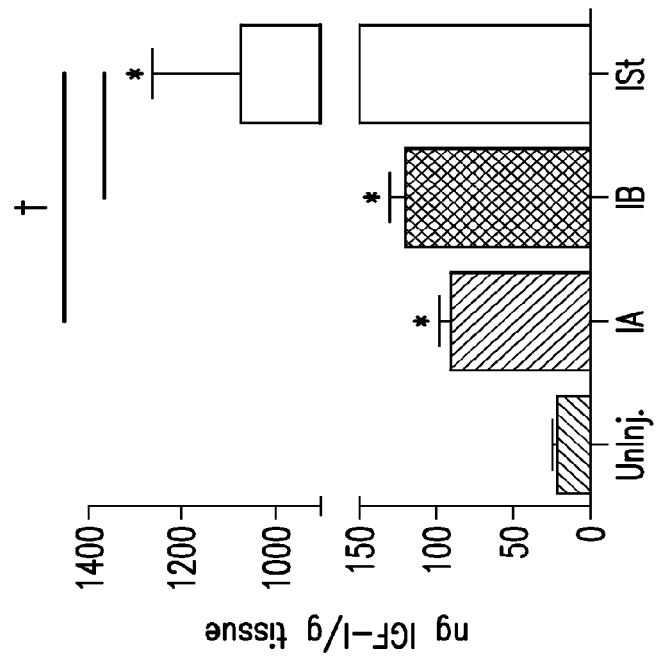
FIG. 8A-8D. AAV IGF-I V44M isoform injections lead to increased IGF-I production in muscle. A. IGF-I V44M isoforms were cloned into pAAV-CB plasmids for AAV generation. ITR, AAV inverted terminal repeat sequence; CMV, cytomegalovirus; SV40, Simian virus 40; BGH, bovine growth hormone. B. IGF-I ELISA on TA muscles 1 month after AAV injection. Bars represent means±s.e.m. of N=5 muscles per injection. *, $p<0.05$, for comparisons to Uninjected or †, $p<0.05$, for comparisons to ISt V44M via 1-way ANOVA followed by a Tukey post-test. C. IGF-I V44M isoform immunoblot. Lysates from TA muscles injected with IGF-I V44M AAVs and 2 ng recombinant IGF-I were immunoblotted with antibodies specific to IGF-I, EA, and EB to confirm the expression of the correct isoforms. GAPDH was used as a loading control. NoInj.=muscle not injected with AAV. D. Immunohistochemistry using EA and EB specific antibodies on AAV injected EDL muscle sections. Green=dystrophin, Blue=DAPI, Red=EA or EB. Scale bar=60 µm.

Materials and Methods:
Igf-I V44M Plasmids.
IGF-I isoform constructs in pIRES plasmids were previously described [28]. The plasmids were mutated at Valine 44 to Methionine by site-directed mutagenesis (QuikChange II, Stratagene). The IGF-I V44M constructs were then sub-cloned into pAAV-CB plasmids for vector generation (FIG. 8a).

Viral Injections.
All experiments were approved by the University of Pennsylvania animal care committee. AAV serotype 2/8 vectors expressing the IGF-I V44M isoforms were generated by the Children's Hospital of Philadelphia Vector Core.

Viral injections of 5×10$^{10}$ particles diluted in 50 µl of phosphate-buffered saline (PBS) were performed into the anterior compartment of the lower hindlimbs of anesthetized C57Bl/6 (C57) and MKR [29] mice targeting the tibialis anterior (TA) and extensor digitorum longus (EDL) muscles. For IA and IB V44M injected mice, the right limb was injected with ISt V44M to serve as a contralateral control. In addition, a cohort of mice was injected with ISt V44M in one limb and needle-prick only (no injection) in the other. After injection, mice were housed in the animal facility until time of analysis. They were sacrificed 1 week, 1 month, or 3 months after injection. The TA muscles were dissected and rapidly frozen in liquid nitrogen for biochemical analysis, while the EDL muscles were subjected to force measurements (described below).

Cell Transfection.

Reverse transient transfection of 3T3 cells with pIRES plasmids containing IGF-I isoform constructs was performed using Lipofectamine 2000 (Invitrogen). Controls included transfection of empty vector (GFP). 24 hours after transfection, conditioned media from transfected 3T3 cells was utilized in kinase receptor activity assays as previously described [30, 31]. 3T3 cell pellets were also retained for GFP immunoblotting to measure transfection efficiency.

IGF-I ELISA.

Total IGF-I content in muscle protein extracts was determined by a standard sandwich ELISA protocol using commercially available kit (MG100, R&D Systems) according to manufacturer's recommendations and as previously described [32, 28].

Analysis of Muscle Contraction.

EDL muscle strength was analyzed as previously described [26] and CSA was measured as in [53]. After force measurements were completed, the muscles were removed from the bath, blotted, weighed, pinned at optimum length, surrounded by OCT embedding compound (TissueTek, Sakura), and rapidly frozen in melting isopentane. Muscles were stored at −80° C. for subsequent analysis.

Immunoblotting.

Tissues and cells were processed for immunoblotting as previously described [36]. The following primary antibodies were used for the immunodetection: IGF-I (AF791; R&D Systems); EA [30]; EB [54]; GAPDH (sc-32233, Santa Cruz Biotechnology); P-Akt (no. 9271) total Akt (no. 2920), P-ERK1/2 (no. 9101), total ERK1/2 (no. 9102), and GFP (no. 2955) (Cell Signaling).

Immunohistochemistry.

Frozen cross-sections (10 µm) from the midbelly of EDL muscles were stained for laminin (rabbit Ab-1; Neomarkers) or dystrophin (VP-D505, Vectorlabs) to outline the muscle fibers. Fibers were fiber-typed with antibodies recognizing myosin heavy chain (MHC) 2A (SC-71), MHC 2B (BF-F3), and MHC 1/β (BAF-8) (Developmental Studies Hybridoma Bank). Myofiber area was measured in EDL sections (all fibers measured, ~1000 fibers per muscle) at 100× magnification. For satellite cells, sections were first dried at room temperature and then fixed in 2% formaldehyde for 10 min. Slides underwent dehydration and rehydration in ethanol, permeabilization for 10 minutes in 0.5% Triton X-100, boiling for 20 minutes in 10 mM sodium citrate, followed by staining using the mouse-on-mouse staining kit (Vector labs) and antibodies towards Pax7 (MAB1675, R&D Systems) and Ki67 (ab15580, Abcam). Nuclei were counterstained with DAPI. Stained sections were visualized on a Leica DMR microscope, and digital images were analyzed using OpenLab software (Improvision).

Glucocorticoid Atrophy.

Two weeks after AAV injection, mice were treated with Dexamethasone (DEX; D2915 Sigma) as described previously [33] for 14 days in drinking water. Effectiveness of treatment was verified by measurement of body and spleen weight, which decrease with glucocorticoid treatment.

Statistical Analysis.

All data was analyzed via student t-tests (paired and unpaired), or 1-way ANOVA followed by a Tukey post-test. Statistical significance was accepted at $p<0.05$.

Results

Figure 7A:
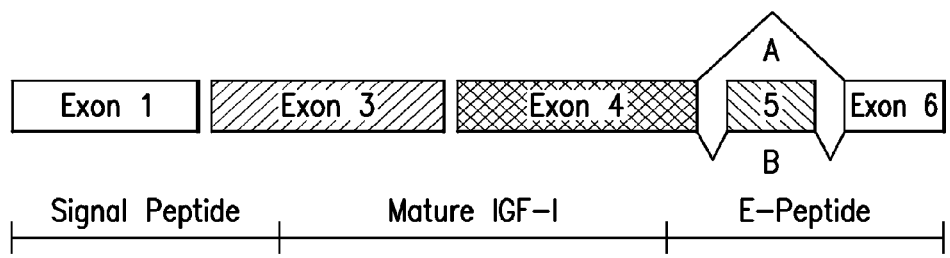
FIG. 7A-7C. IGF-I V44M isoform constructs do not activate IGF-IR. A. Alternative splicing at the 3' end of the murine Igf1 gene generates two isoforms: Igf1a and Igf1b. Igf1a isoforms splice from exon 4 to exon 6, while isoform Igf1b includes exon 5, leading to an altered reading frame and earlier stop codon in exon 6. Exons not drawn to scale. B. cDNA constructs generated to express V44M versions of IA, IB, and IStop (ISt, stop codon after IGF-I, no E-peptide). Dotted lines indicate mature IGF-I boundaries. C. Ability of IGF-I and IGF-I V44M isoforms to activate IGF-IR. Conditioned media from transfected 3T3 cells were used to stimulate IGF-IR over-expressing fibroblasts (P6 cells), and IGF-IR phosphorylation was measured using a kinase receptor activation ELISA assay and normalized to GFP protein expression (immunoblot not shown) to control for transfection efficiency. GFP, transfection with empty plasmid. Bars represent means±s.e.m. of N=3 replicates. *, $p<0.05$, for comparisons between wildtype and V44M constructs via student unpaired t-tests.
Figure 7B:
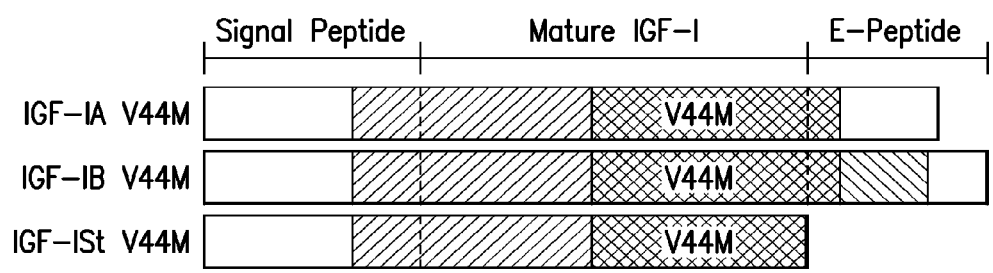

Another goal of the disclosed subject matter was to examine the function of the E-peptide in skeletal muscle. In addition to post-translational processing producing different IGF-I forms, alternative splicing of Igf1 also generates distinct isoforms (FIG. 7A). In the rodent, there are two isoforms, IGF-IA (IA) and IGF-IB (IB) [13, 14] (FIGS. 7A and B). Splicing only alters the E-peptide sequence, giving rise to EA and EB peptides from IA and IB. The predominant Igf1 mRNA isoform expressed is Igf1a, which is 90-99% of the transcripts, and it is the most conserved across all species examined [15, 16].

To evaluate the physiological impact of E-peptide activity in skeletal muscle, and to understand the mechanisms underlying these actions, EA and EB expression, was compared in vivo without expressing functional IGF-I. A naturally occurring mutation in humans (Valine 44 to Methionine, V44M) which renders the IGF-I non-functional [31], but ensures normal production of the E-peptides was used in the disclosed subject matter.

Figure 7C:
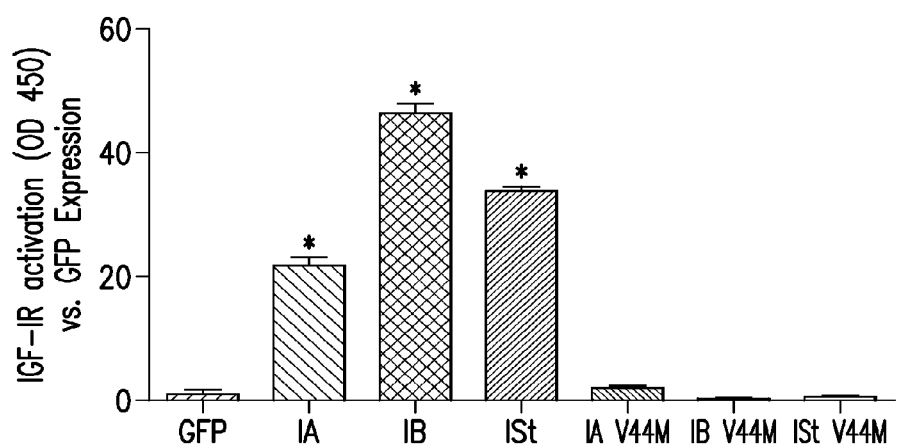

To express the E-peptides in their native form without increasing the levels of mature IGF-I, IGF-I constructs harboring the V44M mutation were generated [31], which is conserved in murine Igf1. Murine IGF-I expression vectors [28] were mutated to generate V44M forms of IA, IB, and ISt, where ISt lacked any E-peptide (FIGS. 7A and B). To confirm that rodent IGF-I V44M may not activate IGF-IR, all constructs were transfected into 3T3 cells, and used the conditioned media for IGF-IR specific kinase receptor activation assays [31] (FIG. 7C). While wildtype IA, IB, and ISt constructs led to robust IGF-IR phosphorylation, the V44M constructs failed to activate IGF-IR. Thus, IGF-I V44M is effectively non-functional.

To express the E-peptides in vivo, self-complementing AAV [34] harboring the V44M cDNAs were generated (FIG. 8A). Anterior hindlimbs of young (2-3 week old) C57 mice were injected with AAV-IGF-I V44M isoforms IA, IB, or ISt, targeting tibialis anterior (TA) and extensor digitorum longus (EDL) muscles. 1 month after injection, all three V44M IGF-I isoforms produced more IGF-I than uninjected limbs when measured by ELISA (FIG. 8B); however, the ISt V44M construct produced 10-fold more IGF-I than IA or IB V44M.

Figure 8D:
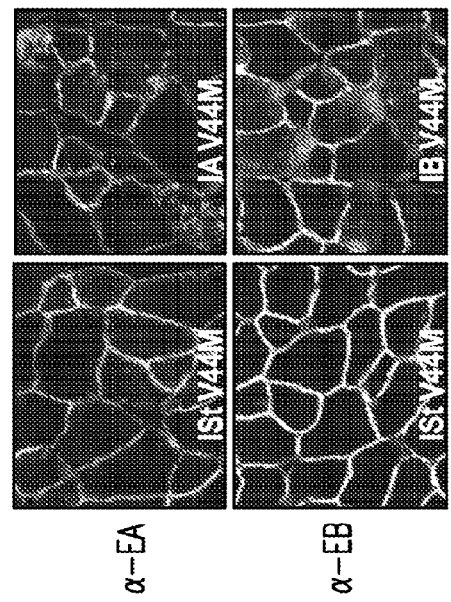
Figure 8C:
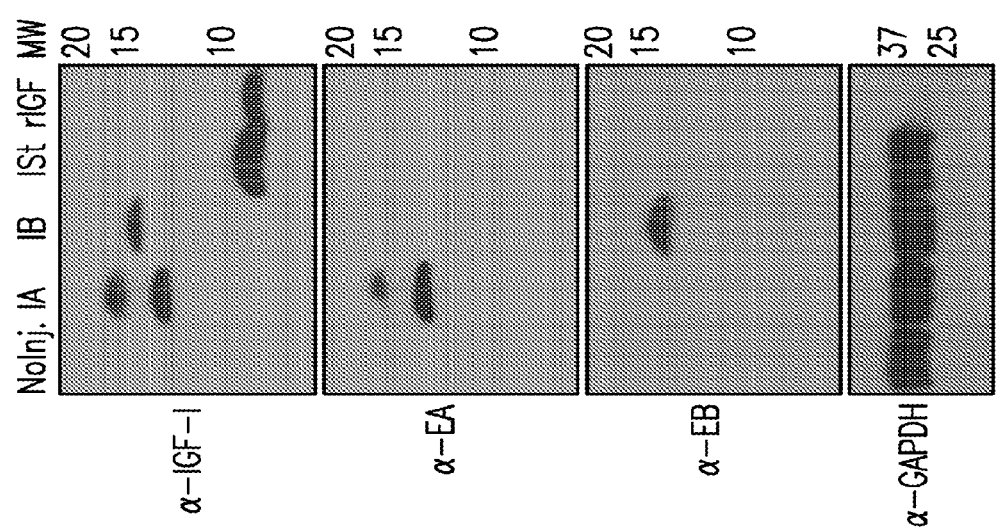

To confirm that the correct forms of IGF-I were produced, muscle lysates were immunoblotted using IGF-I, EA, and EB-specific antibodies (FIG. 8C). In contrast to the ELISA measurements, there were roughly equivalent levels of IGF-I production from each viral construct. The IGF-I antibody reacted strongly with bands in ISt, IA, and IB V44M lanes. ISt produced a band at 7-8 kD, the size of mature IGF-I in serum and tissues [35], which was not immunoreactive with anti-EA or anti-EB. IA V44M had multiple bands from 11-18 kD detected by both anti-IGF-I and anti-EA. These bands represent pro-IA, and glycosylated pro-IA [36, 37]. A single 14 kD band in the IB V44M lane was detected with anti-IGF-I and anti-EB, and represents pro-IB. Neither the ~3-6 kDa free E-peptides nor the mature IGF-I produced from cleavage of pro-IGF-I were detectable by immunoblotting, consistent with the normal pattern of IGF-I forms in skeletal muscle [36]. Based on the sizes and antibody reactivity, AAV IGF-I V44M injections produced the correct IGF-I isoforms. Localization of E-peptides in injected muscles was determined by immunohistochemistry with anti-EA and anti-EB (FIG. 8D). EA and EB were apparent in IA V44M and D3 V44M sections, respectively. Staining was restricted to within muscle fibers and was not found in the extracellular matrix (ECM). Staining of EA and EB was not detected in ISt V44M expressing muscles.

E-peptides modulate muscle cell signaling that relies on the IGF-IR. Namely, E-peptides increase MAPK signaling, but do not alter the PI3K/Akt pathway in myoblast cell culture, which are both downstream from IGF-IR activation [30]. To test if the E-peptides also activated these pathways in vivo, muscles were harvested 1 week after AAV injection (FIG. 9). Compared to sham injected muscles, ISt V44M did not alter P-ERK1/2 or P-Akt levels, further supporting the lack of activity of this mutant IGF-I. However, IA V44M expression caused significantly elevated P-ERK1/2 compared to ISt V44M, with an 8- and 3-fold increase in P-ERK1 and P-ERK2, respectively. Similarly, IB V44M expression resulted in a 2-fold increase in P-ERK1/2. Most interestingly, while IA V44M had no significant effect on the PI3K/Akt pathway, IB V44M expression resulted in a reduction of P-Akt compared to ISt V44M. Thus, both E-peptides modulated the MAPK and PI3K/Akt pathways in vivo consistent with in vitro observations.

Figure 13:
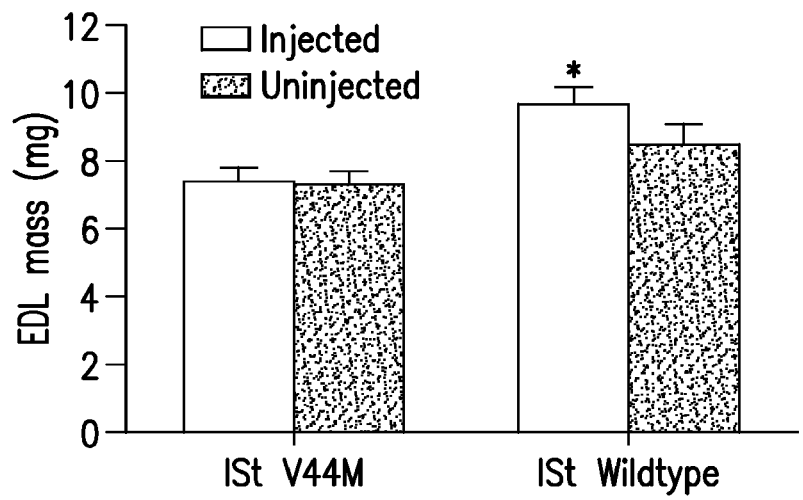
FIG. 13. ISt V44M is unable to induce muscle hypertrophy. EDL muscle mass 1 month after viral injections. Mice were injected with AAV vectors harboring either ISt V44M or wildtype ISt in one limb, with no viral injection in the contralateral limb. Bars represent means±s.e.m. of N=7-8 mice per test injection. *, p<0.05, for comparisons to Uninjected control limbs via paired t-tests.
Figure 14:
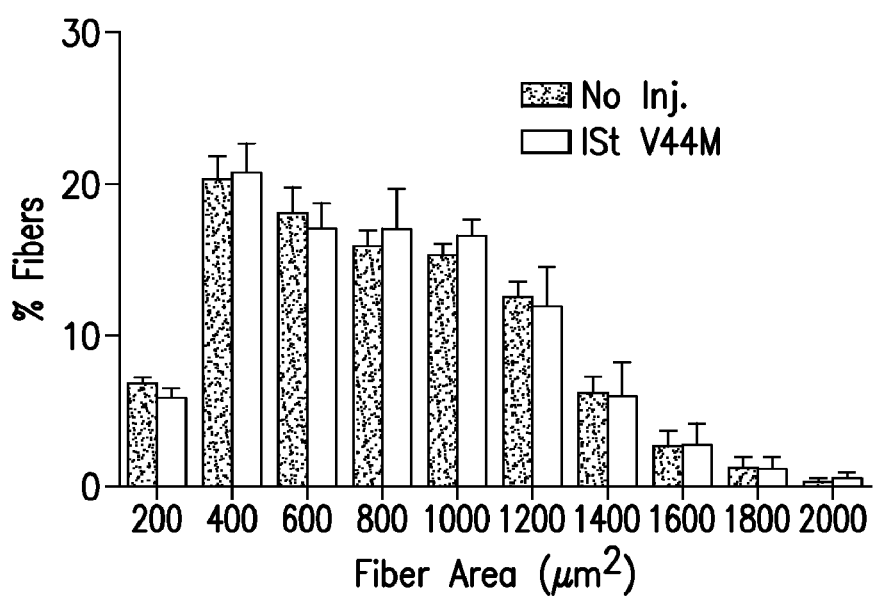
FIG. 14. ISt V44M does not affect myofibers area. Sections of AAV V44M injected EDLs were stained for dystrophin to outline muscle fibers. The areas of all the fibers in the EDLs (~1000 fibers on average per EDL) were measured and histograms were generated representing the proportion of fibers at a certain size.

In order to assess the physiological effects of E-peptide expression, the same design was employed as with signaling measurements, but muscles were analyzed 1 month post-injection. EDL muscle mass after viral injection of ISt V44M were first compared to wildtype ISt (FIG. 13). Wildtype ISt expression resulted in ~16% increase in muscle size, supporting that this delivery method was effective. Confirming its inactivity, ISt V44M expression failed to change muscle mass. These measurements were extended to all V44M constructs, where mass, cross-sectional area (CSA), and isometric force were analyzed in the EDL muscles (Table 3 and FIGS. 10A, E, and I). ISt V44M injected limbs were not significantly different from uninjected limbs in any of the parameters analyzed, confirming that mature IGF-I V44M was non-functional in vivo. IA V44M expression did not increase muscle mass significantly, but improved muscle strength compared to ISt V44M injected muscles in the same animal. In contrast, D3 V44M expression resulted in a 5-6% increase in mass and CSA, with a commensurate increase in force production and similar specific forces to ISt V44M injected muscles. Thus, at 1 month, both E-peptides were driving beneficial effects on mass and/or function.

Figure 10L:
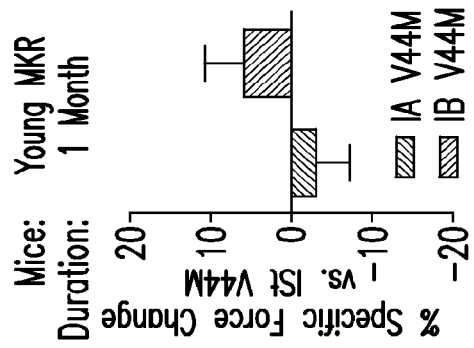
Figure 10K:
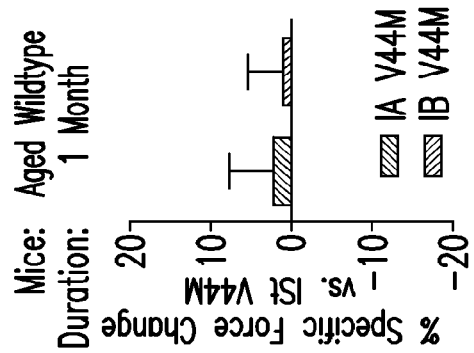
Figure 10J:
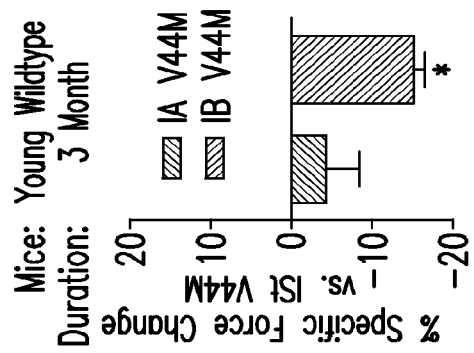
Figure 10I:
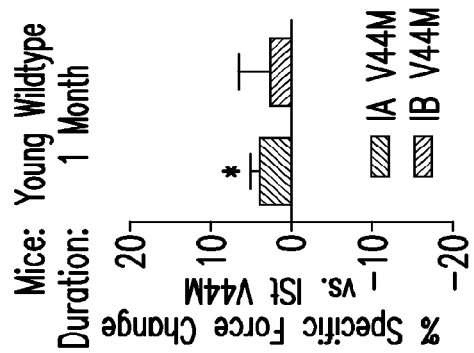

To determine the persistence of these effects, muscles were analyzed 3 months after injection (Table 3 and FIGS. 10B, F and J). Here, IA V44M injected EDLs were larger than ISt V44M injected contralateral muscles, with a significant increase in CSA (~6%, FIG. 11F). The effects of D3 V44M expression also continued to build, with a 10% CSA and over 6% mass increase compared to ISt V44M (FIGS. 10B and F). However, D3 V44M expression was associated with reduced function at this timepoint, where injected EDLs were weaker than controls in both tetanic and specific force (Table 3 and FIG. 10J). Thus, although the muscles were larger, sustained EB expression negatively affected muscle strength.

As previously observed, mature murine muscle did not respond to viral expression of wildtype IGF-IB, which was presumed due to the need for an active satellite cell pool for this isoform to promote hypertrophy [32]. To address if this was also required for the E-peptide actions, aged wildtype mice (1 year old) were injected with the V44M AAVs. No isoform had an effect on any of the parameters measured (Table 3 and FIGS. 10C, G, and K), showing that only young muscle responded to E-peptides at 1 month post-injection.

In cell culture, EB requires a functional IGF-IR to increase myoblast MAPK signaling, proliferation, and migration [30]. Accordingly, to determine if EB activity in vivo, namely muscle hypertrophy, also requires IGF-IR, young MKR mice, which express a dominant negative IGF-IR in mature skeletal muscle, were injected for 1 month [38]. In muscle without functional IGF-IR, neither EA nor EB had any effects on muscle size or strength (Table 3 and FIGS. 10D, H, and L). Consistent with cell culture data [30], E-peptide activity in vivo requires functional IGF-IR.

TABLE 3

| AAV Injection | Uninjected | ISt V44M | IA V44M | ISt V44M | IB V44M | ISt V44M |
|---|---|---|---|---|---|---|
| Wildtype 1 month | | | | | | |
| Mass (mg) | 7.33 ± 0.38 | 7.44 ± 0.39 | 8.03 ± 0.43 | 8.10 ± 0.65 | 7.90 ± 0.24* | 7.55 ± 0.26 |
| CSA (mm$^2$) | 1.25 ± 0.02 | 1.29 ± 0.04 | 1.37 ± 0.06 | 1.41 ± 0.07 | 1.32 ± 0.05* | 1.25 ± 0.05 |
| Tetanic Force (mN) | 293.67 ± 7.43 | 319.26 ± 13.33 | 364.39 ± 29.45 | 361.96 ± 31.14 | 330.63 ± 21.47* | 313.50 ± 19.06 |
| Specific Force (N/cm$^2$) | 23.32 ± 1.00 | 23.95 ± 0.66 | 26.02 ± 1.05* | 25.06 ± 0.95 | 24.86 ± 0.84 | 25.04 ± 0.79 |
| Wildtype 3 month | | | | | | |
| Mass (mg) | ND | ND | 9.61 ± 0.45 | 9.37 ± 0.42 | 9.43 ± 0.24* | 8.85 ± 0.31 |
| CSA (mm$^2$) | ND | ND | 1.58 ± 0.06* | 1.50 ± 0.07 | 1.53 ± 0.05* | 1.39 ± 0.06 |
| Tetanic Force (mN) | ND | ND | 390.94 ± 22.41 | 388.78 ± 18.86 | 350.41 ± 17.57* | 376.24 ± 18.24 |
| Specific Force (N/cm$^2$) | ND | ND | 24.63 ± 0.73 | 25.94 ± 1.01 | 22.94 ± 0.96* | 27.07 ± 0.91 |
| Aged Wildtype 1 month | | | | | | |
| Mass (mg) | 12.10 ± 0.45 | 12.17 ± 0.47 | 12.95 ± 0.44 | 12.97 ± 0.23 | 12.31 ± 0.40 | 12.14 ± 0.47 |
| CSA (mm$^2$) | ND | ND | 1.89 ± 0.07 | 1.91 ± 0.04 | 1.79 ± 0.06 | 1.77 ± 0.05 |
| Tetanic Force (mN) | ND | ND | 479.82 ± 6.54 | 481.55 ± 22.13 | 454.75 ± 10.18 | 450.55 ± 18.91 |
| Specific Force (N/cm$^2$) | ND | ND | 25.58 ± 0.95 | 25.23 ± 1.08 | 25.55 ± 0.52 | 25.57 ± 1.20 |
| MKR 1 month | | | | | | |
| Mass (mg) | 5.30 ± 0.99 | 5.38 ± 0.883 | 5.74 ± 0.44 | 5.83 ± 0.37 | 5.77 ± 0.31 | 5.70 ± 0.38 |
| CSA (mm$^2$) | ND | ND | 0.94 ± 0.04 | 0.94 ± 0.05 | 1.01 ± 0.05 | 1.04 ± 0.09 |
| Tetanic Force (mN) | ND | ND | 242.15 ± 20.60 | 247.79 ± 12.68 | 262.71 ± 21.09 | 255.10 ± 23.97 |
| Specific Force (N/cm$^2$) | ND | ND | 25.63 ± 0.95 | 26.43 ± 0.42 | 25.82 ± 0.83 | 24.44 ± 0.82 |

Data are means ± s.e.m. of N = 5-8 EDL muscle pairs per injection.
*p < 0.05, for comparisons to ISt V44M contralateral control EDLs via paired t-tests.
ND, not determined; CSA, cross-sectional area.

Figure 11D:
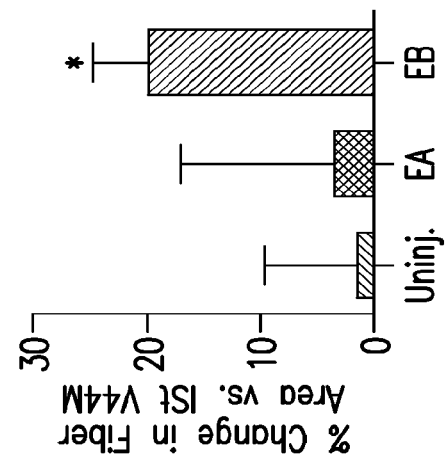
Figure 11E:
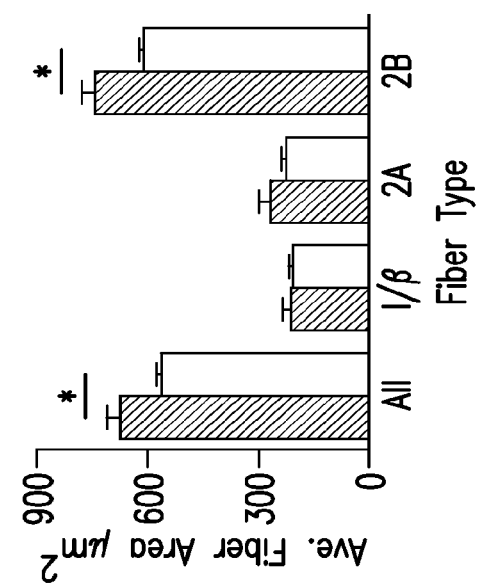

Muscle mass can increase either through changes in muscle fiber size, or in fiber number. To determine how the E-peptides affected mass, sections from EDL muscles were labeled with dystrophin to outline muscle fibers (FIG. 11A). Neither ISt nor IA V44M affected fiber area, but IB V44M expression caused a rightward shift in the size distribution, resulting in a 20% increase in mean fiber size compared to ISt V44M injected muscles (FIG. 11B, C, D and 14). There was no apparent change in fiber number in any treatment group. To determine if the change in fiber size was associated with a specific fiber type, the areas of MHC1/β, 2A, and 2B fibers were measured. The average fiber size of 2B fibers was significantly larger following IB V44M expression than ISt V44M controls by 25%, but 1/(3 and 2A fibers were not significantly affected (FIG. 11E), indicating that EB induced hypertrophy predominantly affects 2B fibers.

Figure 11F:
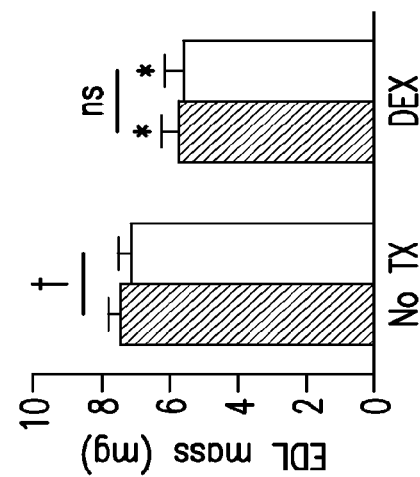

The fiber type specific hypertrophy from D3 V44M expression raised the possibility that the EB-peptide can also provide protection against MHC 2B fiber-specific atrophy. Glucocorticoids like dexamethasone (DEX) cause general atrophy in mice, but in muscle, 2B fibers are the most affected fiber type [39]. Wildtype mice were injected with IB V44M in one limb and ISt V44M in the contralateral limb for 1 month, and two weeks before dissection, mice were treated with DEX or vehicle (FIG. 11F). DEX treatment caused a reduction in body, spleen, and EDL mass (31%, 50%, and 25% respectively). D3 V44M expression caused a ~5% increase in EDL mass in vehicle treated mice. However, D3 V44M expression did not increase mass of DEX treated muscles. Both ISt and IB V44M injected limbs were smaller in DEX treated mice, and so even though IB V44M can cause hypertrophy in healthy muscle, it cannot block glucocorticoid induced atrophy.

Figure 12D:
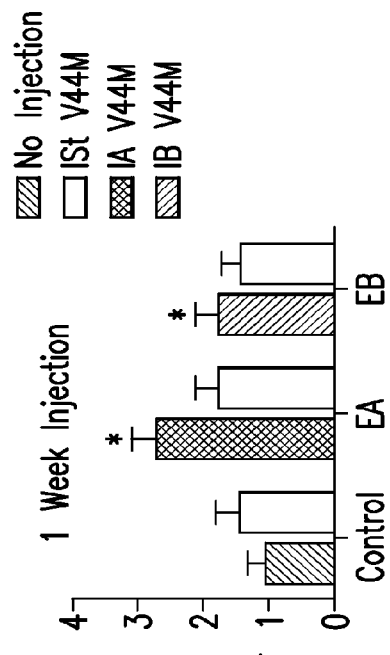
Figure 12F:
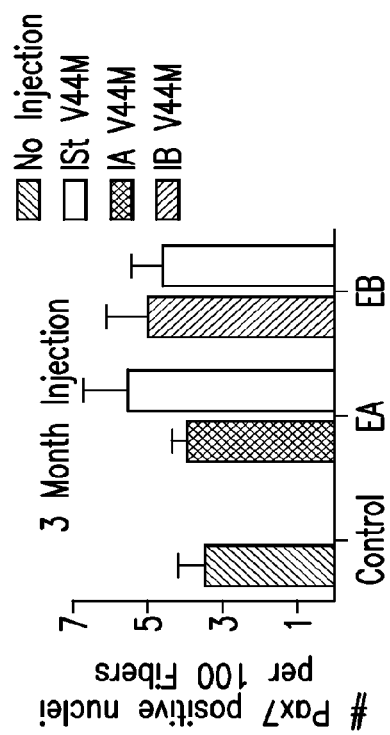
Figure 12E:
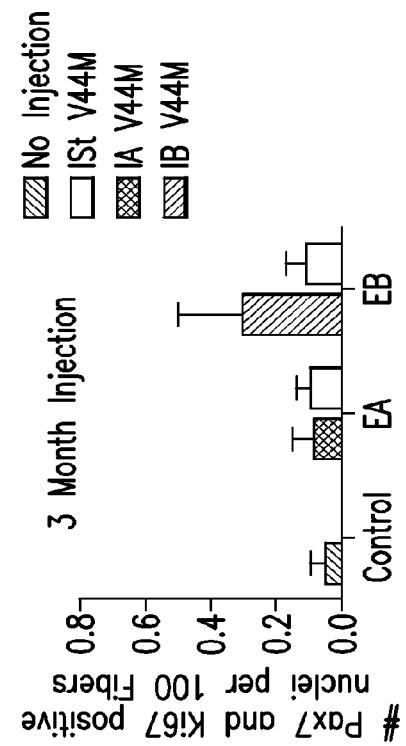
Figure 12G:
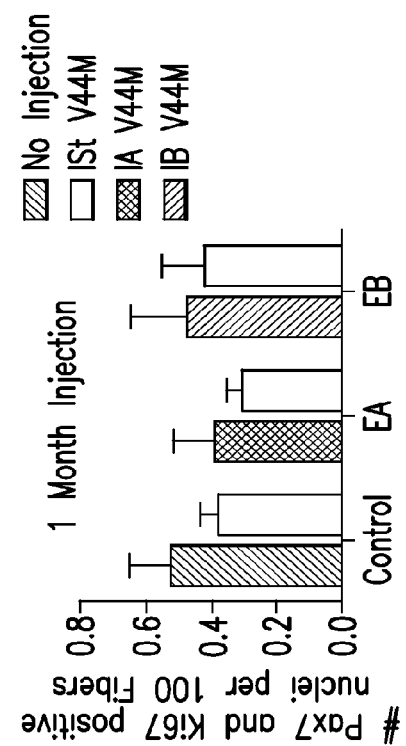

EB has been reported to activate satellite cells and increase proliferation in culture [40-43]. To examine if E-peptide expression altered satellite cell proliferation in vivo, satellite cell number (Pax7 positive), and proliferating satellite cells (Pax7 and Ki67 positive) were counted in EDL sections following IA, IB, or ISt V44M AAV injections (FIG. 12). ISt V44M expression did not affect satellite cell number or proliferation compared to uninjected controls. In contrast, both IA V44M and IB V44M caused an increase in the number of proliferating satellite cells 1 week after injection (FIG. 12E). However, at 1 month, there were fewer total satellite cells with no change in proliferation (FIG. 12C). By 3 months of expression, satellite cell depletion was resolved, and no differences in satellite cell number or proliferation were observed (FIGS. 12d and g). Thus, satellite cells may contribute to the E-peptide effects on growth, but appear to do so only transiently.

DISCUSSION

While it is straightforward to produce IGF-I in the absence of an E-peptide [44, 28], it has been more technically challenging to generate E-peptides in the absence of IGF-I so that their actions can be distinguished from that of the more well characterized growth factor. To overcome this hurdle, the V44M mutation was utilized to afford normal processing of the IGF-I precursor, block the activity of mature IGF-I, yet retain the potential activity of the E-peptides. Mature IGF-I harboring V44M was inactive in all parameters measured, including signaling, mass, function, and satellite cell activation, so ISt V44M can be utilized as a negative control for comparisons to those constructs retaining the E-peptides. Thus, the effects observed in muscle are due to the increased expression of the E-peptides.

The predominant forms of IGF-I that were detected by immunoblotting were pro-IGF-I. When injected muscle lysates were subjected to immunoblotting for EA or EB antibodies, the free E-peptides (3-6 kDa) were not seen, but neither was mature IGF-I. Although not limited to a particular theory, this suggests that the mutant IGF-I proteins are stored similarly to the endogenous pool, as pro- and glycosylated pro-peptides [36]. The levels of free E-peptides and mature IGF-I are likely to be below the limit of detection for immunoblots, but the stability of these factors is also a consideration, where protease cleavage can separate the E-peptides from the mutant IGF-I, and ultimately cause degradation of both products.

It has been suggested that the pro isoforms are stored outside of muscle fibers via the charged E-peptides associating with the ECM [47]. However, via immunohistochemistry, it was found that the E-peptides accumulated inside the muscle fibers, not outside in the ECM. Because these sections are only a single timepoint, it is unknown whether the intracellular localization represents a pool of the IGF-I forms that is destined for secretion from AAV transduced fibers, or if it represents internalized E-peptide following binding to cell surface receptors. Additional experiments are needed to resolve this issue.

The disclosed subject matter shows that muscle hypertrophy by E-peptide expression relied on functional IGF-IR, similar to the results obtained in vitro, although how the E-peptides mediate their effects through this receptor is still unclear. Without being limited to a particular theory, the disclosed subject matter suggests that the E-peptides enhance the activity of IGF-I, and that without any IGF-I present, there are no E-peptide actions [30]. In addition, the disclosed subject matter suggests that the E-peptides alter mature IGF-I binding to the receptor, and do not affect the receptor in the absence of IGF-I. Although only E-peptides were expressed the muscle stores IGF-I in the ECM, and there is also a constant source of IGF-I in the circulation. Therefore, it cannot be excluded that the E-peptides also rely on an endogenous source of IGF-I to mediate effects in vivo. Future studies can resolve this issue by combining viral expression of the E-peptides with animals lacking IGF-I [48].

The increase in mass observed after IB V44M expression is due to an increase in fiber size, and specifically in WIC 2B fiber size (FIG. 11). Even though average fiber size increased by 20%, whole muscle mass changed only by 5%. IGF-I treatment often has varying effects on mass vs. myofiber hypertrophy. While increased local expression of IGF-I leads to both enlarged muscle mass and fiber area [50], systemic delivery of recombinant IGF-I into wildtype mice leads to no significant change in muscle mass, but a 55% increase in average fiber area [49]. The fiber type specificity of hypertrophy does not appear to depend upon the exclusive expression of IGF-IR on 2B fibers, for the receptors are found on all fiber types [35]. Rather, a simpler explanation is that the ability for WIC 2B fibers to change size more dynamically than other fiber types affords a greater response to pro-growth signals. Similarly, the fact the EB expression failed to prevent glucocorticoid-induced atrophy also supports that there is no fiber type specificity for EB activity.

Expression of the E-peptides also led to changes in the strength of the muscles. EDLs injected with AAV IA V44M were stronger in specific force. IB V44M hypertrophy after 1 month was coupled with a rise in maximum Tetanic force, but after 3 months, force generating capacity was dramatically reduced. This implies that long-term expression of EB has detrimental effects on muscle architecture, although there was still hypertrophy. The fiber type specific hypertrophy combined with the loss of function is reminiscent of the effects of myostatin targeting. Muscles from myostatin null mice are much larger than wildtype muscles, but there is a reduction in muscle strength, coupled by an increase in 2B fiber size and proportion, and depletion of mitochondria [45]. While an increase in the proportion of 2B fibers was not observed, an increase in 2B fiber size was observed. Without being limited to a particular theory, one factor that may underlie diminished function in myostatin-null muscles is increased myonuclear domains, where each myonucleus must support a greater region of the fiber [46]. In contrast, transgenic expression of wildtype IGF-IA exhibits hypertrophy but maintains myonuclear domain. The transient increase in proliferating satellite cells suggests that an early trigger for satellite cell activation occurs, but may not continue throughout the 3 month duration.

For almost all parameters, EB expression generated greater effects than EA, but both caused similar changes to the muscle. Whether the E-peptides have differential potency, or completely different actions is still an open question. Although there is only 50% homology between the two peptides, a more significant difference may be the glycosylation of EA [37]. It has been reported that pro-IGF-IA is just as effective at receptor activation as mature IGF-I, but that glycosylation impairs its activity [36]. Since viral expression of IA V44M produced both non-glycosylated and glycosylated EA, then it is quite possible that only the non-glycosylated peptide was acting in a similar manner to EB. The alternative splicing that occurs on the 3' end of the Igf1 transcript may be a strategy to avoid E-peptide glycosylation. Future studies can test this through the removal of the glycosylation sites in the EA peptide.

The disclosed subject matter addressed whether or not E-peptides have physiological significance for skeletal muscle. It was found that the EB peptide, in particular, drives hypertrophy and that these pro-growth effects are dependent upon the IGF-IR. Further, only muscles from young growing mice respond to the E-peptides, suggesting that an active pool of satellite cells is also required their actions. Importantly, sustained expression of EB causes progressively more mass increase, and EA drives more modest changes in muscle size, but there is a loss of strength that appears 3 months after viral injection of EB. Without being bound to a particular theory, the functional consequences of persistently increased EB expression may override the potentially beneficial pro-growth effects of this peptide.

Without being bound to a particular theory, the therapeutic potential of E-peptides can be restricted to transient upregulation in muscle, rather than continuous delivery. It was found that there is pro-growth potential, but there is ultimately compromised function. As such, strategies to boost E-peptides only during recovery from disuse atrophy or from damage can be beneficial. Without being bound to a particular theory, the focus on EB as a beneficial agent to prevent sarcopenia may be misplaced [51]. While wildtype IA expression can return normal function to aged muscle [52], it was found that neither IB [32] nor EB expression leads to hypertrophy in aged muscles, and so they may require an activated satellite cell pool to have activity.

Example 3: Comparison of IGF-I Isoforms for Potency for Hypertrophy

Recombinant Adeno-associated virus (AAV2/8) harboring cDNAs encoding full length IGF-IA (IA), mature IGF-I (ISt), or pro-IGF-I (KN) were injected into mouse hindlimb muscles (N=3 per construct). The contralateral limbs were injected with AAV encoding the V44M mutant of IGF-I, which produces IGF-I, but it does not activate the IGF-I receptor. This injection controlled for viral load, for there is no change in mass associated with increased IGF-I V44M. At 1 month following injections, muscles were harvested to determine IGF-I content by immunoblotting, and change in muscle mass. As shown in FIG. 15, IGF-IA produced all three forms of IGF-I (glycosylated pro-IGF-I, pro-IGF-I and mature IGF-I), whereas the other injections produced a single form of IGF-I. The IGF-I content in each of the muscles was quantified (FIG. 16), and the KN (pro-IGF-I) construct produced ~25% less IGF-I than IGF-IA. Of note, the pro-IGF-I produced by IGF-IA was equivalent to the KN production.

Muscle mass was measured, and in all cases, the IGF-I forms produced significant hypertrophy compared to the limbs injected with the V44M mutant (FIG. 16). However, both IGF-IA and pro-IGF produced ~2-fold more mass increase than mature IGF-I. Two points can thus be made. First, it appears that the pro-IGF-I is more potent than either of the other constructs, if one compares the extent of hypertrophy normalized to IGF-I content. Second, while many forms are produced by IGF-IA, without being bound to any theory, it appears that glycosylation must impair activity, for even though there is a large proportion of glycosylated pro-IGF-I produced, there is no enhancement of hypertrophy over that produced by pro-IGF-I.

Example 4: Comparison of IGF-I and Pro-IGF-1 Activity

To consider the effects loss of IGF-I function in muscle, a mouse line where IGF production was inhibited specifically in skeletal muscle, through ablation of GRP94, was generated (55). These mice exhibited reduced IGF-I content in muscle, and also had diminished circulating IGF-I. Intriguingly, circulating IGF-I contained both pro- and mature IGF-I, and pro-IGF-I was virtually eliminated from the blood in GRP94 mutant animals. GRP94 mutant mice had smaller muscles, presumably due to the loss of local IGF-I production, and whole body growth was impaired as well. These results show that muscle IGF-I is a critical factor for local and global growth, and that circulating pro-IGF-I can have bioactivity.

Figure 17A:
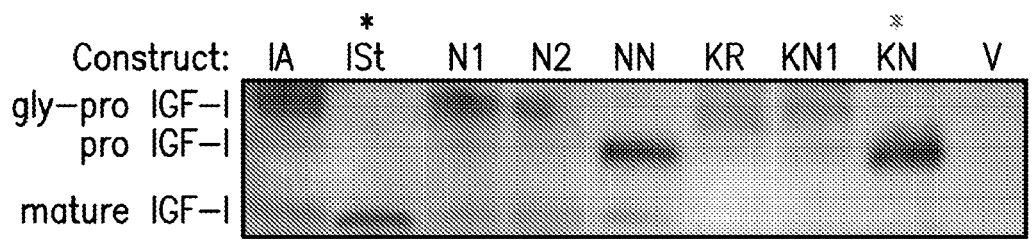
FIG. 17A-17B. Activity of IGF-IA forms. Forms of IGF-I secreted from transfected 3T3 cells, where ISt (*) is mature IGF-I. KN (*) harbors mutations of the convertase cleavage site and glycosylation sites to produce pro-IGF-I. Other constructs described in Durzynska et al, 2013. B. In KIRA assays, pro-IGF-I is 30% more potent at its maximum than mature IGF-I.
Figure 17B:
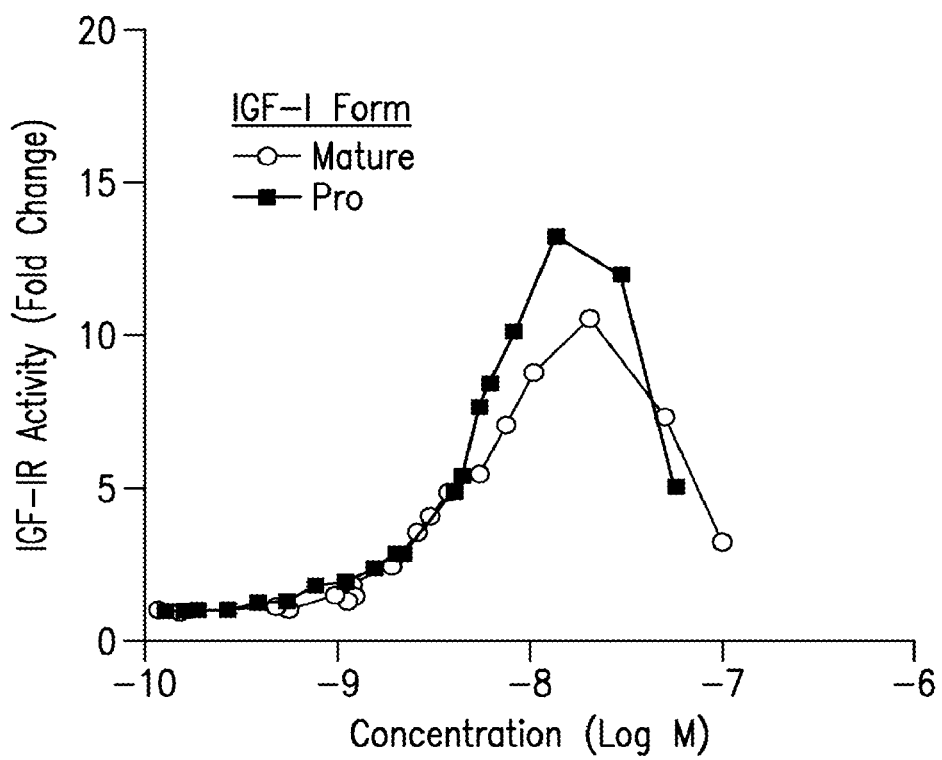

To determine if pro-IGF-I had receptor activity in vitro, a series of IGF-I mutants that lacked the E peptide, blocked cleavage between the mature IGF-I and the E-peptides, blocked N-glycosylation of the EA peptide, or both, were generated. All constructs were transfected into 3T3 cells, and conditioned serum-free media was harvested 24 hrs later. The forms produced from each construct were confirmed by immunoblotting (FIG. 17A). The purest forms produced by this method were mature IGF-I (ISt) and pro-IGF-I (KN), and these were analyzed further by Kinase Receptor Activation (KIRA) assays. The IGF-IR response to pro-IGF-I exceeded that of mature IGF-I by 30% (FIG. 17B) (56). These results indicate that multiple IGF-I forms are bioactive, and pro-IGF-I can represent a more potent form.

Figure 18:
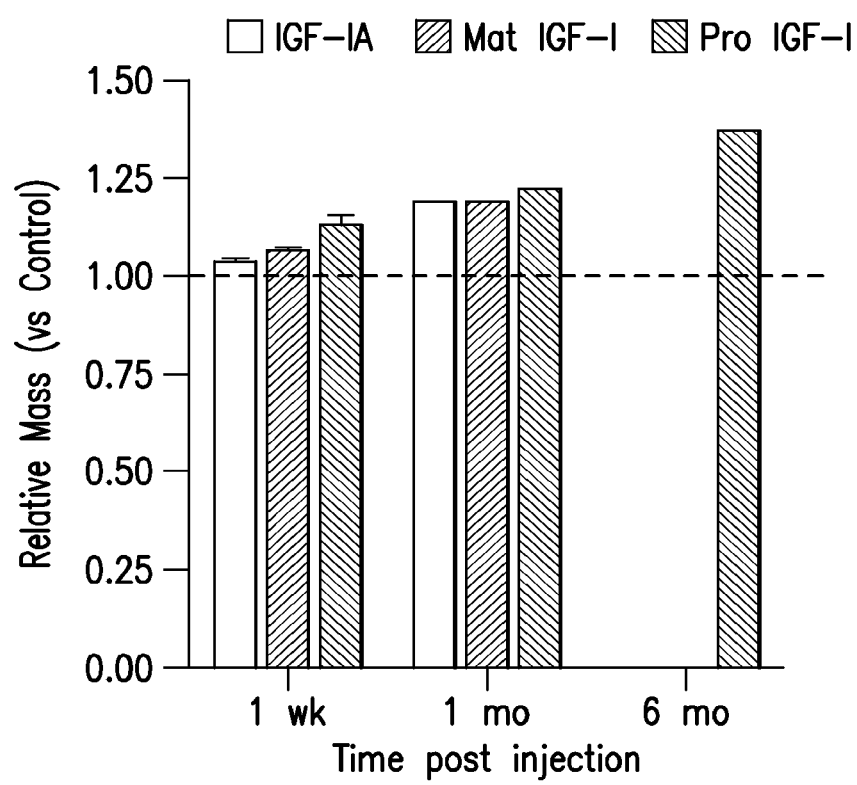
FIG. 18. Mass increase after AAV delivery of IGF-I forms. *, P<0.05 by 1-way ANOVA and Bonferroni's post hoc test for N=3 samples each. N=2 at 1 month, and N=1 at 6 months

To further test the results obtained in vitro, Adeno-associated viruses (AAVs) expressing multiple forms of IGF-I were generated, and tested in vivo. Data from animals at 1 week, 1 and 6 months post-injection reveal that pro-IGF-I causes a 13, 20, and 38% increase in muscle mass, respectively, whereas mature IGF-I causes 3 and 15% hypertrophy at the early timepoints (FIG. 18). These results indicate that pro-IGF-I can be significantly more potent at promoting functional hypertrophy than mature IGF-I To determine the in vivo effects of the pro-IGF-I and mature IGF-I proteins in vivo, the IGF-I forms are introduced into C57 male mice, by viral mediated gene transfer with scAAV2/8 harboring each IGF-I form using single limb injections (targeting anterior and posterior compartments). Changes in hindlimb muscle mass (TA, EDL, soleus, gastrocnemius) and function (isometric twitch and tetanus, specific force of EDL and soleus) is measured as primary measures of activity. This experiment is performed at 1 week and 1, 3, and 6 months post-injection to determine if any beneficial effects are maintained or are only transient, and in young (2-3 week) and adult (3 month) mice to determine if active growth is required for activity (57). To establish equivalent levels of IGF-I production from each AAV, serial dilutions of AAV is delivered to young mice and muscles will be analyzed at 1 month post-injection for IGF-I content. This allows normalization of IGF-I levels, and will also give insight into the potency of each IGF-I form. Additional outcome measures include assessment of morphology (fiber size), IGF-I content, IGF-IR phosphorylation, and downstream signaling cascades (P-Akt, P-ERK1/2) (57, 58, 55).

Three types of controls are utilized. First, each treated mouse receives an injection of an AAV encoding IGF-IStV44M, a mutation in mature IGF-I that allows proper folding of IGF-I but blocks activity (59), to control for viral load in any treated mouse. Second, a cohort of mice receives IGF-IV44M AAV injections in one limb, and no injection in the contralateral limb. This will control for variability in injection-dependent muscle size. Last, a cohort receives no injections to control for inherent variability.

Multiple comparisons among all groups are performed. For each series of injections, paired t-tests is used between treated (IGF-I form) and control (IGFStV44M) limb muscles. Second, comparisons across groups (e.g., mature vs. pro-IGF-I) utilizes 1-way ANOVA followed by Bonferroni post-hoc testing. Third, 2-way ANOVA is used for comparisons of each viral construct at each time post-injection followed by Bonferroni post-hoc testing. Sample size of N=10 per condition and timepoint will provide sufficient statistical power to detect an 8% difference in mass across conditions. The serial dilution studies requires N=4 per condition for comparisons of IGF-I content, and focuses only on mature and pro-IGF-I.

To consider the effects the mature IGF-I and pro-IGF-I forms have on mass, function, and prevention of fibrosis, the mdx mouse, a naturally occurring model for Duchenne Muscular Dystrophy (DMD) with a nonsense mutation leading to the loss of dystrophin, is used (60). Duchenne Muscular Dystrophy (DMD) is caused by loss of dystrophin and disruption of the associated glycoprotein complex. This X-linked disease can be passed from unaffected carrier females to their children, or spontaneous mutations can occur due to the gene's sheer size (2.4 megabases). Without therapeutic intervention, the 1 out of 3500 males who have DMD can die in their early teens due to respiratory and/or cardiac failure. The use of steroids can slow the progression of the muscle loss, and can help to prolong lifespan and maintain quality of life while a cure is sought (70, 71). However, there are significant side effects, which compound the primary muscle symptoms.

The mdx mouse bears many of the hallmarks of the human disease, including muscle weakness and fragility, ongoing degeneration and regeneration, and fibrotic replacement of muscle, particularly in the diaphragm. Lifespan is not diminished (73, 74) unlike patients or the more severe mouse model lacking both dystrophin and utrophin (mdx: utr-/-) (61). The mdx mouse has been used in previous studies to demonstrate that IGF-I can counter many of the secondary symptoms of the loss of dystrophin (62, 63).

Male mdx mice are injected at 3 months of age in one hindlimb and analyzed at 1, 2, and 4 months post-injection. A second cohort of mice are injected systemically to target the diaphragm, and evaluated at 2 and 4 months post-injection. At this age range, the mdx mouse has clear signs of muscle weakness and fragility, and the diaphragm exhibits significant fibrosis. Two sets of mdx mice serve as controls. One cohort of mice is injected with an AAV harboring IGFStV44M, (59). A second cohort of mice receives no injections at all. Measures include assessment of morphology (fiber size), IGF-I content, IGF-IR phosphorylation, and downstream signaling cascades (P-Akt, P-ERK1/2) (57,58,55), and also include fibrosis by Sirius red staining and hydroxyproline content. For each IGF-I form and time-point, N=14 mice are analyzed per group to provide statistical power for comparisons between groups. There is greater variability associated with the mass and function outcome measures in mdx mice. Statistical analysis is performed.

Example 5: Production of Pro-Igf-I in Chloroplasts

Even though viral mediated gene transfer is effective, it is expensive and can require many injections. In addition, the regular injections that are required for current IGF-I formulations (e.g., IPLEX® and INCRELEX®) pose a burden to patients. Therefore, the ability to provide this growth factor through oral administration is a major step forward in these therapies. Fusion proteins containing the CTB subunit that are contained within plants protect the protein until it enters the gut, where the resident microbes digest the plant cell walls to release protein, and CTB facilitates absorption into the circulation by GM1 receptors on the gut mucosa (64). Finally, release of IGF-I from the fusion construct can be mediated by furin digest of cleavage sites engineered between CTB and IGF-I. This strategy has been successful for the oral delivery of several therapeutic proteins (65, 66, 67, 68), and previous chloroplast derived IGF-I is active in vitro (69).

Recombinant proteins still have high cost, and so the development of plant based expression systems is an attractive method for producing large amounts of bioactive protein at low expense. Specifically, the choloroplast genome is a very efficient transgene vector. The high copy number of chloroplast genomes (up to 10,000 copies per plant cell) results in high yield of native and foreign proteins (Rubisco, the most abundant protein on earth, is a chloroplast protein). Foreign proteins expressed in chloroplasts fold properly with disulfide bonds. Because the chloroplast genome is maternally inherited, it does not spread through pollen and therefore is very safe with respect to the agricultural industry. Oral bioavailability is possible because the plant cell wall protects the gene product until it enters the gut.

To produce pro-IGF-I, the pLS-LF lettuce transformation vector (67), which will allow integration into the chloroplast genome, is used. The pro-IGF-I sequence undergoes codon optimization prior to insertion (69). Pro-IGF-I, harboring mutations of the subtilisin convertase cleavage site and glycosylation sites (56), will be inserted after the CTB subunit and furin cleavage sites in the pLS-LF vector. Lettuce chloroplasts will be transformed using gene gun bombardment of leaves (67, 70) and leaf pieces will be grown on media containing spectinomycin for positive selection. Homoplasmy is confirmed by southern blotting. IGF-I content in the leaves is measured by immunoblotting, utilizing antibodies for IGF-I, the EA peptide, and the CTB subunit (56, 67). Lines of lettuce that express the greatest amount of IGF-I will be used to produce biomass. Previous studies with pro-Insulin have shown that transgenic lettuce can produce ~1-3 mg/g leaf protein. For human IGF-I produced by the chloroplast system, 10-25% total soluble protein is IGF-I (69).

To determine if oral delivery of the chloroplast derived pro-IGF-I is bioavailable, male C57 mice are given homogenized lettuce in suspension by oral gavage. Animals are euthanized to obtain blood and tissues (gut, liver, skeletal muscle, heart) over the course of 24 hours to determine the extent of pro-IGF-I absorption, and the pharmacokinetics of circulating chloroplast derived pro-IGF-I. The dosing strategy will depend upon the production efficiency in the transgenic plants, but based on the production of pro-insulin by lettuce, there should be more than sufficient levels available. Injection of recombinant IGF-I serves as a positive control for this experiment. Circulating IGF-I is measured by ELISA (57, 55, 56) (provided that this is validated above for both the fusion protein and cleaved protein). Next, samples with the highest levels of IGF-I are subjected to immunoblotting to determine the extent of cleavage of the fusion protein. The gut is examined for increased immunostaining of CTB. Additional tissues are tested by immunoblotting for presence of the fusion protein. For each timepoint (0, 0.5, 1, 2, 4, 8, 16, 24 hours) N=4 male C57 mice are used.

A dosing regimen for 2 weeks is performed to determine if there is a growth response to the delivered pro-IGF-I, including increased organ mass, increased P-IGF-IR and P-AKT in tissues where the pro-IGF-I accumulates, and increased force generation. For these studies, N=10 male mice are used, and compared to vehicle control (non-transgenic lettuce). These studies will demonstrate proof-of-principle for the bioavailability of chloroplast derived pro-IGF-I and low cost production system.

REFERENCES

1. Barton E R, Morris L, Musaro A, Rosenthal N and Sweeney H L 2002 Muscle-specific expression of insulin-like growth factor I counters muscle decline in mdx mice. J Cell Biol 157: 137-48.
2. Coleman M E, DeMayo F, Yin K C, Lee H M, Geske R, Montgomery C and Schwartz R J 1995 Myogenic vector expression of insulin-like growth factor I stimulates muscle cell differentiation and myofiber hypertrophy in transgenic mice. J Biol Chem 270: 12109-16.
3. Musaro A, McCullagh K, Paul A, Houghton L, Dobrowolny G, Molinaro M, Barton E R, Sweeney H L and Rosenthal N 2001 Localized Igf-1 transgene expression sustains hypertrophy and regeneration in senescent skeletal muscle. Nat Genet 27: 195-200.
4. Barton E R 2006 Viral expression of Insulin-like Growth Factor-I isoforms promotes different responses in skeletal muscle. J Appl Physiol 100: 1778-84.
5. Barton-Davis E R, Shoturma D I, Musaro A, Rosenthal N and Sweeney H L 1998 Viral mediated expression of insulin-like growth factor I blocks the aging-related loss of skeletal muscle function. Proc Natl Acad Sci USA 95: 15603-7.
6. Stevens-Lapsley J E, Ye F, Liu M, Borst S E, Conover C, Yarasheski K E, Walter G A, Sweeney H L and Vandenborne K 2010 Impact of viral-mediated IGF-I gene transfer on skeletal muscle following cast immobilization. Am J Physiol Endocrinol Metab 299: E730-40.
7. Adams G R and McCue S A 1998 Localized infusion of IGF-I results in skeletal muscle hypertrophy in rats. J Appl Physiol 84: 1716-22.
8. Lynch G S, Cuffe S A, Plant D R and Gregorevic P 2001 IGF-I treatment improves the functional properties of fast- and slow-twitch skeletal muscles from dystrophic mice. Neuromuscul Disord 11: 260-8.
9. Barton E R 2006 The ABCs of IGF-I isoforms: impact on muscle hypertrophy and implications for repair. Appl Physiol Nutr Metab 31: 791-7.
10. Duguay S J, Milewski W M, Young B D, Nakayama K and Steiner D F 1997 Processing of Wild-type and Mutant Proinsulin-like Growth Factor-IA by Subtilisin-related Proprotein Convertases. J Biol Chem 272: 6663-6670.
11. Conover C A, Baker B K, Bale L K, Clarkson J T, Liu F and Hintz R L 1993 Human hepatoma cells synthesize and secrete insulin-like growth factor Ia prohormone under growth hormone control. Regul Pept 48: 1-8.
12. Conover C A, Baker B K and Hintz R L 1989 Cultured human fibroblasts secrete insulin-like growth factor IA prohormone. J Clin Endocrinol Metab 69: 25-30.
13. Wilson H E, Westwood M, White A and Clayton P E 2001 Monoclonal antibodies to the carboxy-terminal Ea sequence of pro-insulin-like growth factor-IA (proIGF-IA) recognize proIGF-IA secreted by IM9 B-lymphocytes. Growth Horm IGF Res 11: 10-7.
14. Bach M A, Roberts C T, Jr., Smith E P and LeRoith D 1990 Alternative splicing produces messenger RNAs encoding insulin-like growth factor-I prohormones that are differentially glycosylated in vitro. Mol Endocrinol 4: 899-904.
15. Federici M, Porzio O, Zucaro L, Fusco A, Borboni P, Lauro D and Sesti G 1997 Distribution of insulin/insulin-like growth factor-I hybrid receptors in human tissues. Mol Cell Endocrinol 129: 121-6.
16. Bailyes E M, Nave B T, Soos M A, On S R, Hayward A C and Siddle K 1997 Insulin receptor/IGF-I receptor hybrids are widely distributed in mammalian tissues: quantification of individual receptor species by selective immunoprecipitation and immunoblotting. Biochem J 327 (Pt 1): 209-15.
17. Kristensen C, Wiberg F C and Andersen A S 1999 Specificity of insulin and insulin-like growth factor I receptors investigated using chimeric mini-receptors. Role of C-terminal of receptor alpha subunit. J Biol Chem 274: 37351-6.
18. Forbes B E, Hartfield P J, McNeil K A, Surinya K H, Milner S J, Cosgrove L J and Wallace J C 2002 Characteristics of binding of insulin-like growth factor (IGF)-I and IGF-II analogues to the type 1 IGF receptor determined by BIAcore analysis. Eur J Biochem 269: 961-8.
19. De Meyts P and Whittaker J 2002 Structural biology of insulin and IGF1 receptors: implications for drug design. Nat Rev Drug Discov 1: 769-83.
20. Metzger F, Sajid W, Saenger S, Staudenmaier C, van der Poel C, Sobottka B, Schuler A, Sawitzky M, Poirier R, Tuerck D, Schick E, Schaubmar A, Hesse F, Amrein K, Loetscher H, Lynch G S, Hoeflich A, De Meyts P and Schoenfeld H J 2011 Separation of fast from slow anabolism by site-specific PEGylation of insulin-like growth factor I (IGF-I). J Biol Chem 286:19501-10.
21. Barton E R, DeMeo J and Lei H 2010 The insulin-like growth factor (IGF)-I E-peptides are required for isoform-specific gene expression and muscle hypertrophy after local IGF-I production. J Appl Physiol 108: 1069-76.

22. Philippou A, Stavropoulou A, Sourla A, Pissimissis N, Halapas A, Maridaki M and Koutsilieris M 2008 Characterization of a rabbit antihuman mechano growth factor (MGF) polyclonal antibody against the last 24 amino acids of the E domain. In Vivo 22: 27-35.
23. Pfeffer L A, Brisson B K, Lei H and Barton E R 2009 The insulin-like growth factor (IGF)-I E peptides modulate cell entry of the mature IGF-I protein. Mol Biol Cell 20: 3810-7.
24. Denley A, Wang C C, McNeil K A, Walenkamp M J, van Duyvenvoorde H, Wit J M, Wallace J C, Norton R S, Karperien M and Forbes B E 2005 Structural and functional characteristics of the Val44Met insulin-like growth factor I missense mutation: correlation with effects on growth and development. Mol Endocrinol 19: 711-21.
25. Vaj dos F F, Ultsch M, Schaffer M L, Deshayes K D, Liu J, Skelton N J and de Vos A M 2001 Crystal structure of human insulin-like growth factor-1: detergent binding inhibits binding protein interactions. Biochemistry 40: 11022-9.
26. Wallis M 2009 New insulin-like growth factor (IGF)-precursor sequences from mammalian genomes: the molecular evolution of IGFs and associated peptides in primates. Growth Horm IGF Res 19: 12-23.
27. Yuasa K, Masuda T, Yoshikawa C, Nagahama M, Matsuda Y and Tsuji A 2009 Subtilisin Like proprotein convertase PACE4 is required for skeletal muscle differentiation. J Biochem 146: 407-15.
28. Pfeffer L A, Brisson B K, Lei H, Barton E R: The insulin-like growth factor (IGF)-I E-peptides modulate cell entry of the mature IGF-I protein. Mol Biol Cell 2009, 20(17):3810-3817.
29. Fernandez A M, Dupont J, Farrar R P, Lee S, Stannard B, Le Roith D: Muscle-specific inactivation of the IGF-I receptor induces compensatory hyperplasia in skeletal muscle. J Clin Invest 2002, 109(3):347-355.
30. Brisson B K, Barton E R: Insulin-like growth factor-I E-peptide activity is dependent on the IGF-I receptor. PLoS One 2012, 7(9):e45588.
31. Denley A, Wang C C, McNeil K A, Walenkamp M J, van Duyvenvoorde H, Wit J M, Wallace J C, Norton R S, Karperien M, Forbes B E: Structural and functional characteristics of the Val44Met insulin-like growth factor I missense mutation: correlation with effects on growth and development. Mol Endocrinol 2005, 19(3):711-721.
32. Barton E R: Viral expression of insulin-like growth factor-I isoforms promotes different responses in skeletal muscle. J Appl Physiol 2006, 100(6):1778-1784.
33. Baehr L M, Furlow J D, Bodine S C: Muscle sparing in muscle RING finger 1 null mice: response to synthetic glucocorticoids. J Physiol 2011, 589(Pt 19):4759-4776.
34. McCarty D M: Self-complementary AAV vectors; advances and applications. Mol Ther 2008, 16(10):1648-1656.
35. Barton E R, Park S, James J K, Makarewich C A, Philippou A, Eletto D, Lei H, Brisson B, Ostrovsky O, Li Z et al: Deletion of muscle GRP94 impairs both muscle and body growth by inhibiting local IGF production. Faseb J 2012, 26(9):3691-3702.
36. Durzynska J, Philippou A, Brisson B K, Nguyen-McCarty M, Barton E R: The pro-Forms of Insulin-Like Growth Factor I (IGF-I) Are Predominant in Skeletal Muscle and Alter IGF-I Receptor Activation. Endocrinology 2013, 154(3): 1215-1224.
37. Bach M A, Roberts C T, Jr., Smith E P, LeRoith D: Alternative splicing produces messenger RNAs encoding insulin-like growth factor-I prohormones that are differentially glycosylated in vitro. Mol Endocrinol 1990, 4(6): 899-904.
38. Fernandez A M, Kim J K, Yakar S, Dupont J, Hernandez-Sanchez C, Castle A L, Filmore J, Shulman G I, Le Roith D: Functional inactivation of the IGF-I and insulin receptors in skeletal muscle causes type 2 diabetes. Genes Dev 2001, 15(15):1926-1934.
39. Almon R R, Dubois D C: Fiber-type discrimination in disuse and glucocorticoid-induced atrophy. Med Sci Sports Exerc 1990, 22(3):304-311.
40. Hill M, Goldspink G: Expression and splicing of the insulin-like growth factor gene in rodent muscle is associated with muscle satellite (stem) cell activation following local tissue damage. J Physiol 2003, 549(Pt 2):409-418.
41. Ates K, Yang S Y, Orrell R W, Sinanan A C, Simons P, Solomon A, Beech S, Goldspink G, Lewis M P: The IGF-I splice variant MGF increases progenitor cells in ALS, dystrophic, and normal muscle. FEBS Lett 2007, 581(14): 2727-2732.
42. Yang S Y, Goldspink G: Different roles of the IGF-I Ec peptide (MGF) and mature IGF-I in myoblast proliferation and differentiation. FEBS Lett 2002, 522(1-3):156-160.
43. Mills P, Dominique J C, Lafreniere J F, Bouchentouf M, Tremblay J P: A synthetic mechano growth factor E Peptide enhances myogenic precursor cell transplantation success. Am J Transplant 2007, 7(10):2247-2259.
44. Barton E R, DeMeo J, Lei H: The insulin-like growth factor (IGF)-I E-peptides are required for isoform-specific gene expression and muscle hypertrophy after local IGF-I production. J Appl Physiol 2010, 108(5):1069-1076.
45. Amthor H, Macharia R, Navarrete R, Schuelke M, Brown S C, Otto A, Voit T, Muntoni F, Vrbova G, Partridge T et al: Lack of myostatin results in excessive muscle growth but impaired force generation. Proc Natl Acad Sci USA 2007, 104(6):1835-1840.
46. Qaisar R, Renaud G, Morine K, Barton E R, Sweeney H L, Larsson L: Is functional hypertrophy and specific force coupled with the addition of myonuclei at the single muscle fiber level? Faseb J 2012, 26(3):1077-1085.
47. Hede M S, Salimova E, Piszczek A, Perlas E, Winn N, Nastasi T, Rosenthal N: E-peptides control bioavailability of IGF-1. PLoS One 2012, 7(12):e51152.
48. Liu J P, Baker J, Perkins A S, Robertson E J, Efstratiadis A: Mice carrying null mutations of the genes encoding insulin-like growth factor I (Igf-1) and type 1 IGF receptor (Igf1r). Cell 1993, 75(1):59-72.
49. Lynch G S, Cuffe S A, Plant D R, Gregorevic P: IGF-I treatment improves the functional properties of fast- and slow-twitch skeletal muscles from dystrophic mice. Neuromuscul Disord 2001, 11(3):260-268.
50. Musaro A, McCullagh K, Paul A, Houghton L, Dobrowolny G, Molinaro M, Barton E R, Sweeney H L, Rosenthal N: Localized Igf-1 transgene expression sustains hypertrophy and regeneration in senescent skeletal muscle. Nat Genet 2001, 27(2):195-200.
51. Goldspink G: Loss of muscle strength during aging studied at the gene level. Rejuvenation Res 2007, 10(3): 397-405.
52. Barton-Davis E R, Shoturma D I, Musaro A, Rosenthal N, Sweeney H L: Viral mediated expression of insulin-like growth factor I blocks the aging-related loss of skeletal muscle function. Proc Natl Acad Sci USA 1998, 95(26):15603-15607.

53. Brooks S V, Faulkner J A: Contractile properties of skeletal muscles from young, adult and aged mice. J Physiol 1988, 404:71-82.
54. Philippou A, Stavropoulou A, Sourla A, Pissimissis N, Halapas A, Maridaki M, Koutsilieris M: Characterization of a rabbit antihuman mechano growth factor (MGF) polyclonal antibody against the last 24 amino acids of the E domain. In Vivo 2008, 22(1):27-35.
55. Barton E R, Park S, James J K, Makarewich C A, Philippou A, Eletto D, Lei H, Brisson B, Ostrovsky O, Li Z, Argon Y. Deletion of muscle GRP94 impairs both muscle and body growth by inhibiting local IGF production. Faseb J 26: 3691-702, 2012.
56. Durzynska J, Philippou A, Brisson B K, Nguyen-McCarty M, Barton E R. The pro-forms of insulin-like growth factor I (IGF-I) are predominant in skeletal muscle and alter IGF-I receptor activation. Endocrinology 154: 1215-24, 2013.
57. Barton E R. Viral expression of insulin-like growth factor-I isoforms promotes different responses in skeletal muscle. J Appl Physiol 100: 1778-84, 2006.
58. Barton E R, Morris L, Musaro A, Rosenthal N, Sweeney H L. Muscle-specific expression of insulin-like growth factor I counters muscle decline in mdx mice. J Cell Biol 157: 137-48, 2002.
59. Denley A, Wang C C, McNeil K A, Walenkamp M J, van Duyvenvoorde H, Wit J M, Wallace J C, Norton R S, Karperien M, Forbes B E. Structural and functional characteristics of the Val44Met insulin-like growth factor I missense mutation: correlation with effects on growth and development. Mol Endocrinol 19: 711-21, 2005.
60. Sicinski P, Geng Y, Ryder-Cook A S, Barnard E A, Darlison M G, Barnard P J. The molecular basis of muscular dystrophy in the mdx mouse: a point mutation. Science 244: 1578-80, 1989.
61. Deconinck A E, Rafael J A, Skinner J A, Brown S C, Potter A C, Metzinger L, Watt D J, Dickson J G, Tinsley J M, Davies K E. Utrophin-dystrophin-deficient mice as a model for Duchenne muscular dystrophy. Cell 90: 717-27, 1997.
62. Barton E R, Morris L, Musaro A, Rosenthal N, Sweeney H L. Muscle-specific expression of insulin-like growth factor I counters muscle decline in mdx mice. J Cell Biol 157: 137-48, 2002.
63. Gregorevic P, Plant D R, Leeding K S, Bach L A, Lynch G S. Improved contractile function of the mdx dystrophic mouse diaphragm muscle after insulin-like growth factor-I administration. Am J Pathol 161: 2263-72, 2002.
64. Kwon K-C, Verma, D., Singh, N. K. Herzog, R. W. Daniell, H. Oral delivery of human biopharmaceuticals, autoantigens and vaccine antigens bioencapsulated in plant cells. Advanced Drug Delivery Reviews DOI: 10.1016/j.addr.2012.10.005, 2013.
65. Davoodi-Semiromi A, Schreiber M, Nalapalli S, Verma D, Singh N D, Banks R K, Chakrabarti D, Daniell H. Chloroplast-derived vaccine antigens confer dual immunity against cholera and malaria by oral or injectable delivery. Plant biotechnology journal 8: 223-42, 2010.
66. Kwon K C, Nityanandam R, New J S, Daniell H. Oral delivery of bioencapsulated exendin-4 expressed in chloroplasts lowers blood glucose level in mice and stimulates insulin secretion in beta-TC6 cells. Plant biotechnology journal 11: 77-86, 2013.
67. Ruhlman T, Ahangari R, Devine A, Samsam M, Daniell H. Expression of cholera toxin B-proinsulin fusion protein in lettuce and tobacco chloroplasts—oral administration protects against development of insulitis in non-obese diabetic mice. Plant biotechnology journal 5: 495-510, 2007.
68. Verma D, Moghimi B, LoDuca P A, Singh H D, Hoffman B E, Herzog R W, Daniell H. Oral delivery of bioencapsulated coagulation factor IX prevents inhibitor formation and fatal anaphylaxis in hemophilia B mice. Proceedings of the National Academy of Sciences of the United States of America 107: 7101-6, 2010.
69. Daniell H, Ruiz G, Denes B, Sandberg L, Langridge W. Optimization of codon composition and regulatory elements for expression of human insulin like growth factor-1 in transgenic chloroplasts and evaluation of structural identity and function. BMC biotechnology 9: 33, 2009.
70. Ruhlman T, Verma D, Samson N, Daniell H. The role of heterologous chloroplast sequence elements in transgene integration and expression. Plant physiology 152: 2088-104, 2010.
71. Moxley R T, 3rd, Ashwal S, Pandya S, Connolly A, Florence J, Mathews K, Baumbach L, McDonald C, Sussman M, Wade C. Practice parameter: corticosteroid treatment of Duchenne dystrophy: report of the Quality Standards Subcommittee of the American Academy of Neurology and the Practice Committee of the Child Neurology Society. Neurology 64: 13-20, 2005.
72. Reitter B. Deflazacort vs. prednisone in Duchenne muscular dystrophy: trends of an ongoing study. Brain Dev 17 Suppl: 39-43, 1995.
73. Lefaucheur J P, Pastoret C, Sebille A. Phenotype of dystrophinopathy in old mdx mice. Anat Rec 242: 70-6., 1995.
74. Pastoret C, Sebille A. mdx mice show progressive weakness and muscle deterioration with age. J Neurol Sci 129: 97-105., 1995.

The contents of all figures and all references, patents and published patent applications and Accession numbers cited throughout this application are expressly incorporated herein by reference.

The invention claimed is:

1. A pharmaceutical composition comprising a pharmaceutically acceptable carrier and a mutant pro-IGF-I protein, wherein the mutant pro-IGF-I protein comprises an amino acid sequence set forth in SEQ ID NO: 5, wherein the amino acid sequence comprises a combination of mutation K68G, a mutation at amino acid residue R71, and a mutation at amino acid residue R77.

2. The pharmaceutical composition of claim 1, wherein the pharmaceutical composition further comprises at least one of a pharmaceutically acceptable diluent, solubilizer, emulsifier, preservative, and adjuvant.

3. A kit comprising:
   (a) a container;
   (b) a pharmaceutically acceptable carrier and a mutant pro-IGF-I protein, wherein the mutant pro-IGF-I protein comprises a combination of mutation K68G, a mutation at amino acid residue R71, and a mutation at amino acid residue R77; and
   (c) instructions for use.

4. The pharmaceutical composition of claim 1, wherein the mutant pro-IGF-I protein is glycosylation deficient.

5. The pharmaceutical composition of claim 4, wherein the pharmaceutical composition comprises at least one of a pharmaceutically acceptable diluent, solubilizer, emulsifier, preservative, and adjuvant.

6. The kit of claim 3, wherein the mutant pro-IGF-I protein is glycosylation deficient.

7. The pharmaceutical composition of claim 4, wherein the mutant pro-IGF-I protein comprises a mutation at amino acid residues N92, N100, or a combination thereof.

8. The pharmaceutical composition of claim 7, wherein the mutations are N92D, N100D, or any combination thereof.

9. A pharmaceutical composition comprising:
   a pharmaceutically acceptable carrier; and
   a nucleic acid molecule encoding a mutant pro-IGF-I protein, wherein the mutant pro-IGF-I protein comprises an amino acid sequence set forth in SEQ ID NO: 5, wherein the amino acid sequence comprises a combination of mutation K68G, a mutation at amino acid residue R71, and a mutation at amino acid residue R77.

10. A pharmaceutical composition of claim 9, wherein the mutant pro-IGF-I protein is glycosylation deficient.

11. The pharmaceutical composition of claim 9, wherein mutant pro-IGF-I protein comprises at least one mutation within a proprotein convertase cleavage site.

12. The pharmaceutical composition of claim 9, wherein the amino acid sequence comprises mutations K68G, R71A, and R77A.

13. The pharmaceutical composition of claim 10, wherein the mutant pro-IGF-I protein comprises a mutation at amino acid residue N92, N100, or a combination thereof.

14. The pharmaceutical composition of claim 13, wherein the mutations are N92D, N100D, or any combination thereof.

15. A kit comprising:
   (a) a container;
   (b) a pharmaceutical composition comprising a pharmaceutically acceptable carrier and a nucleic acid molecule encoding a mutant pro-IGF-I protein, wherein the mutant pro-IGF-I protein comprises an amino acid sequence set forth in SEQ ID NO: 5, wherein the amino acid sequence comprises a combination of mutation K68G, a mutation at amino acid residue R71, and a mutation at amino acid residue R77; and
   (c) instructions for use.

16. A kit of claim 15, wherein the mutant pro-IGF-I protein is glycosylation deficient.

17. The pharmaceutical composition of claim 1, wherein the mutant pro-IGF-I protein is derived from a protein of SEQ ID NO: 1 that is mutated to become proprotein convertase cleavage deficiency.

18. The pharmaceutical composition of claim 1, wherein the amino acid sequence comprises mutations K68G, R71A, and R77A.

19. The pharmaceutical composition of claim 7, wherein the mutant pro-IGF-I protein comprises mutations at amino acid residues N92 and N100.

20. The pharmaceutical composition of claim 1, wherein the mutant pro-IGF-I protein further comprises a mutation at amino acid residues N92, N100, or combinations thereof.

21. The pharmaceutical composition of claim 20, wherein the mutant pro-IGF-I protein comprises mutations
   K68G, R71A, and R77A; and
   N92D, N100D, or combinations thereof.

22. The pharmaceutical composition of claim 1, wherein the mutant pro-IGF-I protein is furin cleavage deficient, PACE4 cleavage deficient, or both.

* * * * *